(12) United States Patent
Sealfon et al.

(10) Patent No.: US 7,723,023 B2
(45) Date of Patent: May 25, 2010

(54) USE OF INTRINSIC REPORTERS OF CELL SIGNALING FOR HIGH CONTENT DRUG PROFILING AND TOXICITY SCREENING

(75) Inventors: Stuart Sealfon, Brooklyn, NY (US); Elisa Wurmbach, New York, NY (US); Tony Yuen, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 10/218,969

(22) Filed: Aug. 14, 2002

(65) Prior Publication Data

US 2003/0165916 A1 Sep. 4, 2003

Related U.S. Application Data

(60) Provisional application No. 60/312,220, filed on Aug. 14, 2001, provisional application No. 60/324,895, filed on Sep. 26, 2001.

(51) Int. Cl.
*C12Q 1/68* (2006.01)
(52) U.S. Cl. .......................................................... 435/6
(58) Field of Classification Search ...................... 435/6, 435/91.1, 91.2, 287.2; 536/23.1, 24.32, 24.33, 536/24.1; 436/24.3
See application file for complete search history.

(56) References Cited

U.S. PATENT DOCUMENTS

| 6,847,897 | B1 * | 1/2005 | Bassett et al. ................. 702/19 |
| 2001/0007748 | A1 | 7/2001 | An et al. |
| 2001/0031462 | A1 * | 10/2001 | Glynne et al. ................. 435/4 |
| 2002/0064788 | A1 * | 5/2002 | Monforte ....................... 435/6 |
| 2003/0148295 | A1 * | 8/2003 | Wan et al. ..................... 435/6 |

FOREIGN PATENT DOCUMENTS

EP 0 370 813 11/1989

OTHER PUBLICATIONS

Heid et al. Real time Quantitative PCR. Benome Research. vol. 6, No. 10, pp. 986-994. Oct. 1996.*
Oguchi et al. FEBS Letters, vol. 338, pp. 326-330, 1994.*
Lukiw et al. The Journal of Biological Chemistry, vol. 274, No. 13, pp. 8630-8638, Mar. 1999.*
Hope et al. Proc. Natl. Acad. Sci. USA, vol. 89, pp. 5764-5768, Jul. 1992.*
Chauhan et al. Cancer Reseach, vol. 54, pp. 2234-2239, Apr. 1994.*

* cited by examiner

*Primary Examiner*—Gary Benzion
*Assistant Examiner*—Cynthia B Wilder

(57) ABSTRACT

The present invention identifies essentially all of the members of a specific group of genes that are preferentially transcribed upon the initialization of a signal transduction pathway. The present invention also discloses methods for detecting and/or quantifying the transcription of these specific genes. The present invention further discloses methods of using this information to characterize the effect of potential drugs on a cell. Solid supports comprising nucleic acids that can hybridize with the transcripts from this specific group of genes are also described.

22 Claims, 16 Drawing Sheets

A

B

SEQUENCE LISTING

<160> NUMBER OF SEQ ID NOS: 120

<210> SEQ ID NO 1
<211> LENGTH: 23
<212> TYPE: DNA
<213> ORGANISM: Homo sapiens

<400> SEQUENCE: 1
cgttttacaa cgtcgtgact ggg                                              23

<210> SEQ ID NO 2
<211> LENGTH: 63
<212> TYPE: DNA
<213> ORGANISM: Homo sapiens

<400> SEQUENCE: 2
ggccagtgaa ttgtaatacg actcactata gggaggcggt ttttttttt ttttttttt       60 ttt                                                                    63

<210> SEQ ID NO 3
<211> LENGTH: 19
<212> TYPE: DNA
<213> ORGANISM: Homo sapiens

<400> SEQUENCE: 3
tgacatgcgc gtatgagag                                                   19

<210> SEQ ID NO 4
<211> LENGTH: 20
<212> TYPE: DNA
<213> ORGANISM: Homo sapiens

<400> SEQUENCE: 4
ctggctttgt ctgtcagtgc                                                  20

<210> SEQ ID NO 5
<211> LENGTH: 20
<212> TYPE: DNA
<213> ORGANISM: Homo sapiens

<400> SEQUENCE: 5
acctttctgg cctgcatctc                                                  20

<210> SEQ ID NO 6
<211> LENGTH: 20
<212> TYPE: DNA
<213> ORGANISM: Homo sapiens

<400> SEQUENCE: 6
caagaaggtg aggctcaagg                                                  20

<210> SEQ ID NO 7
<211> LENGTH: 20
<212> TYPE: DNA
<213> ORGANISM: Homo sapiens

<400> SEQUENCE: 7
caggctcttc cttcagttgg                                                  20

<210> SEQ ID NO 8
<211> LENGTH: 20

```
<212> TYPE: DNA
<213> ORGANISM: Homo sapiens

<400> SEQUENCE: 8
gactttccat ctgcctccac                                                  20

<210> SEQ ID NO 9
<211> LENGTH: 20
<212> TYPE: DNA
<213> ORGANISM: Homo sapiens

<400> SEQUENCE: 9
gtgggaagaa ggagaacctg                                                  20

<210> SEQ ID NO 10
<211> LENGTH: 20
<212> TYPE: DNA
<213> ORGANISM: Homo sapiens

<400> SEQUENCE: 10
ctggagtgtt gatggagcag                                                  20

<210> SEQ ID NO 11
<211> LENGTH: 20
<212> TYPE: DNA
<213> ORGANISM: Homo sapiens

<400> SEQUENCE: 11
atgtgtgagt ggtgcctgtc                                                  20

<210> SEQ ID NO 12
<211> LENGTH: 20
<212> TYPE: DNA
<213> ORGANISM: Homo sapiens

<400> SEQUENCE: 12
tgctgtttca tccctgtgtc                                                  20

<210> SEQ ID NO 13
<211> LENGTH: 20
<212> TYPE: DNA
<213> ORGANISM: Homo sapiens

<400> SEQUENCE: 13
atgctgtctc gccatctctc                                                  20

<210> SEQ ID NO 14
<211> LENGTH: 20
<212> TYPE: DNA
<213> ORGANISM: Homo sapiens

<400> SEQUENCE: 14
cattcataag gacgcagcac                                                  20

<210> SEQ ID NO 15
<211> LENGTH: 20
<212> TYPE: DNA
<213> ORGANISM: Homo sapiens

<400> SEQUENCE: 15
aggtgacagc attgcttctg                                                  20

<210> SEQ ID NO 16
```

```
<211> LENGTH: 19
<212> TYPE: DNA
<213> ORGANISM: Homo sapiens

<400> SEQUENCE: 16
gctgcctcaa cacctcaac                                          19

<210> SEQ ID NO 17
<211> LENGTH: 20
<212> TYPE: DNA
<213> ORGANISM: Homo sapiens

<400> SEQUENCE: 17
ttcctggcaa tagcgtgttc                                         20

<210> SEQ ID NO 18
<211> LENGTH: 20
<212> TYPE: DNA
<213> ORGANISM: Homo sapiens

<400> SEQUENCE: 18
ttcagaccac ctcgacaatg                                         20

<210> SEQ ID NO 19
<211> LENGTH: 20
<212> TYPE: DNA
<213> ORGANISM: Homo sapiens

<400> SEQUENCE: 19
tgaaagctgt gtccctgtc                                          20

<210> SEQ ID NO 20
<211> LENGTH: 20
<212> TYPE: DNA
<213> ORGANISM: Homo sapiens

<400> SEQUENCE: 20
gaagggattg ttggcagttc                                         20

<210> SEQ ID NO 21
<211> LENGTH: 20
<212> TYPE: DNA
<213> ORGANISM: Homo sapiens

<400> SEQUENCE: 21
aggcgtccgt tgtgagttac                                         20

<210> SEQ ID NO 22
<211> LENGTH: 20
<212> TYPE: DNA
<213> ORGANISM: Homo sapiens

<400> SEQUENCE: 22
ttcctgcttc gtgtgttgtc                                         20

<210> SEQ ID NO 23
<211> LENGTH: 21
<212> TYPE: DNA
<213> ORGANISM: Homo sapiens

<400> SEQUENCE: 23
gattgcagaa gaggtgactg g                                       21
```

```
<210> SEQ ID NO 24
<211> LENGTH: 21
<212> TYPE: DNA
<213> ORGANISM: Homo sapiens

<400> SEQUENCE: 24
cagccaagtg gtagctgaga c                                           21

<210> SEQ ID NO 25
<211> LENGTH: 21
<212> TYPE: DNA
<213> ORGANISM: Homo sapiens

<400> SEQUENCE: 25
tgagtgctga gtgatgtcag g                                           21

<210> SEQ ID NO 26
<211> LENGTH: 20
<212> TYPE: DNA
<213> ORGANISM: Homo sapiens

<400> SEQUENCE: 26
tcctctccat cacatgcctg                                             20

<210> SEQ ID NO 27
<211> LENGTH: 20
<212> TYPE: DNA
<213> ORGANISM: Homo sapiens

<400> SEQUENCE: 27
cactctgaca catgctccag                                             20

<210> SEQ ID NO 28
<211> LENGTH: 21
<212> TYPE: DNA
<213> ORGANISM: Homo sapiens

<400> SEQUENCE: 28
tgttaacagg gtctgcatgt g                                           21

<210> SEQ ID NO 29
<211> LENGTH: 19
<212> TYPE: DNA
<213> ORGANISM: Homo sapiens

<400> SEQUENCE: 29
agcggcagtg acattgaag                                              19

<210> SEQ ID NO 30
<211> LENGTH: 20
<212> TYPE: DNA
<213> ORGANISM: Homo sapiens

<400> SEQUENCE: 30 gagcctttc taccgtgtgg                                              20

<210> SEQ ID NO 31
<211> LENGTH: 20
<212> TYPE: DNA
<213> ORGANISM: Homo sapiens

<400> SEQUENCE: 31
gagcagggac aggacaagac                                             20
```

<210> SEQ ID NO 32
<211> LENGTH: 20
<212> TYPE: DNA
<213> ORGANISM: Homo sapiens

<400> SEQUENCE: 32
tggatctctg tgagcaccac                                          20

<210> SEQ ID NO 33
<211> LENGTH: 20
<212> TYPE: DNA
<213> ORGANISM: Homo sapiens

<400> SEQUENCE: 33
aggcaactaa caaccgatgg                                          20

<210> SEQ ID NO 34
<211> LENGTH: 20
<212> TYPE: DNA
<213> ORGANISM: Homo sapiens

<400> SEQUENCE: 34
tgcgacttca acagcaactc                                          20

<210> SEQ ID NO 35
<211> LENGTH: 20
<212> TYPE: DNA
<213> ORGANISM: Homo sapiens

<400> SEQUENCE: 35
cttgctcagt gtccttgctg                                          20

<210> SEQ ID NO 36
<211> LENGTH: 20
<212> TYPE: DNA
<213> ORGANISM: Homo sapiens

<400> SEQUENCE: 36
caggcttctg ttctgctgtg                                          20

<210> SEQ ID NO 37
<211> LENGTH: 20
<212> TYPE: DNA
<213> ORGANISM: Homo sapiens

<400> SEQUENCE: 37
tacttccggt tagggtgctc                                          20

<210> SEQ ID NO 38
<211> LENGTH: 20
<212> TYPE: DNA
<213> ORGANISM: Homo sapiens

<400> SEQUENCE: 38
ttaagacacg cttcgggttc                                          20

<210> SEQ ID NO 39
<211> LENGTH: 20
<212> TYPE: DNA
<213> ORGANISM: Homo sapiens

<400> SEQUENCE: 39
tatgcagtga gcccttctcc                                          20

```
<210> SEQ ID NO 40
<211> LENGTH: 20
<212> TYPE: DNA
<213> ORGANISM: Homo sapiens

<400> SEQUENCE: 40
tgatggtgct tggtgagttg                                              20

<210> SEQ ID NO 41
<211> LENGTH: 20
<212> TYPE: DNA
<213> ORGANISM: Homo sapiens

<400> SEQUENCE: 41
ttgcacatct gaaaccacag                                              20

<210> SEQ ID NO 42
<211> LENGTH: 21
<212> TYPE: DNA
<213> ORGANISM: Homo sapiens

<400> SEQUENCE: 42
cctgtctctt cctacccaac c                                            21

<210> SEQ ID NO 43
<211> LENGTH: 20
<212> TYPE: DNA
<213> ORGANISM: Homo sapiens

<400> SEQUENCE: 43
gcaggagtgt ccgtgtcttc                                              20

<210> SEQ ID NO 44
<211> LENGTH: 20
<212> TYPE: DNA
<213> ORGANISM: Homo sapiens

<400> SEQUENCE: 44
actcccagct tggggattag                                              20

<210> SEQ ID NO 45
<211> LENGTH: 20
<212> TYPE: DNA
<213> ORGANISM: Homo sapiens

<400> SEQUENCE: 45
tactaggcga ccccagacag                                              20

<210> SEQ ID NO 46
<211> LENGTH: 20
<212> TYPE: DNA
<213> ORGANISM: Homo sapiens

<400> SEQUENCE: 46
ggatctcaat gaaggcaagc                                              20

<210> SEQ ID NO 47
<211> LENGTH: 20
<212> TYPE: DNA
<213> ORGANISM: Homo sapiens

<400> SEQUENCE: 47
```

-continued ttgctgctgg tgctgataac                                           20

<210> SEQ ID NO 48
<211> LENGTH: 20
<212> TYPE: DNA
<213> ORGANISM: Homo sapiens

<400> SEQUENCE: 48
gtgcctgctt aggagctctg                                           20

<210> SEQ ID NO 49
<211> LENGTH: 20
<212> TYPE: DNA
<213> ORGANISM: Homo sapiens

<400> SEQUENCE: 49
cctccaccct acagaattgg                                           20

<210> SEQ ID NO 50
<211> LENGTH: 20
<212> TYPE: DNA
<213> ORGANISM: Homo sapiens

<400> SEQUENCE: 50
gccagcatca caagcaatac                                           20

<210> SEQ ID NO 51
<211> LENGTH: 20
<212> TYPE: DNA
<213> ORGANISM: Homo sapiens

<400> SEQUENCE: 51
tctgagaagt gccaggtgtg                                           20

<210> SEQ ID NO 52
<211> LENGTH: 20
<212> TYPE: DNA
<213> ORGANISM: Homo sapiens

<400> SEQUENCE: 52
cttccgtttg ccttgaactc                                           20

<210> SEQ ID NO 53
<211> LENGTH: 20
<212> TYPE: DNA
<213> ORGANISM: Homo sapiens

<400> SEQUENCE: 53
tcaggatgca acctcaacag                                           20

<210> SEQ ID NO 54
<211> LENGTH: 20
<212> TYPE: DNA
<213> ORGANISM: Homo sapiens

<400> SEQUENCE: 54
ttcgtgtttg ctctggtctg                                           20

<210> SEQ ID NO 55
<211> LENGTH: 20
<212> TYPE: DNA
<213> ORGANISM: Homo sapiens

<400> SEQUENCE: 55

```
gcctgactga tacgcagttc                                              20

<210> SEQ ID NO 56
<211> LENGTH: 20
<212> TYPE: DNA
<213> ORGANISM: Homo sapiens

<400> SEQUENCE: 56
atggcttgga aaagccagac                                              20

<210> SEQ ID NO 57
<211> LENGTH: 20
<212> TYPE: DNA
<213> ORGANISM: Homo sapiens

<400> SEQUENCE: 57
tcgctcttgt tgaaatgtgg                                              20

<210> SEQ ID NO 58
<211> LENGTH: 20
<212> TYPE: DNA
<213> ORGANISM: Homo sapiens

<400> SEQUENCE: 58
tcatagggca gctcatcctc                                              20

<210> SEQ ID NO 59
<211> LENGTH: 20
<212> TYPE: DNA
<213> ORGANISM: Homo sapiens

<400> SEQUENCE: 59
tggaagagag aacgggagtg                                              20

<210> SEQ ID NO 60
<211> LENGTH: 20
<212> TYPE: DNA
<213> ORGANISM: Homo sapiens

<400> SEQUENCE: 60
aaaagagagg ggatggtgtc                                              20

<210> SEQ ID NO 61
<211> LENGTH: 20
<212> TYPE: DNA
<213> ORGANISM: Homo sapiens

<400> SEQUENCE: 61
cgagcgttga agacaatgag                                              20

<210> SEQ ID NO 62
<211> LENGTH: 20
<212> TYPE: DNA
<213> ORGANISM: Homo sapiens

<400> SEQUENCE: 62
atgtcaggaa gggacacgag                                              20

<210> SEQ ID NO 63
<211> LENGTH: 20
<212> TYPE: DNA
<213> ORGANISM: Homo sapiens
```

```
<400> SEQUENCE: 63
ctttgtgcca acagaggatg                                              20

<210> SEQ ID NO 64
<211> LENGTH: 20
<212> TYPE: DNA
<213> ORGANISM: Homo sapiens

<400> SEQUENCE: 64
aggctgtggc tgtggttatc                                              20

<210> SEQ ID NO 65
<211> LENGTH: 20
<212> TYPE: DNA
<213> ORGANISM: Homo sapiens

<400> SEQUENCE: 65
cgggttattc ttgtgactcg                                              20

<210> SEQ ID NO 66
<211> LENGTH: 21
<212> TYPE: DNA
<213> ORGANISM: Homo sapiens

<400> SEQUENCE: 66
gcataagtga aagggcaga c                                             21

<210> SEQ ID NO 67
<211> LENGTH: 20
<212> TYPE: DNA
<213> ORGANISM: Homo sapiens

<400> SEQUENCE: 67 tgactttag cggcacgaac                                               20

<210> SEQ ID NO 68
<211> LENGTH: 20
<212> TYPE: DNA
<213> ORGANISM: Homo sapiens

<400> SEQUENCE: 68
gactcaagcg aaggtggaac                                              20

<210> SEQ ID NO 69
<211> LENGTH: 20
<212> TYPE: DNA
<213> ORGANISM: Homo sapiens

<400> SEQUENCE: 69
ggggcttata ctcccaaacc                                              20

<210> SEQ ID NO 70
<211> LENGTH: 20
<212> TYPE: DNA
<213> ORGANISM: Homo sapiens

<400> SEQUENCE: 70
cctccctcct gaagcctaac                                              20

<210> SEQ ID NO 71
<211> LENGTH: 20
<212> TYPE: DNA
<213> ORGANISM: Homo sapiens
```

<400> SEQUENCE: 71
ccagagggag agttcgtgtc                                          20

<210> SEQ ID NO 72
<211> LENGTH: 20
<212> TYPE: DNA
<213> ORGANISM: Homo sapiens

<400> SEQUENCE: 72
aaagcggtct ccttttcctc                                          20

<210> SEQ ID NO 73
<211> LENGTH: 20
<212> TYPE: DNA
<213> ORGANISM: Homo sapiens

<400> SEQUENCE: 73
tcgtcaggga agggttagag                                          20

<210> SEQ ID NO 74
<211> LENGTH: 20
<212> TYPE: DNA
<213> ORGANISM: Homo sapiens

<400> SEQUENCE: 74
ccgccaaaga aaacagacac                                          20

<210> SEQ ID NO 75
<211> LENGTH: 20
<212> TYPE: DNA
<213> ORGANISM: Homo sapiens

<400> SEQUENCE: 75
cagcatgtta cgtgatgagg                                          20

<210> SEQ ID NO 76
<211> LENGTH: 20
<212> TYPE: DNA
<213> ORGANISM: Homo sapiens

<400> SEQUENCE: 76
gctcagaaaa ggctccatcc                                          20

<210> SEQ ID NO 77
<211> LENGTH: 20
<212> TYPE: DNA
<213> ORGANISM: Homo sapiens

<400> SEQUENCE: 77
gggtgacccc actatttgtc                                          20

<210> SEQ ID NO 78
<211> LENGTH: 20
<212> TYPE: DNA
<213> ORGANISM: Homo sapiens

<400> SEQUENCE: 78
cggaagagat ctcgagttgg                                          20

<210> SEQ ID NO 79
<211> LENGTH: 19
<212> TYPE: DNA

```
<213> ORGANISM: Homo sapiens

<400> SEQUENCE: 79
aagcaggatc ccaaacgtc                                              19

<210> SEQ ID NO 80
<211> LENGTH: 21
<212> TYPE: DNA
<213> ORGANISM: Homo sapiens

<400> SEQUENCE: 80
caccagatca ccttcagttc c                                           21

<210> SEQ ID NO 81
<211> LENGTH: 20
<212> TYPE: DNA
<213> ORGANISM: Homo sapiens

<400> SEQUENCE: 81
cctagggact gggaagtgac                                             20

<210> SEQ ID NO 82
<211> LENGTH: 20
<212> TYPE: DNA
<213> ORGANISM: Homo sapiens

<400> SEQUENCE: 82
tgtctacggc agcaactacg                                             20

<210> SEQ ID NO 83
<211> LENGTH: 21
<212> TYPE: DNA
<213> ORGANISM: Homo sapiens

<400> SEQUENCE: 83
cgtcactgag gacacttttg c                                           21

<210> SEQ ID NO 84
<211> LENGTH: 18
<212> TYPE: DNA
<213> ORGANISM: Homo sapiens

<400> SEQUENCE: 84
cggtgcccaa cattcaac                                               18

<210> SEQ ID NO 85
<211> LENGTH: 20
<212> TYPE: DNA
<213> ORGANISM: Homo sapiens

<400> SEQUENCE: 85
ttgttgggag cacacacttc                                             20

<210> SEQ ID NO 86
<211> LENGTH: 19
<212> TYPE: DNA
<213> ORGANISM: Homo sapiens

<400> SEQUENCE: 86
ccctaaaagt gcccaggtg                                              19

<210> SEQ ID NO 87
<211> LENGTH: 20
```

```
<212> TYPE: DNA
<213> ORGANISM: Homo sapiens

<400> SEQUENCE: 87
acttcgacgg cttctgtgtg                                          20

<210> SEQ ID NO 88
<211> LENGTH: 20
<212> TYPE: DNA
<213> ORGANISM: Homo sapiens

<400> SEQUENCE: 88
gtggccatgt ccctgtagtc                                          20

<210> SEQ ID NO 89
<211> LENGTH: 20
<212> TYPE: DNA
<213> ORGANISM: Homo sapiens

<400> SEQUENCE: 89
gctttcctga taccagatcg                                          20

<210> SEQ ID NO 90
<211> LENGTH: 20
<212> TYPE: DNA
<213> ORGANISM: Homo sapiens

<400> SEQUENCE: 90
gcgtggaaac tgacagacac                                          20

<210> SEQ ID NO 91
<211> LENGTH: 20
<212> TYPE: DNA
<213> ORGANISM: Homo sapiens

<400> SEQUENCE: 91
gctacatgag accaggagtc                                          20

<210> SEQ ID NO 92
<211> LENGTH: 20
<212> TYPE: DNA
<213> ORGANISM: Homo sapiens

<400> SEQUENCE: 92
cctaggttgc tgacttcctg                                          20

<210> SEQ ID NO 93
<211> LENGTH: 20
<212> TYPE: DNA
<213> ORGANISM: Homo sapiens

<400> SEQUENCE: 93
gggtcttcgg ttaaggttgc                                          20

<210> SEQ ID NO 94
<211> LENGTH: 20
<212> TYPE: DNA
<213> ORGANISM: Homo sapiens

<400> SEQUENCE: 94
ttcacggacc tggatcctac                                          20

<210> SEQ ID NO 95
```

-continued

```
<211> LENGTH: 20
<212> TYPE: DNA
<213> ORGANISM: Homo sapiens

<400> SEQUENCE: 95
tctgtggcaa gaccaagatg                                          20

<210> SEQ ID NO 96
<211> LENGTH: 20
<212> TYPE: DNA
<213> ORGANISM: Homo sapiens

<400> SEQUENCE: 96
gacagcaggg cttctactgg                                          20

<210> SEQ ID NO 97
<211> LENGTH: 20
<212> TYPE: DNA
<213> ORGANISM: Homo sapiens

<400> SEQUENCE: 97
atctacaagc gaggctacgg                                          20

<210> SEQ ID NO 98
<211> LENGTH: 20
<212> TYPE: DNA
<213> ORGANISM: Homo sapiens

<400> SEQUENCE: 98
tggggaagac agtttgaagg                                          20

<210> SEQ ID NO 99
<211> LENGTH: 20
<212> TYPE: DNA
<213> ORGANISM: Homo sapiens

<400> SEQUENCE: 99
cgtgacgaag atgaagatgc                                          20

<210> SEQ ID NO 100
<211> LENGTH: 20
<212> TYPE: DNA
<213> ORGANISM: Homo sapiens

<400> SEQUENCE: 100
gcacattgaa tcgcacagtc                                          20

<210> SEQ ID NO 101
<211> LENGTH: 20
<212> TYPE: DNA
<213> ORGANISM: Homo sapiens

<400> SEQUENCE: 101
aggttgtggt gtctgggaag                                          20

<210> SEQ ID NO 102
<211> LENGTH: 20
<212> TYPE: DNA
<213> ORGANISM: Homo sapiens

<400> SEQUENCE: 102
gaggcttctt gggaccaatc                                          20
```

```
<210> SEQ ID NO 103
<211> LENGTH: 20
<212> TYPE: DNA
<213> ORGANISM: Homo sapiens

<400> SEQUENCE: 103
aattctgcct tcctcgtctg                                              20

<210> SEQ ID NO 104
<211> LENGTH: 20
<212> TYPE: DNA
<213> ORGANISM: Homo sapiens

<400> SEQUENCE: 104
aaccccagta ctgcctcatc                                              20

<210> SEQ ID NO 105
<211> LENGTH: 20
<212> TYPE: DNA
<213> ORGANISM: Homo sapiens

<400> SEQUENCE: 105
acctctgagt ctggggatgg                                              20

<210> SEQ ID NO 106
<211> LENGTH: 20
<212> TYPE: DNA
<213> ORGANISM: Homo sapiens

<400> SEQUENCE: 106
aagtgcagag ccaggagttc                                              20

<210> SEQ ID NO 107
<211> LENGTH: 21
<212> TYPE: DNA
<213> ORGANISM: Homo sapiens

<400> SEQUENCE: 107
cgactcatga tagcagggaa c                                            21

<210> SEQ ID NO 108
<211> LENGTH: 20
<212> TYPE: DNA
<213> ORGANISM: Homo sapiens

<400> SEQUENCE: 108
agaagctcat gttcggcatc                                              20

<210> SEQ ID NO 109
<211> LENGTH: 21
<212> TYPE: DNA
<213> ORGANISM: Homo sapiens

<400> SEQUENCE: 109
tcagctcctc agtttctgct c                                            21

<210> SEQ ID NO 110
<211> LENGTH: 20
<212> TYPE: DNA
<213> ORGANISM: Homo sapiens

<400> SEQUENCE: 110
gtgtgcggac aaaacacaag                                              20
```

```
<210> SEQ ID NO 111
<211> LENGTH: 20
<212> TYPE: DNA
<213> ORGANISM: Homo sapiens

<400> SEQUENCE: 111
aggtgggtgt ggagtttgag                                              20

<210> SEQ ID NO 112
<211> LENGTH: 20
<212> TYPE: DNA
<213> ORGANISM: Homo sapiens

<400> SEQUENCE: 112
tattcttgcg gtggttcagg                                              20

<210> SEQ ID NO 113
<211> LENGTH: 19
<212> TYPE: DNA
<213> ORGANISM: Homo sapiens

<400> SEQUENCE: 113
gatgctgcac cgacacttc                                               19

<210> SEQ ID NO 114
<211> LENGTH: 20
<212> TYPE: DNA
<213> ORGANISM: Homo sapiens

<400> SEQUENCE: 114 cccccttagcc acagtgagag                                             20

<210> SEQ ID NO 115
<211> LENGTH: 20
<212> TYPE: DNA
<213> ORGANISM: Homo sapiens

<400> SEQUENCE: 115
ggcaaaaacc acacctgaag                                              20

<210> SEQ ID NO 116
<211> LENGTH: 20
<212> TYPE: DNA
<213> ORGANISM: Homo sapiens

<400> SEQUENCE: 116
acaggtgagg tgcagaaacc                                              20

<210> SEQ ID NO 117
<211> LENGTH: 20
<212> TYPE: DNA
<213> ORGANISM: Homo sapiens

<400> SEQUENCE: 117
tgcctttgtg cactggtatg                                              20

<210> SEQ ID NO 118
<211> LENGTH: 20
<212> TYPE: DNA
<213> ORGANISM: Homo sapiens

<400> SEQUENCE: 118
ctggagcagt ttgacgacac                                              20
```

```
<210> SEQ ID NO 119
<211> LENGTH: 20
<212> TYPE: DNA
<213> ORGANISM: Homo sapiens

<400> SEQUENCE: 119
gaaagcaagc atgtggtgtg                                               20

<210> SEQ ID NO 120
<211> LENGTH: 21
<212> TYPE: DNA
<213> ORGANISM: Homo sapiens

<400> SEQUENCE: 120
cactctttgg gtgacaagct c                                             21
```

USE OF INTRINSIC REPORTERS OF CELL SIGNALING FOR HIGH CONTENT DRUG PROFILING AND TOXICITY SCREENING

RELATED PATENT APPLICATIONS

This application claims priority under 35 USC §119(e) to U.S. Ser. Nos. 60/312,220, filed 14 Aug. 2001 and 60/324,895, filed 26 Sep. 2001, both of which applications are herein specifically incorporated by reference in their entirety.

GOVERNMENT SUPPORT

The research leading to the present invention was supported in part by NIH Grants DA 12923 and DK 46943. The government may have certain rights in the present invention.

FIELD OF THE INVENTION

The present invention relates to methods for monitoring cell signaling with the use of a specific group of genes that are preferentially transcribed upon the initialization of signal transduction pathways. The present invention also relates to processes that detect and/or accurately quantify the induction of such transcripts. The present invention further relates to methods of using these processes to characterize the effect of drugs on a cell.

BACKGROUND OF THE INVENTION

The mechanisms underlying the specificity of the responses elicited by activation of cell surface receptors are not well understood. The pituitary gonadotropin-releasing hormone receptor (GnRHR), which mediates the biosynthesis of the gonadotropins luteinizing hormone and follicle stimulating hormone, provides a salient example of the exquisite requirements for signaling specificity between the membrane and the genome. The pattern of downstream gene responses depends on the frequency of receptor stimulation. Specific patterns of GnRHR stimulation lead to the generation of distinct transcriptional programs. For example, prolonged GnRH stimulation favor induction of the common α-gona dotropin. In contrast, a specific physiologically-relevant frequency range of receptor stimulation, on the order of one pulse/hour, preferentially induces the luteinizing hormone beta subunit (LHβ) gene (see, for example, Dalkin et al. (1989) Endocrinology 125:917-24). Whereas downstream signal transduction mediators including JNK and ERK and a number of transcription factors including Egr1, SF1 and NAB1 have been implicated in modulation of the LHβ promoter (see for example Kaiser et al. (2000) Mol. Endocrinol. 14:1235-45), the available data do not explain why the induction of LHβ requires specific patterns of GnRHR activation. Furthermore, whereas it has recently been proposed that signal transduction pathways may form complex networks that manifest emergent properties whose overall patterns of activity are relatively independent of the behavior of specific components (Bhalla et al. (1999) Science 283 381-7), heretofore there has been no methodology to specifically delineate these inter-related roles of the products of the genes comprising these complex networks. Moreover, there has been no methodology to specifically exploit the general information that can be elucidated from these complex networks.

Microarray techniques have emerged as important approaches for the simultaneous analysis of multiple gene transcripts. Microarrays have proven valuable in refining cancer classification (see, for example, Alizadeh et al. (2000) Nature 403:503-11) and for providing qualitative assessment of the global gene programs that accompany cell division, development, and the responses to specific stimuli (see, for example, Iyer et al. (1999) Science 283:381-7). However, data obtained using both commercial and custom global microarrays have been limited by the expense of the assays and by problems in quality control (Knight (2001) Nature 410:860-1). The scale of genome-wide microarrays brings several problems. One is the difficulty of quality control for both academic and commercial suppliers. Another is the increase in statistical uncertainty due to multiple hypothesis testing. For an experiment utilizing a fixed number of arrays, the statistical power of correctly assigning a gene as regulated or unregulated decreases as the size of the array increases. However the high expense of global arrays constrains the number of arrays that should be analyzed to provide statistically acceptable sensitivity and specificity.

Therefore, there is a need to provide microarrays that are constructed to contain a limited number of nucleic acids affixed to them, yet still be able to allow the accurate identification of a subset of genes that are affected by a given biological interaction. In addition, there is a need to identify the specific set of genes that play a role in the initial stages of signal transduction pathways.

SUMMARY OF THE INVENTION

The present invention discloses the identity of a finite group of genes (see Table 1) and orthologs thereof that contain essentially all of the genes that are rapidly transcribed upon the initialization of a signal transduction pathway by any given factor/agent. Since different subsets of this single group of genes are affected by individual factors/agents, the pattern of the relative expression of these genes, as disclosed herein, provides critical information regarding the effect of any given factor/agent on a cell, tissue and/or organism that it comes in contact with. Thus, the present invention provides a method of identifying/testing compounds through the identification of the genes (termed herein "intrinsic reporters of cell signaling") transcribed in a cell that is contacted with a given individual factor/agent.

The present invention also provides methods of detecting and accurately quantifying the relative levels of expression of RNA transcripts. The present invention further provides solid supports that comprise nucleic acids that contain the coding and/or untranslated sequences of RNA transcripts for this specific group of genes and/or complementary strands thereof.

One aspect of the present invention provides a solid substrate that comprises a plurality of different polymers coupled to a solid substrate, with each different polymer being affixed to the solid substrate in a different/separate known location. In one embodiment, the plurality of different polymers comprises 3 to 10,000 different polymers. In another embodiment, the plurality of different polymers comprises 5 to 5,000 different polymers. In yet another embodiment, the plurality of different polymers comprises 10 to 1000 different polymers. In still another embodiment, the plurality of different polymers comprises 50 to 500 different polymers. In a preferred embodiment, the plurality of different polymers comprises 100 to 400 different polymers.

In one embodiment, the polymer comprises a protein. In another embodiment the polymer comprises a carbohydrate. In still another embodiment, the polymer comprises a lipid. In a preferred embodiment, the polymer comprises a nucleic acid. Preferably the different polymers have different compositions and/or sequences, e.g., nucleic acids having different nucleotide sequences. In a particularly preferred embodiment of this type, the different polymers are nucleic acids that are obtained from and/or hybridize to RNA transcripts from different genes. In a preferred embodiment, the nucleic acids are and/or correspond to RNA transcripts that comprise predominantly or exclusively 3'-untranslated sequence of a cDNA and/or the complementary strand thereof.

Preferably at least two copies of each different polymer are present on the solid substrate in a different/separate known location. Even more preferably, at least three copies of each different polymer are present on the solid substrate in a different/separate known location.

Accordingly, the present invention provides a solid substrate comprising a plurality of different nucleic acids with each different nucleic acid being capable of hybridizing with specificity (e.g., preferably being a sequence long enough to allow unambiguous hybridization) to at least a portion of an RNA transcript from a different gene. In a preferred embodiment of this type, at least 10% of the different nucleic acids affixed to the solid support hybridize to at least a portion of an RNA transcript from a different intrinsic reporter of cell signaling. In this case, the remaining 90% or fewer different nucleic acids affixed to the solid support would hybridize to at least another portion of an RNA transcript from the different intrinsic reporters of cell signaling, or alternatively to at least a portion of an RNA transcript from a different non-intrinsic reporter of cell signaling, such as a housekeeping gene (e.g., a gene encoding a glycolytic enzyme, beta actin, or a structural protein etc.)

In another embodiment, at least 25% of the different nucleic acids affixed to the solid support hybridize at least to a portion of an RNA transcript from a different intrinsic reporter of cell signaling. In a preferred embodiment, at least 50% of the different nucleic acids affixed to the solid support hybridize at least to a portion of an RNA transcript from a different intrinsic reporter of cell signaling. In a more preferred embodiment, at least 80% of the different nucleic acids affixed to the solid support hybridize at least to a portion of an RNA transcript from a different intrinsic reporter of cell signaling. In an even more preferred embodiment, the different intrinsic reporters of cell signaling include those identified in the list of Table 1 or an ortholog thereof.

In one such embodiment, at least 80% of the different nucleic acids affixed to the solid support hybridize at least to a portion of an RNA transcript from a gene identified in the list in Table 1 (represented by the GenBank accession numbers) or an ortholog thereof. More preferably, at least 90-95% of the different nucleic acids affixed to the solid support hybridize at least to a portion of an RNA transcript from a gene listed in Table 1 or an ortholog thereof. In a particular embodiment, all of the different nucleic acids affixed to the solid support hybridize at least to a portion of an RNA transcript from a gene listed in Table 1 or an ortholog thereof. In a preferred embodiment, the solid substrate comprises at least two copies of each different affixed nucleic acid. More preferably, the solid substrate comprises at least three copies of each different affixed nucleic acid.

In a related embodiment, the solid substrate comprises 25 to 5000 different nucleic acids each coupled (e.g., affixed) to the solid substrate in a different/separate known location, and RNA transcripts from at least 80% of the intrinsic reporter of cell signaling listed in Table 1 or of the orthologs thereof, can hybridize with specificity with the affixed nucleic acids. More preferably, RNA transcripts from at least 90-95% of the intrinsic reporter of cell signaling listed in Table 1 or of the orthologs thereof, can hybridize with specificity with the affixed nucleic acids. In a preferred embodiment, the solid substrate comprises at least two copies of each different affixed nucleic acid. More preferably, the solid substrate comprises at least three copies of each different affixed nucleic acid.

The present invention also provides methods of identifying a gene that is modulated (either up-regulated or down-regulated) by a given agent or multiple agents. One such embodiment comprises contacting the agent with a cell for a time period sufficient to allow transcription of a gene to generate an RNA, and then isolating the RNA from the cell. An isolated RNA preparation is thereby obtained which comprises individual RNA transcripts generated by the cell. The isolated RNA preparation is hybridized to a plurality of different nucleic acids affixed to a solid substrate in which each different nucleic acid has been affixed to the solid substrate in a different/separate known location. The hybridization is performed with sufficient specificity for an individual RNA transcript (or corresponding cRNA or cDNA) of the isolated RNA preparation to hybridize to a specific affixed nucleic acid. This allows the subsequent determination of RNA transcripts that have increased or alternatively decreased in amount in the presence of the agent relative to in the absence of the agent. Preferably this determination is performed in conjunction with statistical analysis. When the amount of the individual RNA transcript has changed in a statistically significant manner in the presence of the agent relative to in its absence, a gene that is modulated by the agent is identified. In a preferred embodiment of this type, the modulation corresponds to an up-regulation.

The present invention also includes a method for calibrating the degree of change observed for the genes measured by being affixed to solid substrates. The ratio of gene levels obtained with two samples can be corrected by the calibration function $Fc=Fa^q$, where Fa is the microarray-determined fold-change, q=is the correction factor and Fc is the corrected value. In one embodiment, Fc is determined by assaying a selected number of genes for determination of reference values by real-time PCR or similar quantitative method. In this embodiment:

$$Fc=Fa^q$$

where $$q = \frac{\sum \log Fp}{\sum \log Fa}$$

In a particular embodiment of this type q=1.4.

Other methods of identifying genes that are up-regulated by an agent are also provided by the present invention. One such method comprises contacting an agent with a cell that preferably comprises a set of genes that includes at least 80% of the intrinsic reporter of cell signaling listed in Table 1, or orthologs thereof for a time period sufficient to allow transcription of a gene to generate an RNA. The individual relative levels of expression are then determined and the genes within the set of genes that have an increased relative level of expression in the presence of the agent relative to in the absence of the agent are identified. These identified genes have an increased relative level of expression in the presence of the agent and are thereby genes that are up-regulated by the agent.

In a preferred embodiment, the method further comprises the step of isolating RNA from the cell following the contacting step but prior to the determining step, whereby an isolated RNA preparation is obtained which comprises individual RNA transcripts generated by the cell. In a particular embodiment of this type, determining an increased relative level of expression in the presence of the agent relative to in its absence is performed by quantifying the amount of RNA and/or rate of transcription of the RNA of the particular early response gene. In one embodiment, the determining is performed by hybridization. In another embodiment, the determination is performed by one of the various techniques using continuous detection of fluorescence during PCR. These include but are not limited to: (a) SYBR® green dye based detection, (b) Taq man assays (c) molecular beacon assays and (d) hybridization probes. In yet another embodiment, the determination is performed using competitive polymerase chain reaction. In still another embodiment, the determination is performed by a Northern blot. In yet another embodiment, the determination is performed by quantitative nuclease protection assay preferably using either RNAse or S1 nuclease. In still another embodiment, dot blot or slot blot analysis is used.

In a preferred embodiment of this type, the determination of the amount of RNA (and/or rate of RNA transcription) is performed by hybridizing the isolated RNA preparation with a set of 50 to 500 different nucleic acids that are coupled to a solid substrate in different/separate known locations. Preferably, at least 50% of the different nucleic acids of the set of nucleic acids hybridizes with specificity to at least a portion of an RNA transcript from an early response gene. In a preferred embodiment of this type, each different nucleic acid is contained at least in triplicate on the solid substrate.

Another embodiment of the method further comprises performing Real-time PCR for the genes identified by hybridization with the solid substrate and then determining the cycle at which the PCR product exceeds baseline. A gene is then identified to have an increased relative level of expression in the presence of the agent relative to in its absence when the amount of and/or rate of PCR product determined increases. In still another preferred embodiment of the present invention, the method comprises utilizing SYBR® green real-time PCR.

In related embodiments, any of the quantitative RNA assays listed herein are used to quantify the changes in the level of the group of early genes listed in Table 1 or orthologs, without first using the solid substrate assay. In a preferred embodiment of the present invention, the method comprises utilizing SYBR® green real-time PCR without first using the solid substrate assay.

Preferably, a method of the present invention also includes a cut-off point for the amount of increase in level of RNA expression that is considered significant enough to identify a gene as being up-regulated. In a preferred embodiment, genes that are identified as having an increased relative level of expression in the presence of the agent must have an increase of 1.3 fold or greater relative to that determined in the absence of the agent. In a more preferred embodiment, genes that are identified as having an increased relative level of expression in the presence of the agent must have an increase of 1.5 fold or greater relative to that determined in the absence of the agent.

In addition, since this aspect of the present invention concerns the up-regulation of intrinsic reporters of cell signaling of signal transduction pathways, the period of time after the initial contacting of an agent with a cell (either in situ, in vitro, ex vivo or in vivo) to the time that RNA transcription is no longer being monitored can be critical. For this aspect of the invention, this time is meant to correspond to the time between the initial contacting of the agent with the cell (e.g., a receptor on the cell surface) and the transcription of the first genes (i.e., intrinsic reporters of cell signaling) in the signal transduction pathway, i.e., prior to significant subsequent transcription of genes that are induced by a gene product of the intrinsic reporters of cell signaling. In a particular embodiment of this type, when the corresponding cell is incubated at about 37° C., the time that the RNA transcription is measured is approximately 30 minutes to 2 hours, preferably 45 minutes to 1.5 hours, and more preferably approximately 1 hour. In a preferred embodiment, the transcription of the genes is assayed at a time point determined empirically to represent a linear accumulation phase, (as illustrated in the Examples below).

Moreover, since the methods of the present invention depend on a reliable determination of the quantity and/or rate of RNA transcribed, in a preferred embodiment such determinations include the use of a data analysis algorithm. A preferred form of such an algorithm is provided in the Examples below.

The present invention further provides methods of determining the concentration dependence and/or the time dependence of an agent on the signal transduction pathways of a cell. Any of the methodologies described herein can be used in these determinations including prior to, in conjunction with and following such determinations. Preferably, multiple concentrations of an agent are contacted with the cells for multiple times of incubation, and the individual rate of transcription and/or the amount of transcription of a given set of genes is determined. The genes within the set of genes that have an increased relative level of expression in the presence of the agent relative to in the absence of the agent are identified at each time and each concentration. The up-regulation of the genes is thus characterized in terms of an increased relative level of expression in the presence of the agent at multiple times and multiple concentrations.

The present invention therefore permits the identification of agents (preferably small organic molecules) that have the same or similar properties relative to their effect on signal transduction pathways as either a known agent or a desired agent. In addition, the agents identified by the methodology of the present invention can be used in place of a larger more cumbersome agent (e.g., in place of insulin for treatment of diabetes) or in place of another agent that has a number of positive features, but one or more undesirable side-effects (e.g., thalidomide for treatment in AIDS, tuberculosis or leprosy). In the latter case, the agent identified by the present invention would preferably be identified as not having one or more of the undesirable side-effects. Furthermore, lead compounds could be tested by the methodology disclosed herein for the likelihood of having an undesirable side-effect, preferably early in the drug identification process.

In one aspect of the present invention, methods are provided for selecting a candidate compound that has attributes that are superior to a reference compound that has a known desirable and/or undesirable activity. One such method comprises contacting a compound with a cell, cell line, tissue, portion of a tissue and/or an animal subject for a time period sufficient to allow transcription of a group of selected intrinsic reporters of cell signaling (IRCs) to generate RNAs. The EC50 and/or maximal response for each selected IRC in the presence of the compound is determined for each IRC selected. These results are then compared with the corresponding EC50 and/or maximal responses determined for each IRC in the presence of one or more reference compounds. The candidate compound is selected when it is determined to be more desirable than the reference compound. In a particular embodiment of this type the reference compound is a toxic compound and the candidate compound is determined not to be toxic. These assays may be performed by any of a number of methods including by a microarray, a dot blot hybridization, a slot blot hybridization, a Real-time PCR using SYBR® Green detection, a Real-time PCR using TaqMan assay, a Real-time PCR using hybridization probes, a Real-time PCR using molecular beacons, a quantitative competitive PCR, a northern blot analysis, a RNase nuclease protection assay and a S1 nuclease protection assay. The animal subject can be either an invertebrate or a vertebrate. Any vertebrate can be used including mammals such as rodents (e.g., mice, rabbits, or rats), cats, dogs, lower primates (e.g., monkeys) or higher primates such the great apes and humans.

In a preferred embodiment, the method of comparing the candidate compounds with the reference compounds is performed by calculating the Euclidean distances between the EC50 and/or maximal responses of the candidate compound and those of the reference compound that have been plotted in multidimensional space or using a similarity matrix. The results of an IRC analysis of a particular compound can be represented as a multidimensional vector where each separate EC50 and maximal response determination for each IRC evaluated represents a separate dimension of the vector. Thus, the difference between any two chemicals profiled can be determined by calculating the Euclidean distance between the vectors obtained for each chemical. In a particular embodiment, an optimum time point for assaying the IRCs is determined empirically by testing multiple time points. In one such embodiment, the optimal time point is determined from characterizing the responses observed between 20 minutes and 2 hours. In another embodiment, the accuracy of the measurements of IRCs or other genes obtained from a microarray is improved by the use of a calibration function. Preferably multiple concentrations of the candidate compound(s) and the reference compound(s) are tested.

Commercial test kits that rely on the methodology of the present invention and that are suitable for testing potential drugs are also provided. In addition, the agents identified by the methodology of the present invention are also provided by the present invention.

Accordingly, it is a principal object of the present invention to provide methodology to identify potential drugs that can be used to modulate conditions e.g., diseases such as diabetes, cancer, neuropsychiatric disorders (including depressive disorders, anxiety, sleep disorders, cognitive disorders, movement disorders, schizophrenia and substance abuse disorders), chronic and acute pain, and gastrointestinal disorders, including diarrhea, that are due to the mal-functioning of one or more signal transduction pathways, that can be controlled by modulating specific signaling pathways or that can be treated more efficaciously by the identification of novel agents lacking side-effects that limit the use of present-generation drugs.

These and other aspects of the present invention will be better appreciated by reference to the following drawings and Detailed Description.

BRIEF DESCRIPTION OF THE DRAWINGS

FIG. 1A is representative "good" data samples. The plot is linear and scatter is limited (r2=0.98) FIG. 1B is a "poor" regression. Data was generated using RNA samples from HEK293 cells and Affymetrix U95A oligonucleotide arrays.

FIG. 2A is the amplification plots obtained. FIG. 2B is a plot of threshold cycle against cDNA copy number. The large linear range of the assay is evident.

FIG. 3A shows the level of egr-3 gene expression after one hour of treatment determined by real-time PCR. The data were analyzed by non-linear regression. FIG. 3B shows for comparison, an inositol phosphate-concentration response curve in the same cell line. Accumulation of [H]3-inositol phosphates was determined as previously described by Almaula et al. (1996) J. Biol. Chem. 271:14672-14675).

DETAILED DESCRIPTION OF THE INVENTION

Figure 1:
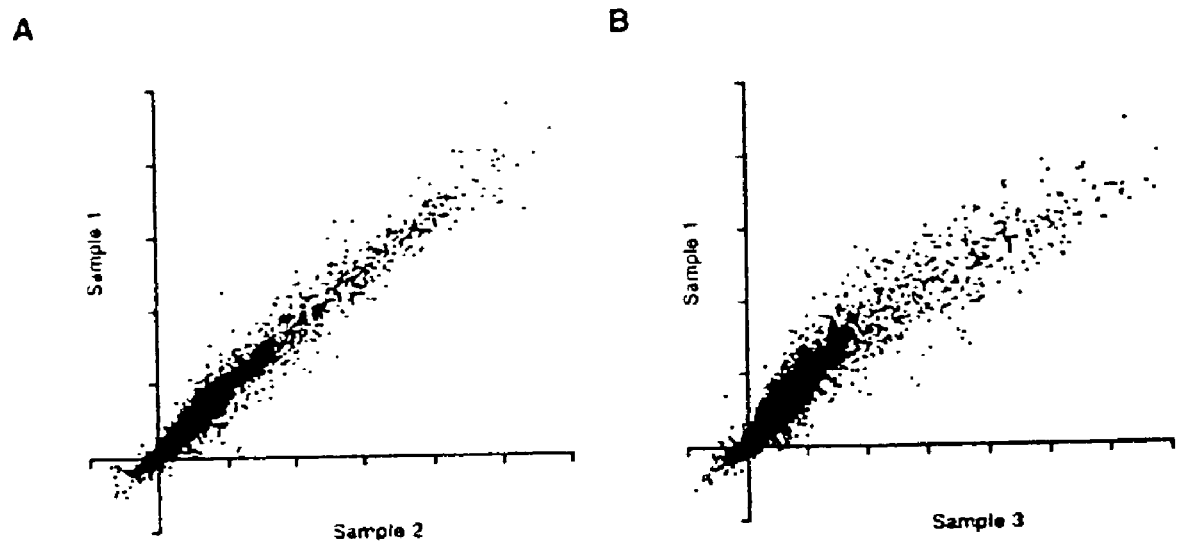
FIGS. 1A-1B show the regression analysis of microarray data. All gene cluster measurements are compared in two samples.

Quantifying changes in the expression of specific genes has the potential to provide a sensitive and global profile of the physiological changes that occur in a cell in response to a specific stimulus, such as activation of a cell surface receptor. This use of transcript level profiling can be understood by analogy with gene reporter assays. Gene reporter assays, such as a promoter containing an NFkappaB reponse element linked to a reporter gene such as luciferase, show a concentration dependent increase in activity following receptor activation when the receptor is coupled to a pathway that stimulates signaling that activates the reporter construct (Klein et al. (2000) Ann. Neurol. 47(3):369-373). By analogy, the cell's own promoters and genes can provide a readout of the activity in various signal transduction pathways in the cell. Use of this approach requires the identification of the class of genes that are rapidly responsive to changes in cellular signal transduction.

The present invention therefore provides methods for detecting and/or quantifying alterations of the transcription of specific genes in a cell. More particularly, the present invention provides methods of correlating a change in the relative levels of expression of specific genes in a cell with the binding of a given ligand (e.g., an agonist) to a receptor. Preferably, this ligand-receptor binding complex initializes one or more signal transduction pathways. More preferably, the specific genes are intrinsic reporters of cell signaling, e.g., genes identified to show a statistically significant increase of 1.3-fold or greater within one hour of exposure to a cell or tissue to a chemical. Indeed, the present invention identifies specific RNA transcripts that can act as intrinsic reporters of cell signaling (IRC) because of their capacity to reflect activation of a given signal transduction pathway.

In a related aspect of the invention a methodology is provided in which specific genes are pre-selected and then repeatedly printed on a microarray. This methodology, as disclosed herein, is termed focused microarray analysis (FMA). Although FMA provides less broad transcriptome coverage than a global array, this limitation can be partially overcome by the careful selection of which clones are represented. Indeed, FMA facilitates the generation of high quality experiments and is sensitive to small, regulatory changes that can be confirmed by independent measurements.

The use of these two related aspects of the invention is exemplified below (Example 2). Thus, genes that are regulated immediately following gonadotropin releasing hormone (GnRH) receptor activation were examined using an early response gene cDNA microarray of the present invention. 956 candidate genes were carefully selected for the microarray and the response to GnRH in a time course from 1-6 hours (h) was determined. Triplicate measurements on each array and a t-statistic-based regulation algorithm were used for data analysis. Measurements were highly reproducible within arrays, between arrays and between experiments. Data quality and algorithm reliability were assessed with 5400 real time PCR assays of 60 genes. Gene changes on the microarray as low as 1.3 fold were confirmed by real-time PCR. These data demonstrate the reliability and accuracy of focused microarray analysis (FMA). All of the 23 regulated genes identified were elevated at 1 hour and most returned to baseline by 3 hours.

In a particular embodiment, two samples of cells are incubated for a selected period of time (e.g., 1 hour at 37° C.). The "test" sample of cells is incubated in medium that contains an agent being tested, whereas the "control sample" is incubated in medium that does not contain the agent. The total RNA is then extracted from the two cell samples. Reverse transcription is then performed on the "test" and "control" mRNA samples yielding the corresponding "test" cDNAs and "control" cDNAs in a manner that causes the "test" cDNAs to be labeled with one fluorescent probe and the "control" cDNA to be labeled with another fluorescent probe. The fluorescent probes should be distinguishable (i.e., having different excitation and/or emission spectra and preferably having both different excitation and emission spectra). The "test" cDNAs and "control" cDNAs are then placed on a solid substrate of the present invention (e.g., a microarray) thereby hybridizing with the affixed nucleic acids. After washing off the non-hybridized cDNAs, the fluorescence of the probes of the hybridized cDNAs is determined. The "control" cDNAs thereby can serve as an internal standard. Therefore, the fold-increase or decrease in the transcription of a given gene can be determined in terms of the ratio of fluorescence due to the "test" probe and the "control" probe on the solid substrate.

The present invention further provides methods of quantifying the levels of transcription of selected genes (including selected intrinsic reporters of cell signaling) in a cell following the exposure of the cell, cell line, tissue, portion thereof, or an animal subject to an agent. Such methods can be used to quantify the levels of each selected gene (e.g., intrinsic reporters of cell signaling with control genes) in a cell, in response to a series of concentrations of a given agent and/or at different time points following the administration of the agent to the cell, cell line, tissue, portion thereof, or an animal subject. Such quantifying includes constructing a landscape as described in Example 6, below. Thus, the present invention further provides methods for determining the responses of various concentrations of an agent or group of agents for each IRC selected in a target following the exposure of the cell, cell line, tissue, portion thereof, or an animal subject to the agent or group of agents. In a preferred embodiment an optimum time point(s) for assaying the IRCs is determined empirically from characterizing the responses observed between 20 minutes and 2 h.

In addition, the methods can include determining the EC50 and maximal response for each IRC selected in a target cell, cell line, tissue, portion thereof, or an animal subject for a group of reference compounds, which have either desirable or undesirable effects, or both. Thus, the potential beneficial and/or undesirable activities of the agent (e.g., a candidate compound) are determined relative to known reference compounds. Of course, certain effects such as cell toxicity can be beneficial (such as in cancer treatment) or undesirable (such as a side-effect of an otherwise useful treatment). Thus by comparing the effects/responses of a cell etc. to an agent or agents (e.g., candidate compounds) with those obtained for the reference compounds, the potential beneficial and/or undesirable activities of a candidate compound can be determined. Indeed, a candidate compound or candidate compounds can be selected for its ability to stimulate the transcription of the genes known to be beneficial (from e.g., a survey of reference compounds) and/or for its ability not to stimulate the transcription of the genes known to be detrimental (e.g., to screen for compounds without undesirable side effects). In a particular embodiment, the comparison between candidate compounds and reference compounds is determined by calculating the Euclidean distances between the effects of the responses of the candidate compounds and reference compounds plotted in multidimensional space and/or using a similarity matrix. Preferably the accuracy of the measurements of IRCs or other genes obtained from cDNA microarrays is improved by the use of a calibration function.

DEFINITIONS

As used herein, an "intrinsic reporter of cell signaling" is a gene that has been reported to show a reproducible increase in the RNA level transcribed from that gene (greater than 1.3 fold, preferably greater than 1.5 fold) by 1 hour after exposure to a stimulus at 37° C. in a cellular system or in a particular tissue by one hour after exposure to an animal in vivo. Intrinsic reporters of cell signaling are defined by their unique capacity to show a response under these conditions. Once a gene has met this criterion in a cell system or in vivo experimental system, it is an established intrinsic reporter of cell signaling. As an intrinsic reporter of cell signaling will not always show a significant increase in all cells or in all experimental systems, the failure to show a response does not exclude its identification as an intrinsic reporter of cell signaling. A non-inclusive list of intrinsic reporters of cell signaling is provided in Table I.

As used herein, an "ortholog" of an RNA from one species is an RNA of another species in which its respective full length cDNA shows an 80% nucleotide sequence identity or greater for a segment consisting of greater than 100 continuous nucleotides and can be identified by hybridizing under stringent hybridization conditions, defined as 2xPipes, 50% formamide, 0.5% SDS, 100 µg/ml herring sperm DNA at 42° C. followed by washing with 0.2xSSC, 0.1% SDS at 60° C.

As used herein, an "RNA transcript" is an RNA that has been transcribed from a gene. An RNA transcript can include the coding sequence of the protein encoded by the gene, and the 5' and 3' untranslated sequences. The RNA transcript can also be a polyadenylated RNA. For the methodology of the present invention it is preferred that the RNA transcript comprises the 3' untranslated sequence whether all or just a portion of the coding sequence is present or not.

As used herein, a "gene probe" is nucleotide sequence that allows the measurement of the level of a specific RNA transcript. When a gene probe is used with a solid substrate to hybridize to the specific RNA transcript the gene probe is preferably 40 or more nucleotides.

As used herein, a "small organic molecule" is an organic compound [or organic compound complexed with an inorganic compound (e.g., metal)] that has a molecular weight of less than 3 kilodaltons, and preferably less than 1.5 kilodaltons. A "compound" of the present invention is preferably a small organic molecule.

As used herein, the terms "solid substrate" and "solid support" are used interchangeably and represent a solid material that provides an inert surface that allows a biological reaction to be performed. Solid supports include biological chip plates as exemplified by Rava et al., U.S. Pat. No. 5,874,219, the contents of which are herein specifically incorporated by reference in its entirety, and multi-well (multi-titer) quartz and polystyrene plates. Examples of material that can be used as solid substrates include glass, peptide polymers (e.g., collagen), peptoid polymers, polysaccharides (including commercial beads, e.g., SEPHADEX and the like), carbohydrates, hydrophobic polymers, polymers, tissue culture polystyrene, metals, derivatized plastic films, glass beads, plastic beads, alumina gels, magnetic beads, nitrocellulose, cellulose, and nylon membranes.

As used herein, the term "container" is used to indicate a solid substrate or support" that provides surface for a cell to grow and/or differentiate and/or allows for a volume of liquid to cover or contain the cell. Preferably the containers are made from glass or a plastic. Particular examples of solid supports used herein are laboratory flasks, petri dishes and glass slides, i.e., the types of containers used in standard tissue culture procedures.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook and Russell, *Molecular Cloning A Laboratory Manual*, third addition Cold Spring Harbor Laboratory Press, Cold Spring Harbor N.Y. (2001)]. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ are known whereas for hybridization with shorter nucleic acids, i.e., oligonucleotides, the position of mismatches becomes more important, and the length of the oligonucleotide determines its specificity. Preferably a minimum length for a hybridizable nucleic acid is at least about 18 nucleotides; preferably at least about 40 nucleotides; and more preferably the length is at least about 48 nucleotides. More specific hybridization conditions and primer lengths are exemplified above and in the Examples below.

As used herein, the phrase "contacting an agent with a cell" can refer to direct exposure of the agent to the cell, such as adding the agent to cells growing in tissue culture, and/or to indirect exposure of the cell to the agent, such as injecting or feeding an animal with the agent in order to bring the test cell, such as a liver or kidney cell, into contact with the agent.

Use of Intrinsic Reporters of Cell Signaling

The monitoring afforded by measurement of a series of Intrinsic Reporters of Cell Signaling (IRCs) can be understood by analogy to the responses observed with extrinsic reporter molecules. Extrinsic signal transduction reporter construcsts consist of gene promoters or nuclear protein binding elements that drive reporter genes. Examples include a CRE-β-galactosidase construct or an NFκ-β-luciferase construct.

Extrinsic reporter constructs are recognized as a useful means for efficiently monitoring the signal transduction events following receptor activation in cell lines. While reporter constructs usually respond to more than one signaling pathway, specific constructs respond differently. Therefore, the measurement of multiple reporter constructs allows a sampling of the activation of different signaling pathways. Thus a particular reporter shows clear differences in its response to different signaling pathways. Monitoring multiple reporters that differ in their sensitivity to various signal transduction pathways can provide insight into the relative activation of these pathways. While a given gene reporter does not map precisely to a single G-protein or signal transduction pathway, a panel of reporters can provide a matrix that reflects the pattern of second messenger activation in the cell.

While gene reporter constructs can be introduced into tissue culture cells and even into tissues (e.g. neurons) in vivo via transgenic technology, it would be particularly cumbersome to monitor a group of reporter constructs, especially in vivo. Because multiplex reporter monitoring is necessary to sample different signal transduction events in the cell, assaying intrinsic reporter molecules has clear advantages. All cells express various intrinsic reporters that can serve a signal transduction reporting function similar to that of reporter constructs. The IRCs identified below as a group are the family of early genes, such as Arc, fos and Zif268 Many IRCs integrate more than one signaling pathway. However, in a liven cell, different IRCs vary considerably in their response to specific signaling pathways. The pattern of activation of individual immediate early genes has been found to vary considerably depending on the signaling pathway that is activated. Thus, a selection of several IRCs can provide a sampling that reflects the relative activation of different signal transduction pathways.

In addition, as is readily apparent, any cell, tissue or organism can be used with the methodology of the present invention. Several cell lines are specifically described in the Examples below, but this should in no way imply that only cell lines can be employed since essentially any cell is amenable to the methodology of the present invention. Thus, the present invention can be used to study the responses observed in tissues, such as brain, liver and kidney, of whole animal subjects, such as experimental rats or mice etc, that are exposed to the agents that are to be evaluated.

The IRCs exemplified by the present invention represent genes that activate rapidly in response to second messenger activation, for example c-fos, zif-268 and nurr-77. Furthermore, unlike the approaches presently taken in which such markers are used to either identify the gene program activated in a cell following a particular stimulus or alternatively, to identify cells in a particular tissue that responds to a particular effector, the methodology of the present invention employs IRCs to indirectly monitor the pattern of second messenger signal transduction activation in the cell.

Individual IRCs may differ in their responses to specific cell signals, the pathway selectivity is not absolute and, when using IRCs in vivo, the differences in responses to specific signaling pathways may not be known in a given cell. Importantly, the measurement of the responses of several IRCs in a given cell can provide an assay that reflects the relative activation of different signaling pathways, even though the precise signaling events being monitored may not be identified a priori for a given panel of IRCs.

Methods of Obtaining Candidate Compounds

An agent of the present invention, e.g., a candidate compound, can be obtained by a number of means, including from a commercially available chemical library or an "in house" pharmaceutical library Examples of libraries of compounds that are commercially available include the Available Chemicals Directory (ACD.) the Specs and BioSpecs database, the Maybridge database, and the Chembridge database.

Alternatively, screening compounds can also be synthesized de novo either individually or as combinatorial libraries (Gordon et at. (1994) J. Med. Chem. 37:1385-1401) They may also be obtained from phage libraries. Phage libraries have been constructed which when infected into host E. coli produce random peptide sequences of approximately 10 to 15 amino acids. Once a phage encoding a peptide that can act as a potential drug has been purified, the sequence of the peptide contained within the phage can be determined by standard DNA sequencing techniques. Once the DNA sequence is known, synthetic peptides can be generated which are encoded by these sequences.

If the three-dimensional structure of a particular polypeptide and/or nucleic acid has been determined, potential binding partners (e.g., inhibitors) can be examined through the use of computer modeling using a docking program such as DOCK, GRAM, or AUTODOCK (Dunbrack et at. (1997) Folding & Design 2:27-42). This procedure can include computer fitting of potential binding partners to the protein to ascertain how well the shape and the chemical structure of the potential binding partner will bind to the protein (Bugg et al. (1993) Scientific American, December:92-98; West et al. (1995) TIPS 16:67-74). Computer programs can also be employed to estimate the attraction, repulsion, and steric hindrance of the protein with a potential binding partner.

Generally, the greater the steric complementarity and the greater the attractive forces, the more potent the potential inhibitor since these properties are consistent with a tighter binding constant. Furthermore, the more specificity in the design of a potential inhibitor, the more likely that the drug will not interact as well with other proteins. This will minimize potential side-effects due to unwanted interactions with other proteins.

Typically known binding partners of the protein are chosen as good starting points for the modeling process. Systematic modification of selected binding partners by computer modeling programs can then be performed until one or more potential binding partners are identified. Such analysis has been shown to be effective in the development of HIV protease inhibitors (see, for example, Lam et al. (1994) Science 263:380-384). For example, Selzer et al. 1997) Exp Parasitol. 87(3):212-221) screened the Available Chemicals Directory (a database of about 150,000 commercially available compounds) for potential cysteine protease inhibitors, using DOCK3.5. Based on both steric and force field considerations, they selected 69 compounds Of these, three had IC50's below 50 μM. The effective compound(s) can then be synthesized in large quantities Such compounds can then be further tested in assays as disclosed herein in order to further determine their suitability for the desired task.

A list of intrinsic reporters of cell signaling is provided in Table 1. The identity of the RNA species representing each early response gene is indicated by an accession number in at least one species, human, mouse or rat. There is no standardization of the names of these genes. A brief working name and description are included where available. EST refers to expressed sequence tag. The accession numbers of the cDNA clones are listed in Table 1 solely to identify the corresponding genes from which they were derived. Thus, the cDNAs and accession numbers listed in Table 1 are merely representative cDNA clones of the intrinsic reporters of cell signaling identified. Therefore, any cDNA corresponding to any exon or identifiable fragment thereof of any gene identified by the cDNAs and accession numbers listed in Table 1 may be used in the methods and/or be part of the compositions of the present invention. Further identification of a given cDNA sequence as being a fragment of a particular early response gene identified by a single cDNA and its accession number in Table 1 can be readily determined by analysis of gene databases such as the public database. Medline, using standard analysis tools such as the BLAST algorithm or reference to the "builds" of the genes indicated.

Kits

In a further embodiment of this invention, commercial test kits suitable for testing potential drugs are provided. In accordance with the testing techniques discussed above, one class of such kits will contain primers necessary for defining a subset of IRCs that can be used to generate a response landscape. In a particular embodiment, primers for at least eight intrinsic reporters of cell signaling are included. In a preferred embodiment, 1-5 or more primers for housekeeping genes (e.g., β-actin, cyclophilin, etc.) are included. In another embodiment 50-100% of the genes identified in Table 1 are provided.

A kit of the present invention also preferably contains directions and/or reagents for protocols that depend upon the method of detection selected, e.g. a dot blot hybridization, a slot blot hybridization, a Real-time PCR using SYBR® Green detection, a Real-time PCR using TaqMan assay, a Real-time PCR using hybridization probes, a Real-time PCR using molecular beacons, a quantitative competitive PCR, a northern blot analysis, a RNase nuclease protection assay and/or a S1 nuclease protection assay are included. The kits of the present invention may also contain peripheral reagents such as buffers, stabilizers, etc.

Specific Embodiments

Example 1 illustrates the use of microarray and quantitative real-time PCR to sample the overall gene response pattern. The overall approach to the study of cell signaling is summarized in Table 4. Cell lines are used that either endogenously express or are stably transfected with the receptor to be studied

TABLE 4

OVERVIEW OF INTRINSIC REPORTER OF CELL SIGNALING (IRC) ASSAY

A. Selection of candidate IRCs

1. RNA preparation for microarray screening
2. Sample validation
3. Microarray labeling and hybridization:
4. Data validation
5. Statistical Analysis B. Determine Response of IRCs 1. Oligonucleotide design for real-time PCR assays
2. RNA extraction and reverse transcription for PCR
3. Real time PCR Example 2 describes a focused microarray analysis of GnRHR-coupled gene network organization. Although microarrays have become widely used, generally accepted standards for data reproducibility and reliability have not been established. The controllable sources of error in microarray experiments include the biological procedure, RNA isolation, labeling method, microarray fabrication, hybridization technique and analysis algorithm. In developing the intrinsic reporter of cell signaling array, several aspects of the experimental design and analysis to confirm data quality were relied on. Printing and attachment conditions were optimized. All genes are preferentially spotted in triplicate, which facilitates the identification of regulated genes and the exclusion of artifacts and allows statistics to be calculated for each array, cDNA identification was more than 90% accurate and 100% of amplified clones were detectable by test hybridization on the array. These data indicate a high level of microarray fabrication accuracy (see Knight (2001) supra; Taylor et al. (2001) Biotechniques 31:34-39).

The hybridizations were uniform and a low median coefficient of variation were found for all triplicate assays within each slide. The measurements were reproducible within slides, between slides and between experiments. Regulated genes for which two clones were spotted on the array shorted nearly identical changes, indicating that the changes observed were independent of array position. In the experimental cell line tissue culture system, the biological variability between samples is low and does not appreciably increase the variance observed between separate arrays. Indeed, the results reflect a high level of error reduction throughout all aspects of the array development, experiments and assays.

The scatter plots of the array data showed a dense linear alignment of those transcripts that were not significantly regulated. The changes in expression observed were demonstrated on separate arrays representing independent experiments. The early gene transcripts known to be regulated by GnRH in gonadotropes, including Egr1 (Tremblay and Drouin (1999) Mol. Cell Biol. 19:2567-2576), c-fos (Abbas and Evans (2000) Neuroendocrinology 71:292-300; Cheng et al. (2000) Endocrinology 141:3611-3622) and c-jun (Cheng et al. (2000) supra), were correctly identified in our microarray data.

The ultimate assessment of the experimental procedures and microarray data was provided by independent determination of the levels of 60 transcripts by real-time PCR. These assays confirmed the regulation of nearly all transcripts that met the criteria for significant regulation on the array (Table 2). Three genes which did not meet the criteria on the microarray were found to be regulated when tested by real-time PCR (STY kinase 1.7-fold, SCL 2.4-fold, and glucose transport protein 2.2-fold). On the other hand, 3 genes which were found to be slightly regulated on the microarray, did not reach the same 1.3-fold change criterion when assayed by real-time PCR. For these three genes which are nominally discrepant according to the cutoff, the actual fold-change measurements were relatively close. Thus the microarray analysis was able to successfully identify several truly but only slightly regulated genes (e.g. Nrf2, MKP1, transgelin) at the cost of very few false positive results. Egr2, which was significantly but only slightly regulated on the microarray, was found to be very highly regulated by real-time PCR. The sensitivity of the microarray to regulation of a particular transcript may be influenced by errors in clone identification, by non-specific hybridization of the target sequence and by target location within the gene. With the exception of genes that are very highly regulated (>20-fold by real-time PCR), the fold-change measurements obtained by the microarray are closely correlated with the real-time PCR results ($r=0.87$). Within this dynamic range, FMA provides a reasonable estimate of both the identify and magnitude of gene induction.

Conventional assays of signal transduction often do not provide an explanation for the strikingly different activities of different agents that activate the same receptors. One class of compounds that illustrates this phenomenon consists of the serotonergic hallucinogens. Thus, compounds, such as LSD and DOI are believed to cause their psychological and neurobiological effects via interaction with the 5-HT2A receptors. However other related compounds that interact with this receptor do not cause similar effects. As demonstrated in Example 3, the activity of the hallucinogen DOI and the native neurotransmitter 5-hydroxytryptamine (5-HT) at the cloned human 5-HT2A receptor are distinguished by profiling the intrinsic reporters of cell signaling (IRC) responses to different concentrations of these agents. The IRC responses assayed can be assembled into a signaling landscape that represents the pattern of response to each agent.

Determining the toxic effects of drug candidates can be achieved using IRCs by comparing the concentration-dependent pattern of the response obtained in a test cell line or target tissue with that observed in response to agents of known toxicity in that test cell line or target tissue. The activation of IRCs by a known toxin in the rat neuronal cell line PC12 is demonstrated in Example 4 below. Example 5 shows how the proper time point or time points after exposure can be determined experimentally in any system by performing a time course of the gene response.

In Example 6, the accuracy of microarray measurements obtained using oligonucleotide arrays were compared (GENECHIP, Affymetrix) with the FMA described. Sets of test mRNA samples were obtained from the exposure of a gonadotrope cell line to GnRH, a biological interaction that regulates the transcription of many genes assayed on both arrays. The two microarray approaches examined (i) were optimized, (ii) reference measurements were generated in the test mRNA samples using quantitative real-time PCR assays, and (iii) 51 genes were identified that there represented on both arrays. The accuracy of the fold-change (F) measurements obtained for each approach was assessed by determining the measurement bias. Both platforms tend to significantly underestimate the relative changes in mRNA expression between samples. The bias observed with cDNA arrays was predictable for F<32-fold and could be corrected by the calibration function $Fc = Fa^q$, where:
Fa is the microarray-determined fold-change,
q is the correction factor (empirically determined to be 1.4 in our system), and
Fc is the corrected value.

The bias observed with the commercial oligonucleotide arrays was less predictable and their calibration was unsuccessful. Following calibration, measurements generated by the custom cDNA array disclosed herein were more accurate than those obtained by the commercial oligonucleotide array. Microarray measurements show systematic bias and the use of this calibration function markedly improves the accuracy of data obtained using cDNA arrays.

Figure 15:
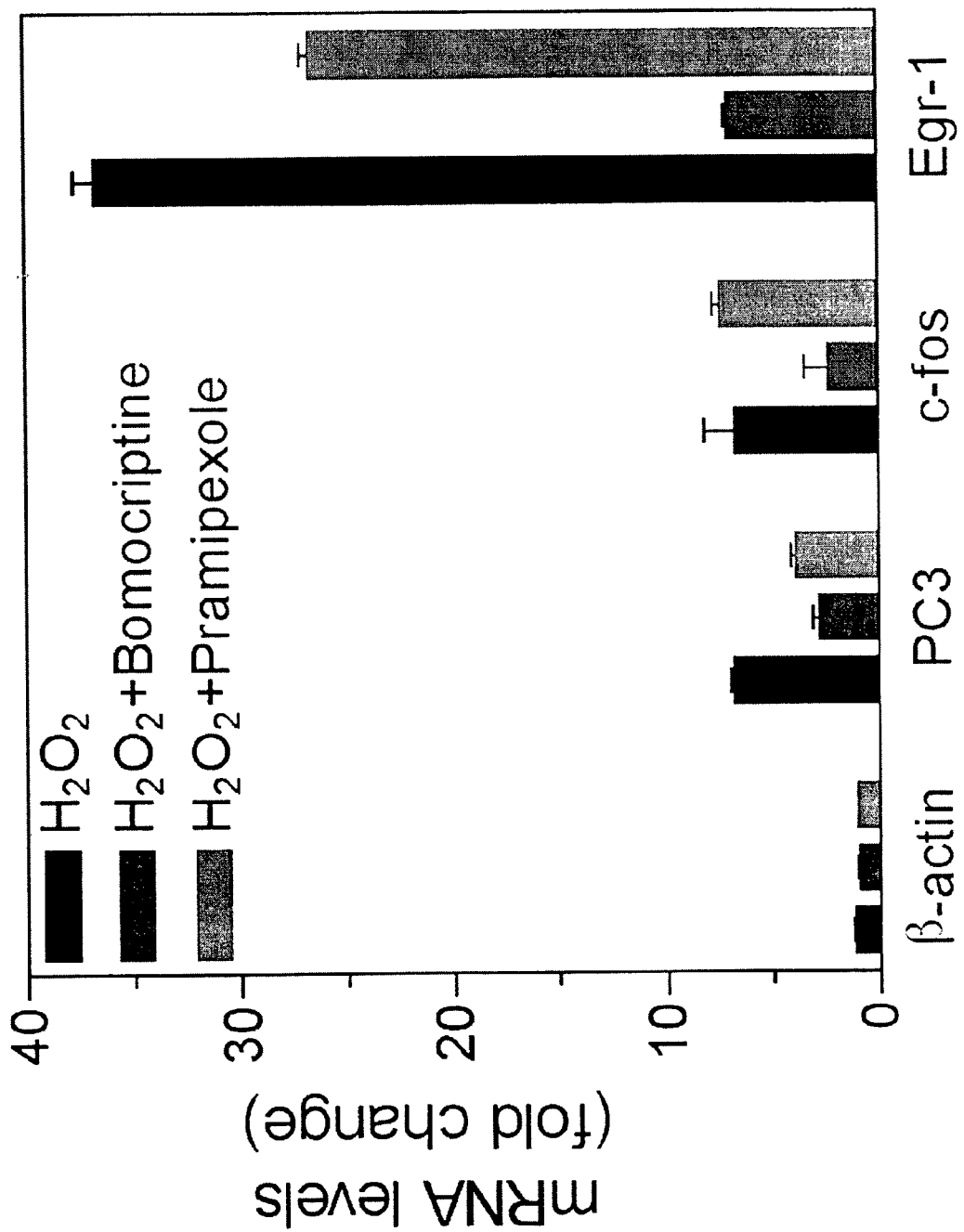
FIG. 15 demonstrates early gene expression induced by $H_2O_2$ exposure in PC12-D2R cells suppressed by bromocriptne but not pramipexole.

Example 7 shows the induction of early genes PC3, c-fos, and egr1 with exposure of rat PC12 cells stably expressing the dopamine D2 receptor to $H_2O_2$ (FIG. 15). Bromocriptine, but not praxipexole protects the cells against PC12 induced cell death. These results indicate that monitoring these genes provides an assessment of the toxicity induced by $H_2O_2$, and can distinguish the differing effects of drugs acting at the same receptor on cellular signaling tranduction. Example 8 shorts that intrinsic reporters of cell signaling can distinguish between the effects of drugs acting through the serotonin 5-HT2A receptor in the mouse somatosensory cortex.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Monitoring G-Protein Coupled Receptor Signaling With DNA Microarrays and Real-Time PCR RNA preparation for microarray screening. Starting material sufficient to yield at least 100 µg of total RNA allows at least one labeled RNA sample for array hybridization. The RNA yield from specific cell lines varies greatly and should be determined from pilot experiments. For example, the HEK293 cells used to generate the regression data in FIG. 1 yield approximately 1 mg total RNA from one 15 cm plate grown at 90% confluence (30 million cells). In contrast, the mouse gonadotrope cell line, LβT2 yields less than 200 µg RNA from 30 million cells. Cells are treated with agonist and harvested at selected time points for RNA extraction. Total RNA can be isolated using the guanidinium thiocyanate method described by Chomczynski and Sacchi (1987) Anal. Biochem. 162: 156-9, herein specifically incorporated by reference in its entirety. All plastic ware and solutions are preferably RNAse free.

The protocol is as follows:
1. Remove the culture medium and add 10 ml lysis buffer/15 cm plate. Lysis buffer consists of 4 M guanidinium thiocyanate. 25 mM sodium citrate, pH 7.0, 0.5% sarcosyl (N-lauroyl-sarcosine). 0.1 M 2-mercaptoethanol The method for preparation of the lysis buffer is described in Chomczynski and Sacchi (1987) supra.
2. Triturate the sample several times. It may be very viscous initially Briskly swirling the plates on a laboratory rotator helps to decrease viscosity.
3. Collect the lysate into a 50 ml centrifuge tube (Falcon 2070).
4. Add 1 ml 2 M sodium acetate (pH 4.0). Mix thoroughly by inversion.
5. Add 10 ml water-saturated phenol. Mix thoroughly by inversion.
6. Add 2 ml chloroform-isoamyl alcohol (49:1). Shake vigorously for 15 seconds.
7. Centrifuge at 2000 g for 30 minutes at 4° C. (e.g., Sorvall RT-6000B benchtop centrifuge fitted with a H1000B rotor).
8. Collect the upper aqueous phase to a new 50 ml centrifuge tube. Avoid taking the interphase or the lower phase.
9. Add 10 ml isopropanol and mix thoroughly by inversion. Incubate at −20° C. for at least 1 hour to precipitate the RNA.
10. Centrifuge at 2000 g for 30 minutes at 4° C.

11. Remove supernatant.
12. Resuspend the pellet in 0.75 ml lysis buffer. Transfer to a 1.5 ml microcentrifuge tube.
13. Add 0.75 ml isopropanol and mix thoroughly by inversion. Incubate at −20° C. for at least 1 hour to precipitate the RNA.
14. Centrifuge at 16000 g for 10 minutes at 4° C. in a microcentrifuge (Eppendorf 5415C).
15. Remove supernatant.
16. Wash with 1 ml 70% ethanol. Centrifuge at 16000 g for 5 minutes at 4° C.
17. Remove supernatant and air dry the pellet for 15 minutes.
18. Resuspend the RNA in at least 100 μl DEPC-treated water. If a large quantity of RNA is prepared, the pellet can be difficult to dissolve. If needed, increase the volume of water, heat for 10 min at 65° C. and vortex vigorously.
19. The concentration of the RNA is determined by absorbance at 260 nm and is then adjusted to 0.5 μg/μl.

For isolating Poly(A)+RNA from total RNA, presently utilize a commercial magnetic separation kit. PolyATtract mRNA isolation system, Cat# Z5300 (Promega), following the manufacturer's instructions. While it is possible to label total RNA for microarray screening, it is preferable to use poly(A)+ RNA. Poly(A)+ isolation takes 1-2 hours.

Sample validation: Prior to performing the microarray labeling and hybridization, the quality of the mRNA samples is determined and, if possible, the presence of consistent regulatory responses confirmed. The mRNA samples are tested using real-time PCR (see details below) The expression of several control genes and of genes that are known from the published literature or previous experience to be regulated by receptor activation are quantified. Egr-1, for example, was found to be activated following the stimulation of many receptors. These assays allow confirmation that the mRNA samples to be labeled are of good quality. These validation studies also confirm that the level of control genes, such as actin, shows an expected stability and that at least some regulated genes show a consistent increase of a reasonable magnitude. If the PCR analysis of these samples reveal significant variation among samples in the same experimental group, the treatment and RNA isolation is repeated.

Microarray labeling and hybridization. A variety of array formats, both commercial and custom printed, are available. Commercial filter arrays that are hybridized with radioactively-labeled probe can be used, but custom printed dual-fluorescent label cDNA microarrays are preferable. Many academic institutions have established shared facilities to print and distribute high density cDNA arrays. Custom-printed arrays, while requiring more expertise to utilize, are considerably less expensive. In dual-labeled cDNA microarrays, the experimental samples are labeled with one fluorophore and are mixed with a pooled reference sample labeled with a second fluorophore. Thus the results obtained for each experimental sample are compared to the internal standard for each microarray. High density oligonucleotide arrays are available from Affymetrix. (Lipshutz et al. (1999) Nat Genet 21: 20-24, the contents of which are hereby incorporated by reference in their entireties) provide a description of the design and manufacture of commercial high density oligonucleotide arrays. In this system, each array is hybridized with biotinylated cRNA probe that is subsequently stained with a secondary fluorescent antibody. Hybridization and data acquisition require access to hybridization and data acquisition instruments dedicated to the Affymetrix arrays The regression data generated in FIG. 1 was obtained using this system. The probe is generated following the instructions of the supplier and its suitability for high density arrays is assessed with a manufacturer-supplied test array. The test array hybridization is evaluated to judge probe length (ratio of 3'- to 5'-probes), the presence of spiked bacterial controls, and the level of noise and background. The samples showing satisfactory test hybridization are then hybridized with the high-density arrays.

Data validation. There are a variety of academic and commercial software programs available for the acquisition and analysis of microarray data (Bassett et al. (1999) Nat Genet 21:51-55, the contents of which are hereby incorporated by reference in its entirety). An initial analysis is perform of fluorescence intensity oligonucleotide hybridization data using Microarray Suite 4.0 (Affymetrix). After initial data extraction, a value is exported reflecting the average expression (average perfect match/mismatch difference, as explained in software documentation) for each gene to an Excel spreadsheet. The quality of the data in each sample can be first estimated by examining the regression pattern obtained by comparing that sample's dataset to that of other samples. In a comparison of any two samples following receptor stimulation, the majority of genes are expected to be unaltered. Therefore, an ideal regression plot comparing the level of expression of all genes in two sample should approach a straight line through the origin with a uniform slope of unity. The deviation from a straight line predominantly represents sample variation and measurement error. Two types of patterns are shown in FIG. 1. In FIG. 1A, the linear regression is straight and the scatter relatively small (r=0.98). In FIG. 1B, the curve is slightly "S" shaped and the scatter is greater (r=0.95). As only sample 3 is unique to FIG. 1B, this pattern suggests that the data obtained from sample 3 is noisier. A poor regression pattern obtained with a given sample appears the same when that sample is compared to other samples from both experimental and control groups. Only sample datasets showing acceptable regression patterns are used for subsequent analysis. The initial analysis on satisfactory datasets can be performed by determining the mean and standard error of the changes in expression and evaluation of the levels of the previously documented control and regulated genes (see above). Datasets containing multiple time points or conditions are analyzed using clustering algorithms (see below). All regulated genes of interest identified by microarray are confirmed and studied in full concentration-response experiments using real time PCR.

Oligonucleotide design for real-time PCR assays. Real-time PCR can provide rapid and precise confirmation and follow-up studies of gene changes identified by microarray studies. Alternatively, Real-time PCR can be used alone, in lieu of the microarray studies. Presently, all real-time PCR systems rely upon the detection and quantification of a fluorescent reporter, the signal of which increases in direct proportion to the amount of PCR product in a reaction. However, if and when alternative probes are developed, such modifications can also be used in the methods of the present invention.

Real-time PCR overcomes the quantification problems found with standard PCR reactions. At the beginning of a PCR reaction, reagents are in excess, and template and product are at low enough concentrations so that product renaturation will not compete with primer binding. Thus initially amplification proceeds at a constant, exponential rate. However, as the reaction rate ceases to be exponential and enters a linear phase, the amplification will vary significantly from one reaction to another, and even varies among replicate samples. This has been attributed to product renaturation competing with primer binding. As the reaction further proceeds, the amplification rate will eventually reach a plateau and essentially no additional product is generated. Since the kinetics of the amplication varies with the reaction, quantification of standard PCR amplification is unreliable. In direct contrast, real-time PCR provides a means for collecting data at the point when every sample is in the exponential phase of amplification, which is required for meaningful quantification.

There are several different approaches to real-time PCR. For studies of IRCs, SYBR® Green detection real-time PCR is preferred because multiple reactions can be set-up rapidly and inexpensively using standard oligonucleotides. As indicated above, real-time PCR relies on the fluorescent quantification of PCR product during each cycle of amplification. Specific detection systems, such as molecular beacons and Taqman® assays rely on the synthesis of a fluorescently labeled detection oligonucleotide. These specific assays have the advantage of specificity, but the disadvantage of added expense and a delay in obtaining the fluorescently labeled detection oligonucleotides. Assay of PCR product through the use of the fluorescent dye SYBR® Green allows the reaction to be based on standard oligonucleotides. Because SYBR® Green can detect any PCR product, including non-specific products and primer-dimers, careful oligonucleotide design for the reaction is required.

Primers should be designed, if possible, within 1 kb of the polyadenylation site. Amplicons of 100-200 bp are ideal for real time applications. It is advantageous to design the primers to have the same melting temperature so that PCR with different primer sets can be performed in the same run. One such design primers are 20-mers with 55% GC content and a single 3'-G or C. Candidate primers are tested for specificity by BLAST and for folding and self-annealing using standard DNA analysis software. Primer pairs are first tested for specificity and absence of primer-dimer formation (low molecular weight products) by PCR followed by gel electrophoresis. Designing each primer pair takes about one hour.

RNA extraction and reverse transcription for PCR. PCR is reliable with relatively small quantities of the RNA target. Therefore only small numbers of cells are needed for sample generation. Typically cells grown in multi-well plates (6, 12 or 24 wells) can be used and RNA can be isolated using a commercial 96 well plate format RNA isolation column, StrataPrep96 Cat#400790 (Stratagene). Results from most cell lines are more reliable if lysed cells are first pre-filtered using 0 45 micron acetate filters (Costar Spin-X #8163). 200 samples can easily be treated and processed within a day using this approach. This allows the analysis of full concentration-response curses with triplicate samples.

In a particular protocol 5 µg total RNA is used in the first strand cDNA synthesis. To a sterile nuclease-free 0.5 ml microcentrifuge tube, add:

| | |
|---|---|
| 1 µl | DEPC-treated water |
| 10 µl | total RNA (0.5 µg/µl) |
| 1 µl | Oligo (dT)$_{18}$ (0.5 µg/µl) |

Incubate the mixture at 65° C. for 5 minutes. Quick chill mixture on ice. Centrifuge at 16000 g for 10 seconds at 4° C. to collect the contents of the tube. Then add:

4 µl 5× first strand buffer (250 mM Tris-HCl, pH 8.3 at room temperature, 375 mM KCl, 15 mM MgCl$_2$)
2 µl 0.1 M DTT
1 µl Superscript II (200 units/µL) (Life Technologies)
1 µl dNTP mix (10 mM each dNTP)

Mix gently and incubate at 42° C. for 50 minutes. The reaction is then stopped by heating at 70° C. for 15 minutes. To prepare the samples for PCR, 2 µl of the first strand cDNA is diluted with deionized water to 100 µl. Typically 5 µl of this dilution is used in each PCR reaction. Assuming that the polyA+ RNA population is 2% of the total RNA, approximately 500 pg of the first strand cDNA is used as template in the real time PCR.

Real-time PCR. Real-time PCR requires a specialized thermocycler with fluorescent detection. A variety of commercial instruments are available. One such instrument is the ABI Prism 7700 which allows assays to be performed in 96 well plate format. Good PCR technique is required to avoid contamination of subsequent reactions. This includes isolating PCR products and plasmids from RNA preparation and reaction setup. A dedicated bench for RNA isolation and PCR reaction set-up and dedicated pipettors should be maintained. Aerosol resistant pipette tips are used. Commercial kits for SYBR® Green based PCR reactions are available from Applied Biosystems and perform reliably (SYBR Green PCR Core Reagents, P/N 4304886; SYBR Green PCR Master Mix, P/N 4309155). A protocol for the reaction components can be as follows:

TABLE 5

| Reaction Component | Volume per 20 L reaction (l) | Volume per 100 reactions (l) |
|---|---|---|
| deionized water | 10.4 | 1040 |
| 10X PCR buffer (200 mM Tris-HCl pH 8.4, 500 mM KCl) | 2.0 | 200 |
| 50 mM MgCl$_2$ | 1.2 | 120 |
| 10X SYBR ® Green I | 0.1 | 10 |
| 10 mM dNTPs | 0.4 | 40 |
| Primer mix (5 µM each) | 0.8 | 80 |
| Taq DNA Polymerase (5 U/µL) | 0.1 | 10 |

"HOT START®" type of taq polymerase is preferred. Platinum Taq®, (Life Technologies), and AmpliTaq® gold, (Applied Biosystems), both perform well. The 10× SYBR® Green I is prepared by diluting 10 µl of the stock 10,000× concentrate (Cat# S-7563, Molecular Probes, Eugene, Oreg.) into 10 ml Tris-HCl, pH 8.0, and is stored in 0.5 ml aliquots at −20° C. 15 µl of the master mix are aliquoted into 0.2-mL MicroAmp optical tubes (P/N N801-0933, Applied Biosystems). Alternatively, a 96-well optical reaction plate (P/N 4306737, Applied Biosystems) can be used. Five µl of the first strand cDNA is then added to the tube and the solution is then mixed by repeat pipetting. This achieves a final concentration reaction containing 20 mM Tris, 50 mM KCl, 3 mM MgCl$_2$, 0.5×SYBR® Green I, 200 µM dNTPs, 0.2 µM each of the forward and reverse primers, approximately 500 pg first strand cDNA, and 0.5 units Taq polymerase. The reaction tubes are covered with MicroAmp® optical caps (P/N N801-0935, Applied Biosystems) using a cap-installing tool (P/N N801-0438, Applied Biosystems). The contents are collected to the bottom of the tube by brief centrifugation in a Sorvall RT-6000B benchtop centrifuge fitted with a microplate carrier (PN 11093, Sorvall). The tubes are then placed in the ABI 7700 thermocycler and incubated at 95° C. for 2 minutes (10 minutes if using AmpliTaq® gold) to activate the enzyme and denature the DNA template. Forty cycles of PCR amplification are then performed as follows: Denature at 95° C. for 15 seconds, Anneal 55° C. for 20 seconds, Extend 72° C. for 30 seconds.

This protocol works well for amplicons up to 500 base pairs. For longer amplicons, the extension step should be adjusted accordingly (approximately 1 minute per kb). Either the FAM or the SYBR® channel can be used for fluorescence detection of SYBR® Green I. Fluorescent emission values are collected every 7 seconds during the extension step. Data are analyzed using Sequence Detector version 1.7 software (Applied Biosystems). In order to obtain the threshold cycle ($C_T$) values, the threshold is set in the linear range of a semi-log amplification plot of Rn against cycle number. This ensures that the $C_T$ is within the log phase of the amplification. Here the Rn is the fluorescence emission value minus baseline fluorescence value. When the PCR is at 100% efficiency, the $C_T$ decreases by 1 cycle as the concentration of DNA template doubles.

Figure 2:
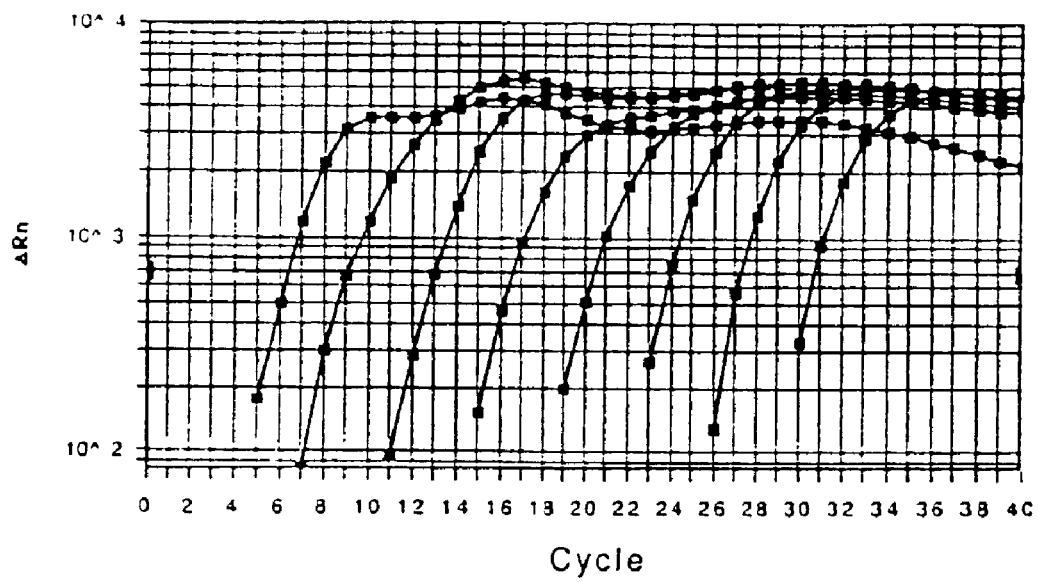
FIGS. 2A-2B show a standard curve generated with real-time PCR. PCR for an egr-3 amplicon was performed using serial 10-fold dilutions of an egr-1 cDNA as a template.
Figure 2:
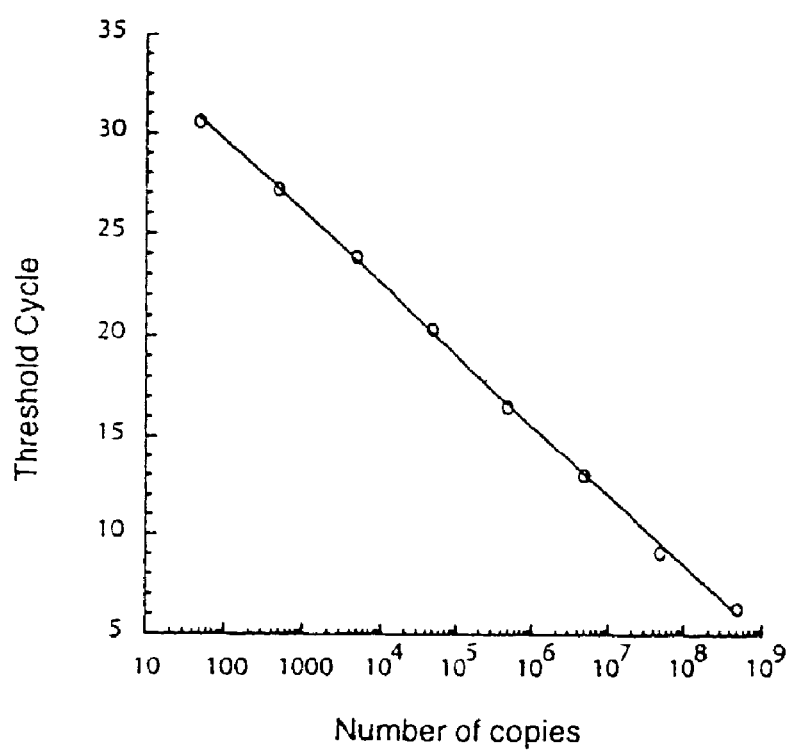
Figure 3:
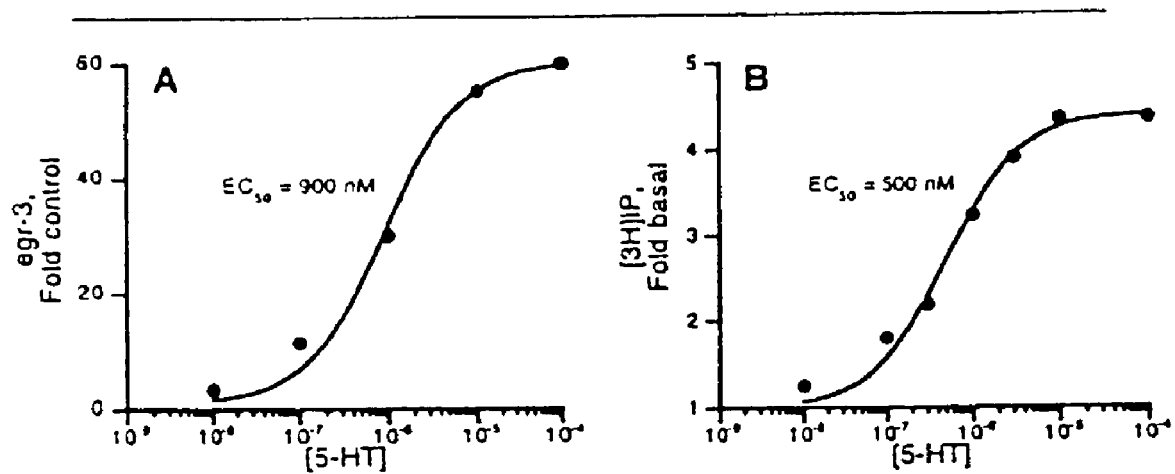
FIGS. 3A-3B show an intrinsic reporter concentration-response curve. HEK293 cells were stably transfected with the human 5-HT2A receptor and the resulting cells were treated in triplicate with varying concentrations of serotonin (5-HT).

In order to confirm that the correct amplicon is made, the amplified products are analyzed by agarose gel electrophoresis and visualized by ethidium bromide staining. A good reaction yields a single band of the expected size and has no smearing or primer-dimer formation. To generate a standard cure for each primer pair, 10-fold serial dilutions are made from a plasmid with a known number of copies of the gene The $C_T$ of each dilution is determined, and is plotted against the log value of the copy number Amplification efficiency of each primer pair is obtained by the slope of regression (FIG. 2). A 100% efficient PCR has a slope of −3.32. The number of copies in the samples is intrapolated by its $C_T$ value using the respective standard curve. The potential for IRC assays to monitor signal transduction is illustrated in FIG. 3, which shows a serotonin concentration-response curve of egr-3 levels generated using 5-HT2A receptor-expressing HEK293 cells. The egr-3 response curve closely resembles that obtained with a classical assay of accumulation of inositol phosphates.

Example 2

Focused Microarray Analysis of Gonadotropin Releasing Hormone Receptor-Coupled Gene Network Organization Cell Culture and Sample Preparation: LβT2 cells were obtained and maintained at 37° C. in 5% $CO_2$ in humidified air in DMEM (Mediatech) containing 10% fetal bovine serum (Gemini). For experiments. 40-50×$10^6$ cells were seeded in 15 cm dishes. The medium was replaced 21 hours later with DMEM containing 25 mM HEPES (Mediatech) and glutamine. 18 hours later, the cells were treated with 100 nM GnRH or vehicle and were returned to the $CO_2$ incubator for 1 hour. The incubation was stopped by aspirating the incubation medium and adding 10 ml of lysis buffer (4M guanidinium thiocyanate, 25 mM sodium citrate, pH 7.0, 0.5% N-lauroyl-sarcosine, and 0.1 M 2-mercaptoethanol). Total RNA was isolated according to the method of Chomczynski and Sacchi (1987) supra. Approximately 400 μg total RNA was obtained from each plate.

Microarray Development: The 956 clones were selected from an NIA 15K library (Tanaka et al. (2000) Proc. Natl. Acad. Sci. USA 97:9127-9132) or purchased from Research Genetics. The gene selection was partially based on literature searches. A large number of genes known to be induced at early time points in other experimental systems were included as well as 67 putative "housekeeping" genes. Plasmids were purified using the Qiaprep 96 Turbo Miniprep kit. Following insert amplification by PCR, products were confirmed by agarose gel electrophoresis and purified with Qiaquick 96 kit (Qiagen). The product was dried, dissolved in 18 μl $H_2O$. 50% DMSO or 3×SSC and spotted (3 hits/feature, 3 features/gene) with a GMS 417 Arrayer (Affymetrix) on CMT-GAPS coated glass slides (Corning). DNA was fixed either by incubating the slide 3.5 hours at 40° C. followed by 10 min at 100° C. or for 2 hours at 85° C. or by UV crosslinking with 90 mJ (Stratalinker, Stratagene). Arrays were stored light-protected at room temperature until use. A Cy5-labeled oligomer complementary to one of the amplification primers was designed to test printing and attachment efficiency (5'-CGT TTT ACA ACG TCG TGA CTG GG-3') (SEQ ID NO:1). 12% of the cDNAs on the array were confirmed by sequencing, including randomly selected clones on each 96-well plate and all genes that were identified as regulated.

RNA Labeling and Hybridization. 20 μg of total RNA from each sample was labeled with either Cy3 or Cy5 using the Atlas indirect labeling kit (Clontech) as indicated by the manufacturer. Following array prehybridization in 6×SSC, 0.5% SDS, 1% BSA at 42° C. for 45 min, the probe was denatured and hybridized in 24 μl 50% formamid, 6×SSC, 0.5% SDS. 5×Denhardt's with 2.4 μg salmon sperm DNA, 10 μg poly dA at 42° C. (room temperature for test oligomer hybridization) for 16 hours. Following 10 min washes in 0.1×SSC, 0.1% SDS, and twice in 0.1×SSC the slide was scanned using the GMS 418 Scanner (Affymetrix).

Real Time PCR. The protocol of Example 1 above, was used. Briefly, 5 μg total RNA was converted into cDNA and 1/200 (approximately 500 pg) was utilized for 40 cycle three-step PCR in an ABI Prism 7700 with 20 mM Tris pH 8.4, 50 mM KCL, 3 mM MgCl2, 200 μM dNTPs, 0.5×SYBR® green (Molecular Probes), 200 μM each primer and 0.5 U Platinum Taq (Life Technologies). Amplicon size and reaction specificity was confirmed by agarose gel electrophoresis. The number of target copies in each sample was interpolated from its detection threshold ($C_T$) value using a plasmid or purified PCR product standard curve included on each plate. The sequence of the 60 primer sets utilized can be found in supplementary material. Each transcript in each sample was assayed 5 times and the median $C_T$ values were used for analysis.

Data Analysis. Scanned microarray data were exported as tiff files to Genepix (Axon Instruments) and spot registration was manually optimized as suggested by the developer. The median background-subtracted feature intensity was utilized for further analysis. Overall differences in the signal intensity of the two wavelengths measured on each slide ($\lambda$=532 nm and $\lambda$=635 nm) were corrected using the locally linear robust scatterplot smoother implemented in the loess function in S Plus Professional (Insightful Corporation). Predictors were generated using a symmetric distribution, span=0.75 (Venables and Ripley (1999) *Modern Applied Statistics with S-Plus*. Spring, N.Y. Measurement precision was estimated by determining the median coefficient of variation within slides for each gene:

$$c.v. = \frac{100}{\bar{R}} \sqrt{\frac{\sum_{i=1}^{n}(R_i - \bar{R})^2}{n-1}}$$

where, R is the geometric mean ratio for that gene on each slide. $R_1$ is each ratio, and n is the $$s_R^2 = \sum_{t=1}^{k} \sum_{i=1}^{n_t} \frac{(y_{ti} - \bar{y}_t)^2}{N-k}$$

number of measurements. Analysis of variance was determined as described (Box et al. (1978) *Statistics for Experi-* menters: *An Introduction to Design, Data Analysis, and Model Building*, Wiley, N.Y.). Variance within, where, k is the number of arrays, n=3 is the number of measurements of each gene on each array, yti=the individual ratios and y$_t$bar is the average ratio $$s_T^2 = \frac{\sum_{t=1}^{k} n_t(\bar{y}_t - \bar{y})^2}{k-1}$$

on each array.

Variance between: where, k is the number of arrays, n is the number of measurements, ybar is the average from all experiments.

In order to select genes for further study, t values for the log transform ratios (r) were determined for data from each slide.

$$t = \frac{\bar{r}\sqrt{n}}{s}, \text{ where } s = \sqrt{\frac{\sum_{t=1}^{n}(r_t - \bar{r})^2}{n-1}}$$

Genes were selected according to the following algorithm (i) ±fold-change of >1.3; (ii) |t|>3; (iii) signal intensity in at least one channel >1% of the median signal intensity value; (iv) criteria i-iii observed in at least 2 of 3 experiments.

Results. Modulation of the cell's transcriptional activity tracks the receptor-mediated changes of activity in the cell's signaling space. Monitoring transcriptional activity shortly after receptor activation reflects the coordinated changes in the activity of multiple signal transduction pathways and may also identify the gene products involved in signal feedback and in controlling the transcription of downstream targets. To overcome the potential limitations of global microarrays, an integrated microarray technology is disclosed with a massively parallel candidate gene approach that is referred to herein as focused microarray analysis (FMA). As disclosed herein, this approach has been used to develop an early gene microarray for the study of GnRHR responses. 956 cDNAs were carefully selected for inclusion on this microarray, including most genes identified as intrinsic reporters of cell signaling. The size of this array facilitates high quality array production, validation, and data generation.

Array Design and Quality Control. Many factors can contribute to array quality. Feature morphology may be influenced by surface tension effects arising from surface and spotting solution chemistry and by attachment efficiency. Feature morphology and attachment were evaluated following hybridization using a Cy5-labeled test oligonucleotide and multiple clones on a small test array Several suspension solutions and fixing protocols were compared in a 3×3 design. Test arrays were hybridized with a Cy5-labeled oligonucleotide against one of the PCR primers used for cDNA amplification in order to optimize the printing solution and attachment protocol. PCR products were suspended in several test solutions and were fixed to the slide using either baking (two protocols) or UV cross-linking. Each slide contained the three spotting solutions evaluated. 3×SSC solution caused ring artifacts (results not shown). Either two-stage heating or UV crosslinking caused unreliable attachment. The best signal and morphology was obtained with 50% DMSO solution and 2 hours baking at 85° C. The optimum morphology and intensity were reproducibly observed, independently of insert sequence or size, with the PCR product dissolved in 50% DMSO and fixed for 2 hours at 85° C. to CMT-GAPS coated slides.

In order to distinguish signals arising from surface artifacts and facilitate analysis, the 956 selected genes were spotted in triplicate using the optimum attachment protocol. The quality of the libraries utilized and the reliability of the clone picking and isolation were evaluated by sequencing 119 clones on the array. 92% of clones picked from the NIA library and 82% of the clones purchased from Research Genetics had been correctly identified. Based on the distribution of clone sources, it can be estimated that clone identification of the unsequenced clones on the array was 91% accurate. 98.7% of clones generated sufficient PCR product to be detectable by gel electrophoresis and 100% of clones were detected by hybridization with a test oligomer. Test hybridization confirmed the presence of all spotted genes at similar concentrations. Hybridization was uniform across each array and background signal was low (results not shown).

Microarray Identification of Genes Activated by GnRH is LβT2 Cells. The response to GnRH was studied in the GnRHR-expressing LβT2 gonadotrope cell line (Turgeon et al. (1996) Mol Endocrinol. 10:439-450). Three separate experiments comparing the effects of 1 hour exposure to GnRH or vehicle were performed. Data reproducibility and labeling bias were assessed by repeating the labeling and hybridization for one pair of samples two additional times, once with the control and treatment, Cy3 and Cy5 labels reversed. The reliability of the data generated from these microarray experiments was substantiated by the reproducibility of measurements within arrays, between arrays and between experiments. The pattern of hybridization observed was qualitatively similar for all experiments. Because the triplicate measurements within each array were nearly identical for each of the 5 hybridizations (median c.v. 8-13%), regulated genes could reliably be distinguished from surface artifacts The reproducibility of the three measurements of each gene on each slide was utilized in the data analysis algorithm (see above). When the identical two RNA samples (control and treatment) were labeled repeatedly, the pattern of hybridization was similar. The linear correlation coefficient for the ratios of regulated genes (see Table 2) obtained from analysis of these two repeated labelings and arrays was r=0.985. Furthermore, nearly identical microarray results were obtained with these same two samples when the dyes labeling control and GnRH-treatment RNAs were reversed. The correlation coefficient between the ratios obtained in the first array and the dye-swap array was r=0.975. These data indicate that the relative expression obtained from these comparisons are reproducible and do not show sequence bias, as has been reported with direct labeling protocols (Taniguchi et al. (2001) Genomics 71:34-39).

In order to determine the relative sources of variability (error) in these experiments, an analysis of variance was performed. The median sample variance between the ratios obtained with repeated labeling/hybridization of the same samples and between RNA samples from separate experiments were $s_T^2$=0.0073 and $s_T^2$=0.0071 respectively. These data show that in the experimental system, the biological variability (between separate RNA samples) and the measurement variability (between repeated labeling and hybridizations of the same samples) are remarkably close. The median variance for the triplicate measurements within each array for all arrays was smaller, $s_R^2$=0.0012. These results indicate that the RNA labeling and hybridization represent a significant source of variability in these experiments.

Scatter graphs of data from the three independent stimulation experiments, normalized using the robust locally linear loess function, were obtained (data not shown). This approach is preferred to an overall linear correction because it compensates for variation of the correction factor with signal intensity and is largely unaffected by outliers which include regulated transcripts. Most transcripts are not regulated and the normalized data are tightly grouped along y=x. The triplets corresponding to several regulated genes are evident and show similar regulation and scatter graph location in all three experiments. These strikingly similar results obtained in independent experiments reflect a high level of reliability and reproducibility in all aspects of these studies, including array production, cell culture and treatment, RNA extraction, labeling, hybridization and data acquisition.

In order to identify candidate genes whose regulation is less marked than the visually obvious triplets, an empirical selection algorithm was implemented. The presence of triplicate features for each cDNA allowed calculation of a t statistic for each gene on each array. The criteria utilized to select the regulated gene candidates was based on fold-change (>1.3), the t statistic (>3) and signal intensity (>1% of median signal intensity in at least one channel) within each experiment (see methods). Genes that met these criteria in at least two independent experiments were selected for further study. This selection strategy identified 31 candidate regulated genes, 28 of which increased and 3 decreased (see below). Four real-time PCR confirmed, regulated genes (Rgs2, TSC22, PRL1 and Nrf2) were represented by two different clones and spotted in different locations on the arrays. In all cases regulation was detected by our criteria and the degree of change was similar (Rgs2 4.0±1.3, 2.9±1.2; TSC22 3.4±0.4, 3.3±0.6; PRL1 2.0±0.4, 1.5±0.4; Nrf2 1.3±0.2, 1.3±0.1). These data indicate that the observed changes were independent of position on the array.

Figure 4:
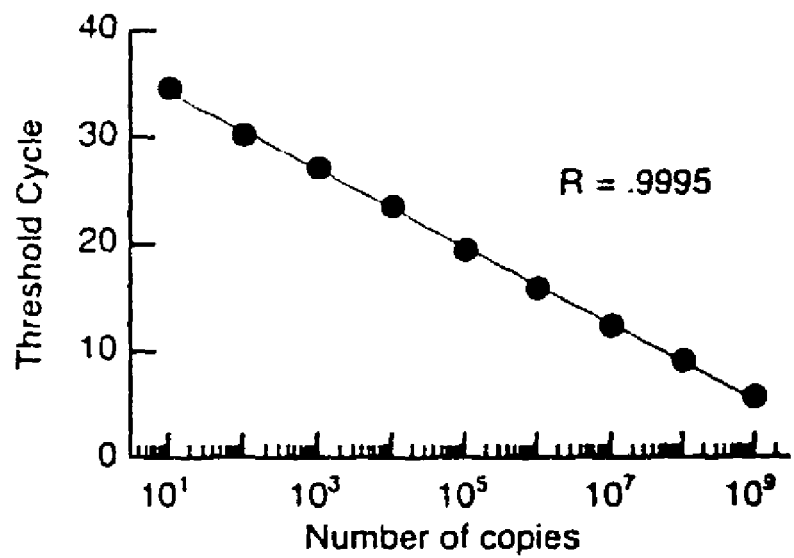
FIG. 4 is a standard curve for real-time PCR taken from Egr1.
Figure 5:
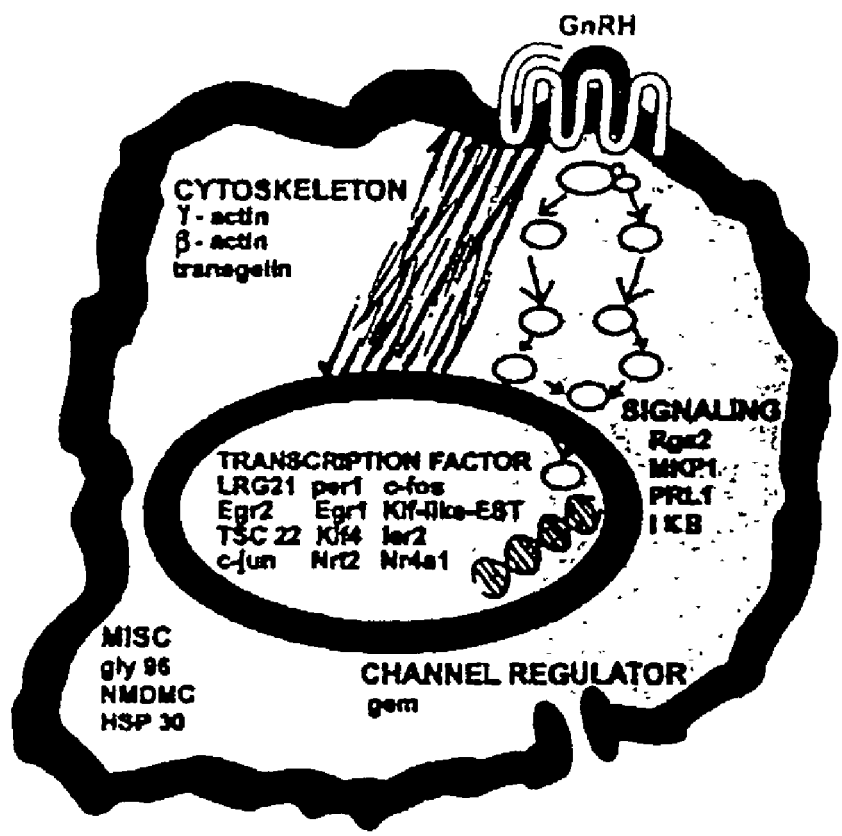
FIG. 5 is a schematic diagram of transcripts regulated by GnRH in LβT2 cells. Shown are all the microarray genes identified as being regulated by GnRH in LβT2 cells that were also confirmed by real time PCR.

Confirmation of Gene Regulation by Real-Time PCR. The measurement accuracy of the microarray and the biological variability of the transcriptional program identified was evaluated through a validation study comprising real time PCR assays of 60 transcripts, including 26 genes that met the threshold for regulation in the microarray assay. To generate accurate and precise reference measurements of these genes, 5 measurements were made of each gene in each RNA sample and the measurements were calibrated with a standard curve included on each PCR plate (FIG. 4). Nine experimental pairs of vehicle and GnRH-treated cultures were tested, including the microarray assayed samples. 100% (17 of 17) of the gene changes showing >1.6-fold change on the microarray and 66% (6 of 9) of gene changes showing between 1.3 and 1.6-fold changes were confirmed by PCR. All of the confirmed genes were up-regulated (Table 2). Three genes which showed a low level of regulation on the microarray had less than 1.3-fold regulation with the real time PCR. Because the threshold was set at a 1.3-fold change, these genes are considered to be not confirmed (see discussion below). 3 of 32 genes that appeared to be un-regulated on the microarray were found to be up-regulated by real-time PCR (see discussion below) Thus using independent confirmation it was found that the algorithm utilized to identify regulated genes was able to correctly identify regulated transcripts showing changes as low as 1.3-fold regulation on the microarray.

This dataset of 5400 PCR assays provides a reference standard which allows assessment of the accuracy of the microarray and reliable quantification of the degree of regulation of these transcripts following GnRH exposure. The fold-change determined by the microarray was accurate only for transcripts showing moderate levels of induction. Regulated genes detected by the microarray that showed a change below 3-fold were, on average, within 28% of the corresponding fold-change determined by real-time PCR. The accuracy of the fold-change determinations obtained from the microarray was poor for transcripts showing high degrees of regulation (see Table 2). Analysis of these data indicate that, for genes showing <20-fold regulation by PCR, the microarray measurements can be calibrated to provide a quantitative estimate of the degree of gene regulation. The power function correlation for the fold-change measurements by microarray and real-time PCR for these genes was r=0.87 (see Table 2).

Organization of the Early-Induced Gene Network. The data reveal that GnRHR activation transiently modulates the expression of a large number of genes. The regulated genes identified include transcription factors (e.g., Klf4. Egr1, Egr2), cell signaling modulators (e.g., Rgs2, IκB), channel regulators (gem) and proteins contributing to cytoskeletal dynamics (γ-actin and transgelin). More than half of the induced genes are transcription factors, including both activators and repressors, with the major structural motifs being leucine zipper factors (c-fos, c-jun, Nrf2, LRG21, TSC22) and zinc finger proteins (Egr1, Egr2, Klf4, Klf-like EST, Nr4a1). (see Table 2). Many immediate early genes are known to be only transiently induced by various stimuli. FMA of samples obtained from cells exposed to GnRH for 3 hours and 6 hours reveals that nearly all of the induced genes return to baseline levels of expression by 3 hours (see Table 2). The pattern of gene induction has important implications for the function of the GnRH modulated signaling network and for the mechanisms controlling the induction of downstream, secondary gene targets, such as LHβ. A commonality of many induced transcripts is that the proteins encoded, after synthesis, would contribute to subsequent down-regulation of receptor activated signaling. This category includes Fos, Rgs2, Iκb, MKP1, PRL1 and gem.

Example 3

Figure 6:
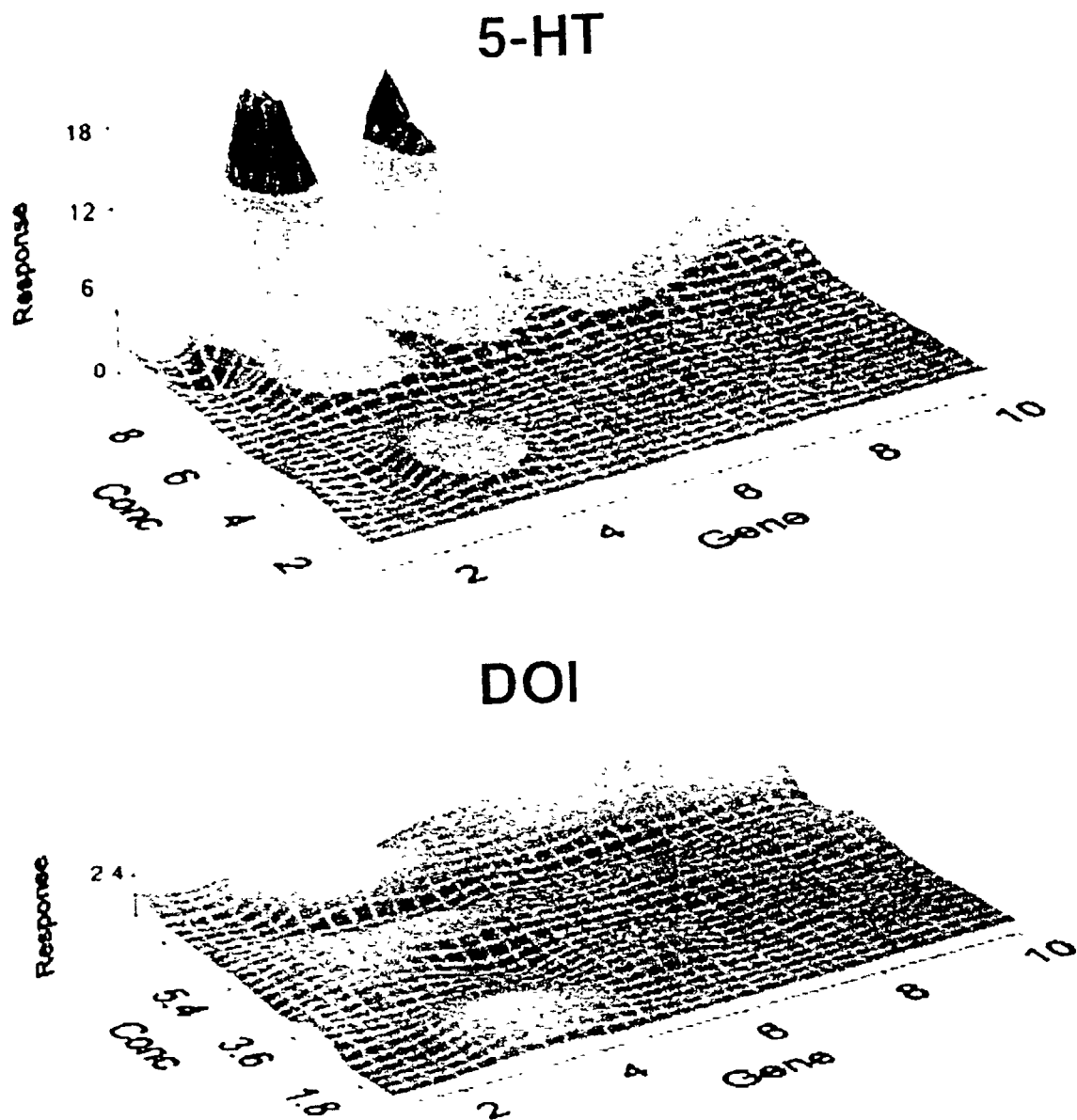
FIG. 6 is the gene response landscape for 5-HT and DOI in HEK293 cells expressing $5-HT_{2A}$ receptors. The levels of gene induction in response to 8 concentrations of each agonist for 10 genes were determined in quadruplicate samples. The height of each peak represents the level of gene induction, expressed as fold-change. In addition to the generally lower responses achieved by DOI, the landscape is notable for the different relative levels of induction of different genes. For example, the rightmost peak is highest with DOI exposure, but is lower with 5-HT exposure.

Profiling and Differentiating Drug Responses Acting at the Same Receptor Using Intrinsic Reporters of Cellular Signaling HEK293 cells were genetically engineered to stably express the human serotonin 5-HT2A receptor. Replicate aliquots of cells were treated with varying concentrations of 5-HT and DOI and the levels of a panel of IRCS after 1 hour exposure were determined by SYBR® green real-time PCR. The mean responses at each concentration were plotted in as a 3-dimensional landscape using S-plus Professional (Insightful Corp.) As shown in FIG. 6, the response landscapes obtained following treatment with the two agents are dramatically different. These results indicate the usefulness of this methodology for providing a detailed profile of the signaling responses elicited by different agents that reflects subtle differences in their activities.

Example 4

Use of Intrinsic Reporters of Cellular Signaling to Monitor Cellular Toxicity

Figure 7:
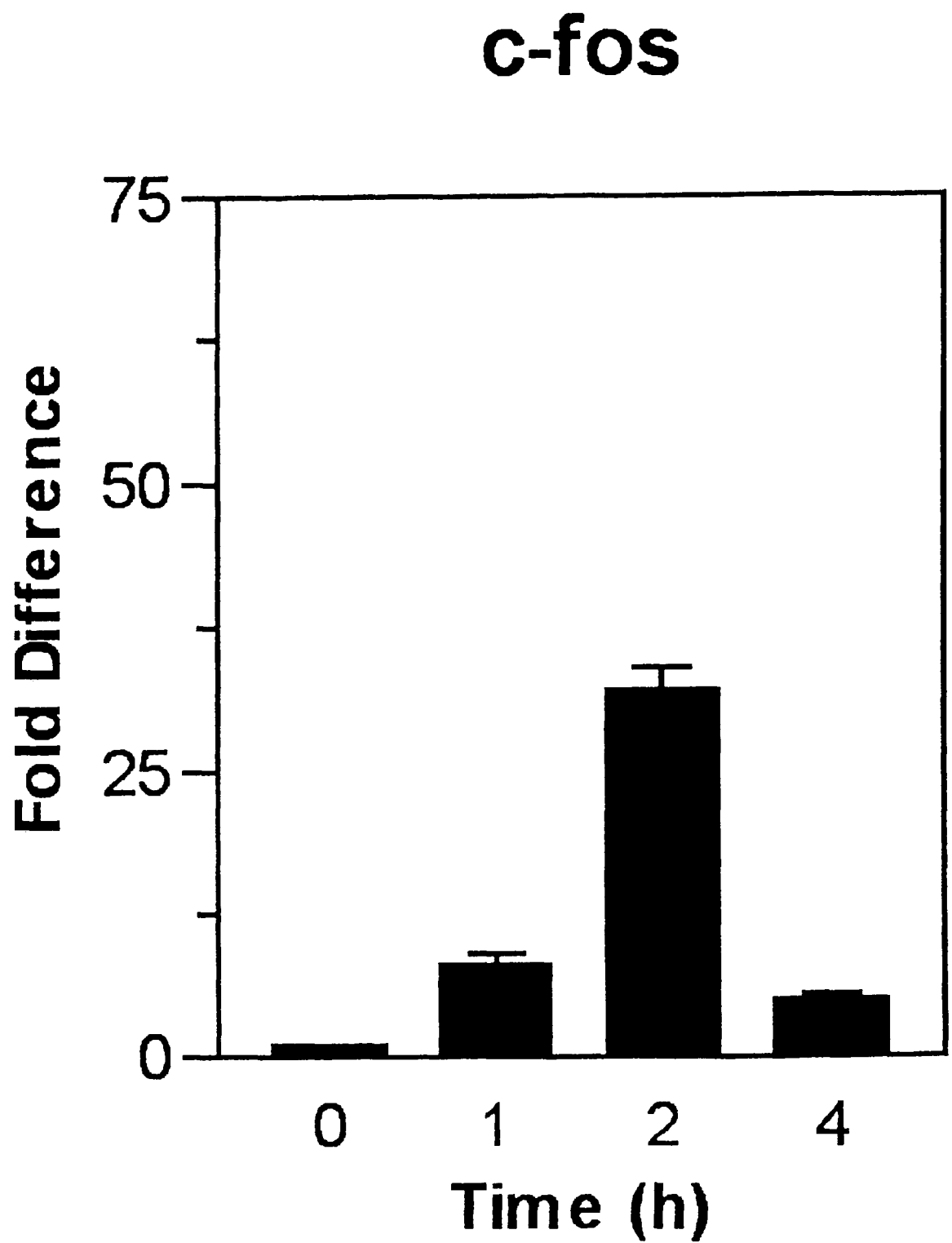
FIG. 7 demonstrates the cellular response over time to cytotoxin of the IRC c-fos in the rat neuronal cell line PC12. Cells were exposed to 200 µM $H_2O_2$ and the levels of cfos mRNA was determined using SYBR® green based real-time PCR in replicate cultures. Note the increase in this reporter elicited by this toxin, with a marked increase detected as early as 1 hour. The values shown are mean±s.e.m.
Figure 8:
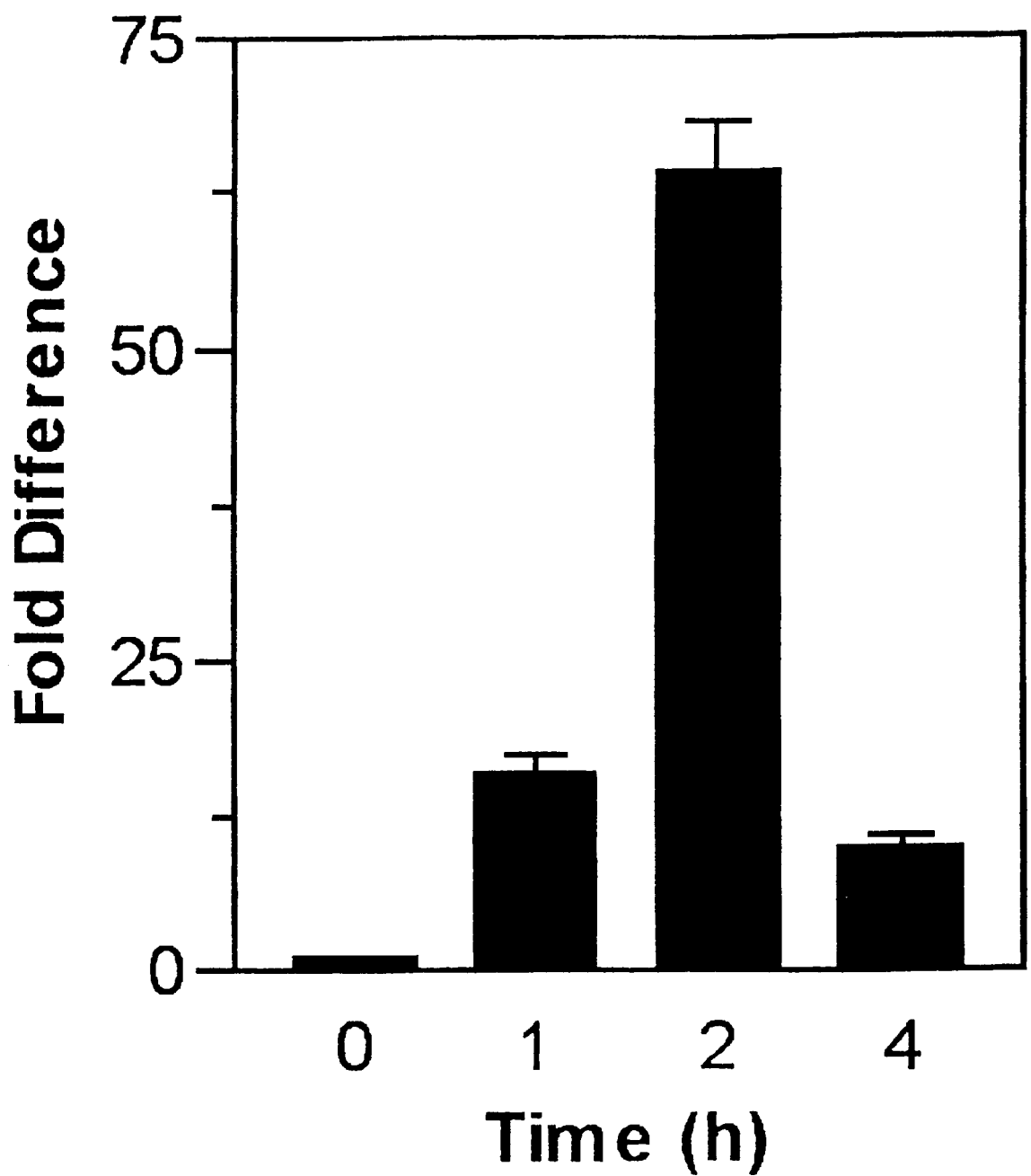
FIG. 8 demonstrates the cellular response over time to cytotoxin of the IRC egr1. The samples assayed were the same as those used to generate FIG. 7.
Figure 9:
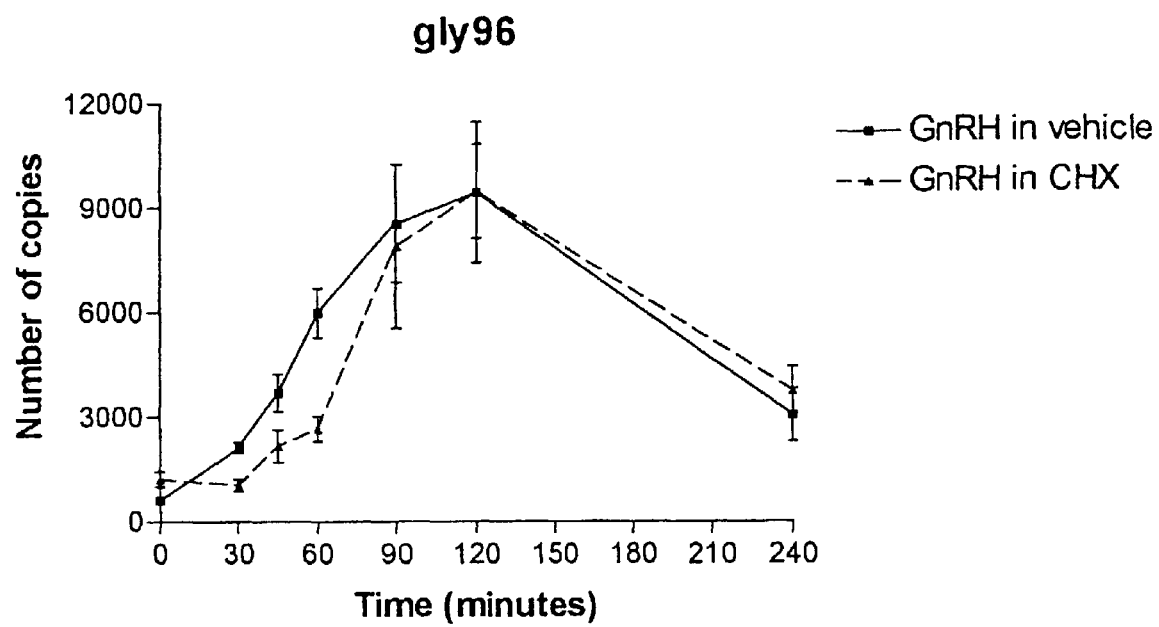
FIG. 9 demonstrates the response over time in the presence and absence of protein synthesis of the IRC gly96 to signaling activated by GnRH receptor occupancy in the gonadotrope cell line LβT2 cells. The cells were treated with 100 nM GnRH in the presence and absence of the inhibitor of protein synthesis, cyclohexamide (CHX). The increase in the levels of gly96 in the presence of CHX indicates that the transcription represents a primary gene. No other proteins need to be synthesized to induce activation of this IRC. The use of a time course such as that illustrated allow selection of the optimum time point or time points after stimulation at which to assay the IRCs to provide the most complete map of the cell global signal transduction response.
Figure 10:
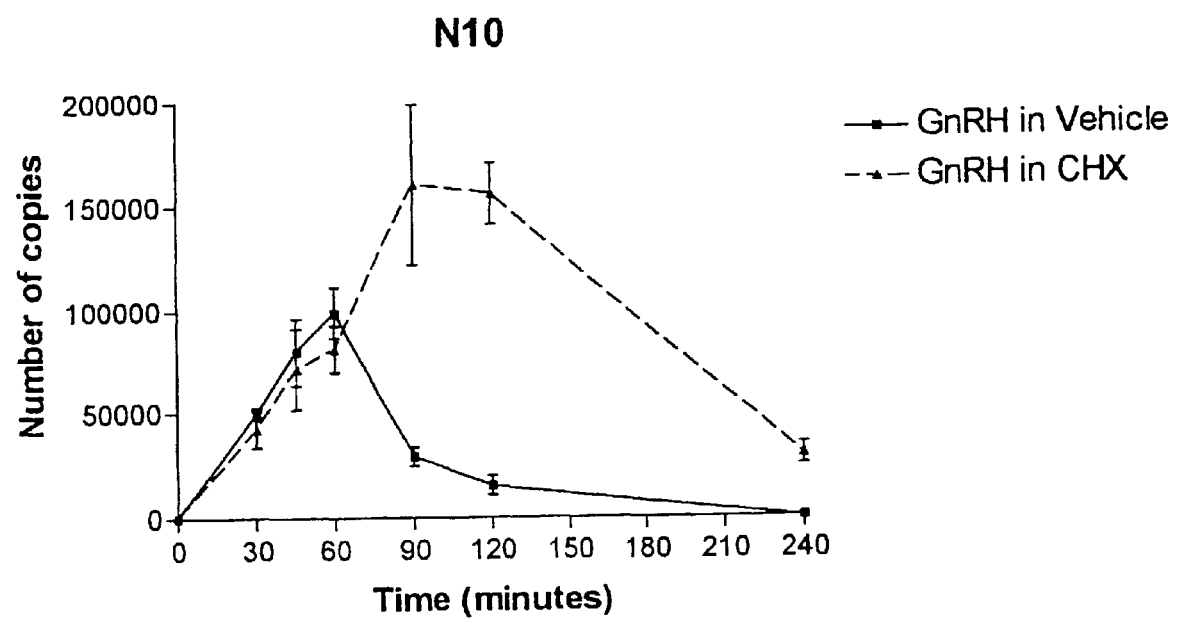
FIG. 10 demonstrates the response over time in the presence and absence of protein synthesis of the IRC N10 to signaling activated by GnRH receptor occupancy in the gonadotrope cell line LβT2 cells. The samples analyzed were the same as those in FIG. 9.
Figure 11:
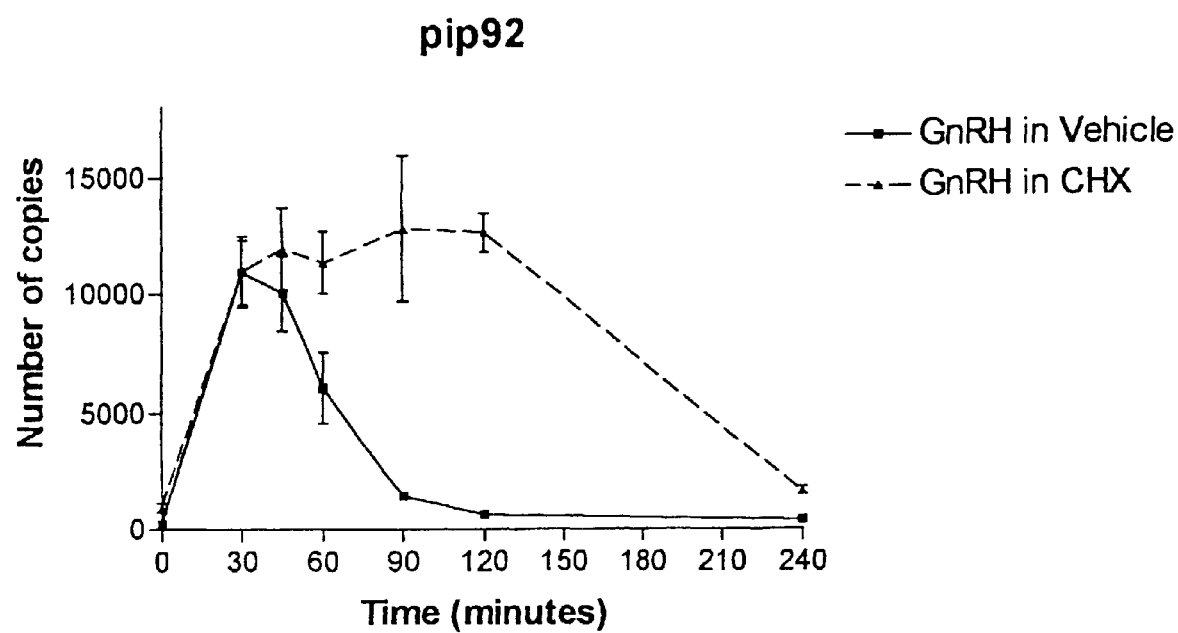
FIG. 11 demonstrates the response over time in the presence and absence of protein synthesis of the IRC pip92 to signaling activated by GnRH receptor occupancy in the gonadotrope cell line LT2 cells. The samples analyzed were the same as those in FIG. 9.
Figure 12:
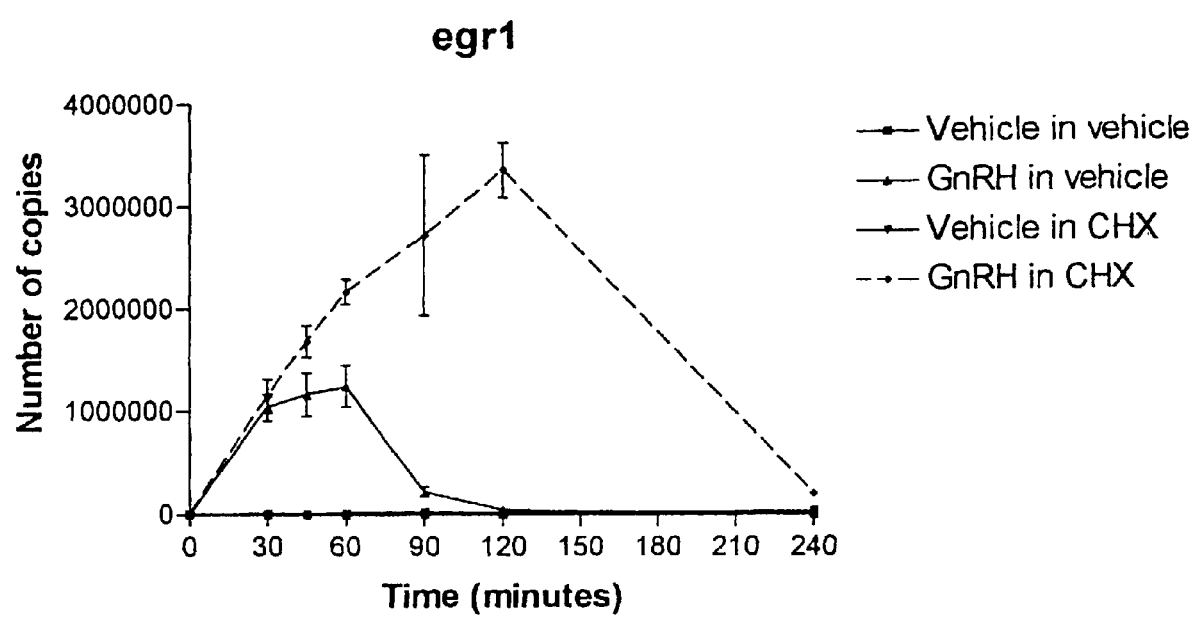
FIG. 12 demonstrates the response over time in the presence and absence of protein synthesis of the IRC egr1 to signaling activated by GnRH receptor occupancy in the gonadotrope cell line LβT2 cells. The samples analyzed were the same as those in FIG. 9.
Figure 13:
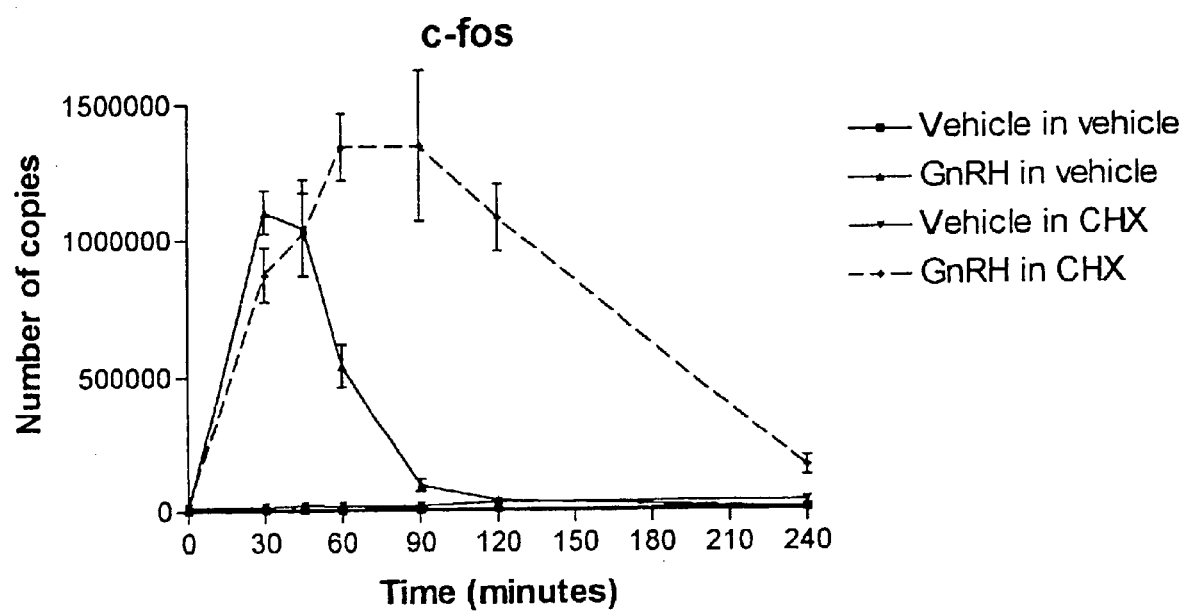
FIG. 13 demonstrates the response over time in the presence and absence of protein synthesis of the IRC c-fos to signaling activated by GnRH receptor occupancy in the gonadotrope cell line LβT2 cells. The samples analyzed were the same as those in FIG. 9.
Figure 14:
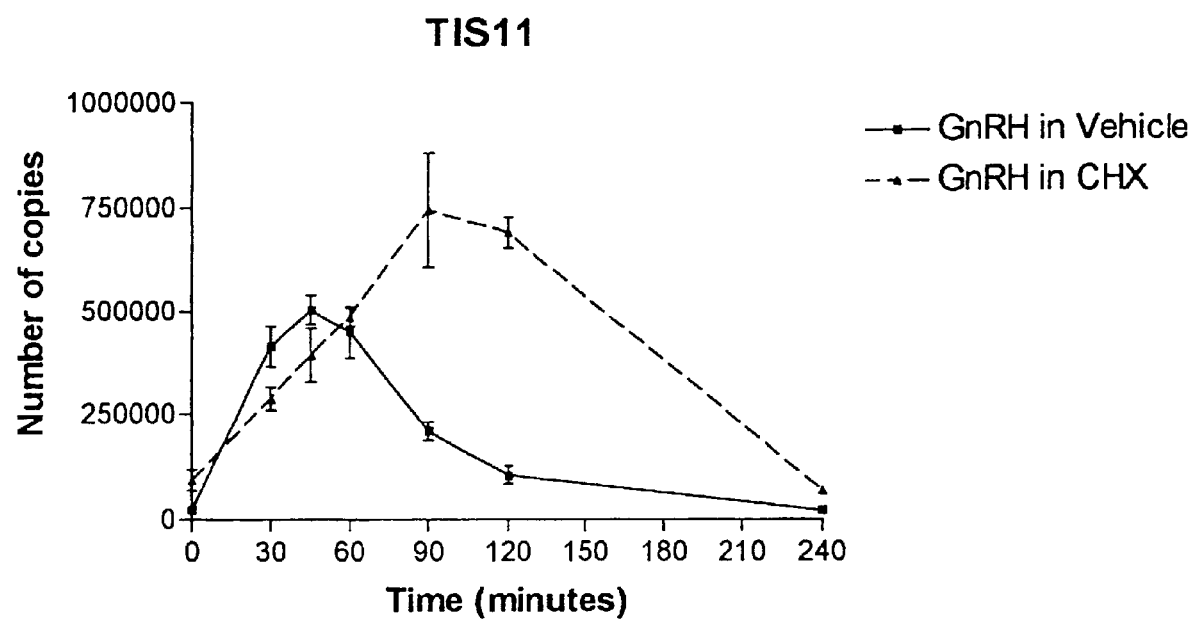
FIG. 14 demonstrates the response over time in the presence and absence of protein synthesis of the IRC TIS11 to signaling activated by GnRH receptor occupancy in the gonadotrope cell line LβT2 cells. The samples analyzed were the same as those in FIG. 9.

PC12 cells were exposed to 200 μM $H_2O_2$ and the responses of various IRCs were determined by real-time PCR at various time points. The results obtained for two IRCs, cfos and egr1 are shown in FIGS. 7 and 8, respectively. As shown in these figures, both IRCs show a marked increase at 1 hour exposure. This level of oxidative stress induced by $H_2O_2$ leads to cell death via apoptosis, as determined by increased Caspase 3 activity by 8 hours and a reduced MTT assay response at 24 hours. Therefore these data indicate that a concentration landscape for $H_2O_2$ or any other known toxin or toxic drug, can be generated. This would allow the prediction of the toxicity of a candidate drug in this cellular target by comparison of the pattern obtained with this drug to those observed with known toxins. Thus the toxins would generate a library of reference landscapes that would serve as predictors of the effects of candidate drugs. The comparison between candidate compounds and reference landscapes could be achieved by representing each IRC at one concentration as a different axis in a conceptual multidimensional space (or matrix) and determining the Euclidean distance between the location of the candidate response profile and that of the reference landscape. Candidates that are closer to the position of known toxins would be predicted to have a higher likelihood of inducing similar toxicity at the corresponding concentrations.

Example 5

Determining the Time Point(s) for Assay of IRCs

The proper time point or time points after exposure can be determined experimentally in any system by performing a time course of the gene response. If a single time point after exposure is assayed, it is best to select a time at which most IRCs are continuing to show an increase in the level of expression. This is usually between 30 minutes and 1 hour. Representative time courses following GnRH exposure to a cell line expressing the GnRH receptor are shown in FIGS. 9-14. In addition, these data demonstrate the feature common to most IRCs, i.e. that their induction is independent of protein synthesis Example 6

Identification and Use of a Calibration Function to Improve the Accuracy of Data Obtained by cDNA Microarray Cell Culture and RNA Sample Preparation: LβT2 cells (University of California, San Diego) were maintained at 37° C. in 5% $CO_2$ in humidified air in DMEM (Mediatech) containing 10% fetal bovine serum (Gemini). 40-50×10$^6$ cells were seeded in 15 cm dishes and medium was replaced 24 hours later with DMEM containing 25 mM HEPES (Mediatech) and glutamine. On the next day, the cells were treated with 100 nM GnRH or vehicle and were returned to the $CO_2$ incubator for 1 hour at which point the medium was replaced with 10 ml lysis buffer (4 M guanidinium thiocyanate. 25 mM sodium citrate, pH 7.0, 0.5% N-lauroyl-sarcosine, and 0.1 M 2-mercaptoethanol). Total RNA was isolated according to the method of Chomczynski and Sacchi (1997) supra. Samples from three vehicle- and three GnRH-exposed cultures were assayed using each of the two microarray platforms studied.

Target selection: 51 genes present on both arrays, including roughly equal numbers of regulated and non-regulated genes, were selected for analysis. Genes that were incorrectly designed on the GENECHIP arrays were excluded from this analysis group and all 51 genes were sequence confirmed on the cDNA array.

Oligonucleotide Microarray Probe labeling and hybridization: First strand cDNA was synthesized by incubating 40 micrograms of total RNA with 400 U SuperScript II reverse transcriptase (Invitrogen, Carlsbad. Calif.), 100 pmol T7-(dT)$_{24}$ primer (5'-GGCCAGTGAATTGTAATACGACT-CACTATAGGGAGGCGG-(dT)$_{24}$-3') (SEQ ID NO:2), 1× first strand buffer (50 mM Tris-HCl (pH 8.3), 75 mM KCl, 3 mM $MgCl_2$), 10 mM DTT and 0.5 mM dNTPs at 42° C. for 1 hour. Second strand synthesis was performed by incubating the first strand cDNA with 10 U *E. coli* ligase (Invitrogen), 40 U DNA polymerase I (Invitrogen). 2 U RNase H (Invitrogen), 1× reaction buffer [18.8 mM Tris-HCl (pH 8.3), 90.6 mM KCl, 4.6 mM $MgCl_2$, 3.8 mM DTT, 0.15 mM NAD, 10 mM $(NH_4)_2SO_4$] and 0.2 mM dNTPs at 16° C. for 2 hours. Ten units of T4 DNA polymerase (Invitrogen) was then added, and the reaction was allowed to continue for another 5 minutes at 16° C. After phenol-chloroform extraction and ethanol precipitation, the double-stranded cDNA was resuspended in 10 microliters DEPC-treated $dH_2O$.

Labeling of the dsDNA was done by in vitro transcription using a BioArray High Yield® RNA transcript labeling kit (Enzo Diagnostics, Farmingdale, N.Y.). Briefly, the dsDNA was mixed with 1× HY reaction buffer. 1× biotin labeled ribonucleotides (NTPs with Bio-UTP and Bio-CTP). 1×DTT. 1× RNase inhibitor mix and 1× T7 RNA polymerase. The mixture was incubated at 37° C. for 5 hours, with gentle mixing every 30 minutes. The labeled cRNA was then purified using an RNEASY® mini kit (Qiagen, Valencia, Calif.) according to the manufacturer's protocol and ethanol precipitated. The purified cRNA was fragmented in 1× fragmentation buffer (40 mM Tris-acetate, 100 mM KOAc, 30 mM MgOAc) at 94° C. for 35 minutes. For hybridization with a GENECHIP cartridge (Affymetrix, Santa Clara, Calif.). 15 micrograms of fragmented cRNA probe was incubated with 50 pM control oligonucleotide B2, 1× eukaryotic hybridization control (1.5 pM BioB. 5 pM BioC, 25 pM BioD and 100 pM cre). 0.1 mg/ml herring sperm DNA. 0.5 mg/ml acetylated BSA and 1× hybridization buffer (100 mM MES, 1M [Na$^+$], 20 mM EDTA, 0.01% Tween 20) in a 45° C. rotisserie oven for 16 hours. Washing and staining was performed with a GENECHIP fluidic station (Affymetrix) using the appropriate antibody amplification washing and staining protocol. The phycoerythrin-stained array was scanned as a digital image file.

Oligonucleotide Array Quality control and data analysis: To assess the quality of the cRNA labeling, the probe was first hybridized to a TEST2 Array® (Affymetrix). The scanned image, was analyzed using Microarray Suite 4.0 after visually being inspected to be free of specks or scratches. Probe labeling was required to exceed the following benchmarks in the test array: low noise (RawQ<15), low background (<600), low 3' to 5' ratio of actin and GAPDH (ratio<2) and presence of control genes cre. BioD and BioC. Probes that gave a satisfactory test hybridization were hybridized with the GENECHIP U74A mouse genome array. A total of six arrays were used (three with vehicle-treated samples and three with GnRH-treated samples). Quality control was identical to that for the TEST2 Array, but because of the smaller feature size on the high density U74A array (20 μm versus 50 μm on the TEST2 Array), a slightly higher noise was acceptable (RawQ<30). Pairwise comparison, with scaling to a common average level of 2500, was done between all possible vehicle-treated versus GnRH-treated sample pairs and the mean-difference of all perfect-match mismatch oligonucleotide pairs for each gene was used for analysis. Results of the analyses were exported to Excel spreadsheets. Genes that showed consistent up-regulation across the nine possible comparisons were tested with an independent set of samples using real time PCR. None of the genes show consistent down-regulation in this experimental paradigm.

cDNA microarray development, probe labeling and hybridization: The design, quality control, validation and detailed protocols for use and analysis of this microarray have been described in Example 2 above. Briefly, it contains 956 clones selected from all NIA 15K library (9) or purchased from Research Genetics. Plasmid inserts were amplified by PCR, products were confirmed by agarose gel electrophoresis and purified. The dried product was spotted in 50% DMSO (3 hits/feature, 3 features/gene) with a GMS 417 Arrayer (Affymetrix) on CMT-GAPS coated glass slides (Corning). DNA was fixed at 85° C. for 2 hours. 20 µg of total RNA from each sample was labeled with either Cy3 or Cy5 using the Atlas indirect labeling kit (Clontech) as indicated by the manufacturer. After array prehybridization (6×SSC, 0.5% SDS. 1% BSA at 42° C. for 45 min), the probe was denatured and hybridized in 24 µl 50% formamid, 6×SSC, 0.5% SDS, 5×Denhardt's with 2.4 µg salmon sperm DNA, 10 µg poly dA at 42° C. for 16 hours. Following 10 min lashes in 0.1×SSC, 0.1% SDS, and twice in 0.1×SSC the slide was scanned using the GMS 418 Scanner (Affymetrix).

cDNA Microarray data analysis: Scanned microarray data were exported as tiff files to Genepix (Axon Instruments) and spot registration was manually optimized as suggested by the developer. The median background-subtracted feature intensity was utilized for further analysis. Overall differences in the signal intensity of the two wavelengths measured on each slide ($\lambda$=532 nm and $\lambda$=635 nm) were corrected using the Loess function in S Plus Professional (Insightful Corporation). Predictors were generated using a symmetric distribution, span=0.75 (10). The ratios of the resulting corrected data for each feature was used for subsequent analysis.

Real-time PCR: The protocol described by Yuen et al. (2001) Meth. Enzymol. 345:556-569. Briefly, 5 µg total RNA was converted into cDNA and 1/200 (approximately 500 pg) was utilized for 40 cycle three-step PCR in an ABI Prism 7700 in 20 mM Tris pH 8.4, 50 mM KCl, 3 mM $MgCl_2$, 200 µM dNTPs, 0.5×SYBR® green (Molecular Probes), 200 µM each primer and 0.5 U Platinum Taq (Life Technologies). Amplicon size and reaction specificity was confirmed by agarose gel electrophoresis. The number of target copies in each sample was interpolated from its detection threshold ($C_T$) value using a plasmid or purified PCR product standard curve included on each plate. The sequence of the primer sets utilized are provided in Example 2. Each transcript in each sample was assayed 5 times and the median $C_T$ values were used for analysis. The mean of the three closest values was calculated and used as the reference value.

cDNA array calibration: The cDNA array data were calibrated according to the following function:

$$Fc = Fa^q$$

where $$q = \frac{\sum \log Fp}{\sum \log Fa}$$

Fc is the corrected fold change. Fa is the microarray fold change and q is calculated using 1 3<Fp<32.

Results. Two related questions were examined: how can the microarray measurements be calibrated to more accurately reflect the relative expression levels of the mRNAs that are assayed, and how does the performance of these two widely used microarray platforms (GeneChip arrays and cDNA arrays) compare. Both approaches were optimized and used to assay multiple samples from the same experimental paradigm, GnRH and vehicle treatment of a gonadotrope cell line. Fifty-one genes present on both arrays, including nearly equal numbers of regulated and unregulated mRNAs, were selected for quantitative independent assay by real-time PCR. The PCR measurements were made in reference to a standard curve in the same samples assayed by the microarrays. Thus, the data from each microarray platform were evaluated in reference to a more quantitative mRNA expression assay. Using these data, calibration procedures were explored and the performance of the two microarray systems were compared.

In order to compare the performance of the two microarray platforms studied and to develop approaches for data calibration, the performance of both microarray approaches and of the real-time PCR used for validation was optimized. The RNA isolation, labeling and GENECHIP hybridization were required to meet stringent quality criteria in both the test-array and final array. The cDNA array was required to manifest low levels of background labeling.

The study disclosed above, addresses the measurement bias of microarray data. There are two components of measurement accuracy, precision and bias. Precision indicates the reproducibility of measurements whereas bias indicates whether the measurements are systematically distorted. The determination of measurement accuracy requires comparison with a non-biased reference measurement. All laboratory measuring devices, from pH meters to scales, require calibration in relationship to known reference standards to reduce measurement bias. The measurements obtained by real-time PCR are used as the reference standards in this study. Real-time PCR was selected for generating reference measurements because of its reproducibility and large measurement range. Note the large measurement range of the assay. Similar standard curves were generated to transform the measurements obtained for all 51 genes utilized for analysis. The measurements of the relative levels of expression of these 51 genes, assayed in the same samples by both microarray and PCR, provide the data for this study. In order to test whether the array measurements are biased, the log of the fold-change values obtained were examined for each gene by microarray and by PCR. In an ideal assay, these ratios should distribute about unity and their log transform about 0. However, both GENECHIP arrays and cDNA arrays shot a marked tendency to underestimate the fold-change ratios of the underlying mRNAs, as determined by PCR.

Although the GENECHIP data is biased towards underestimating the relative mRNA changes, there is no consistent pattern observed for the errors. Various attempts at calibration failed to identify a satisfactory approach to improve data accuracy. Each GENECHIP gene measurement is based on a large number of oligonucleotide hybridizations and the error of each measurement is somewhat idiosyncratic. A dependent variable could not be identified that reliably predicts the degree of error for any given cluster. In contrast, the bias observed with cDNA arrays shows a power scale increase with increasing fold change, causing a linear deviation of the log transformed data. Within a large measurement range (Fa<32) these data show a high power law correlation. This observation indicates that a power law correction would improve data accuracy. A calibration factor, of q=1.4 was obtained (see methods). Use of this simple calibration leads to a marked improvement in cDNA array data accuracy.

Other reports have compared the results obtained by microarray with that using other approaches (Iyer et al. (1999) Science 283(5398):83-87; Tanigushi et al. (2001) supra). However, heretofore, no study has been reported that systematically compared data calibration for different platforms. One recent study reporting an absence of microarray bias was improperly designed and reached invalid conclusions. This previous study used no external reference values and therefore had no basis for an analysis of bias error. In essence, this previous study compared the average deviation of ratios obtained on a cDNA microarray that were normalized to unity with the expected result that these values would be randomly distributed about unity. Not surprisingly, this analysis revealed that 1=1 to a high level of accuracy. However, contrary to the conclusions of the authors, the analysis provides no information about the bias of the measurements obtained (Yue et al. (2001) Nucleic Acids Res. 29(8):E41-1).

Example 7

Use of Gene Reporters to Monitor Cell Toxicity and Reversal of Toxicity by Protective Membrane Receptor Active Drugs Rat PC12 cells that stably express the dopamine D2 receptor were exposed to 200 µM $H_2O_2$, which has been shown to induce cell death via apoptosis after 24 h. Early genes β-actin, PC3, c-fos, and egr1 were assayed by real-time PCR. Three genes were found to be induced at 1 h: PC3, c-fos, and egr1 (FIG. 15). Pramipexole and bromocriptine activate the D2 receptor to stimulate G protein coupling. However, the two D2 receptor agonists can be distinguished by their differing effects on gene expression. Bromocriptine causes a suppression of three early genes induced by $H_2O_2$, whereas pramipexole does not. This effect on gene expression correlates with a similar effect on cell survival. Bromocriptine, but not praxipexole protects the cells against PC12 induced cell death. These results indicate that monitoring these genes provides an assessment of the toxicity induced by $H_2O_2$, and can distinguish the differing effects of drugs acting at the same receptor on cellular signaling tranduction.

Example 8

Figure 16:
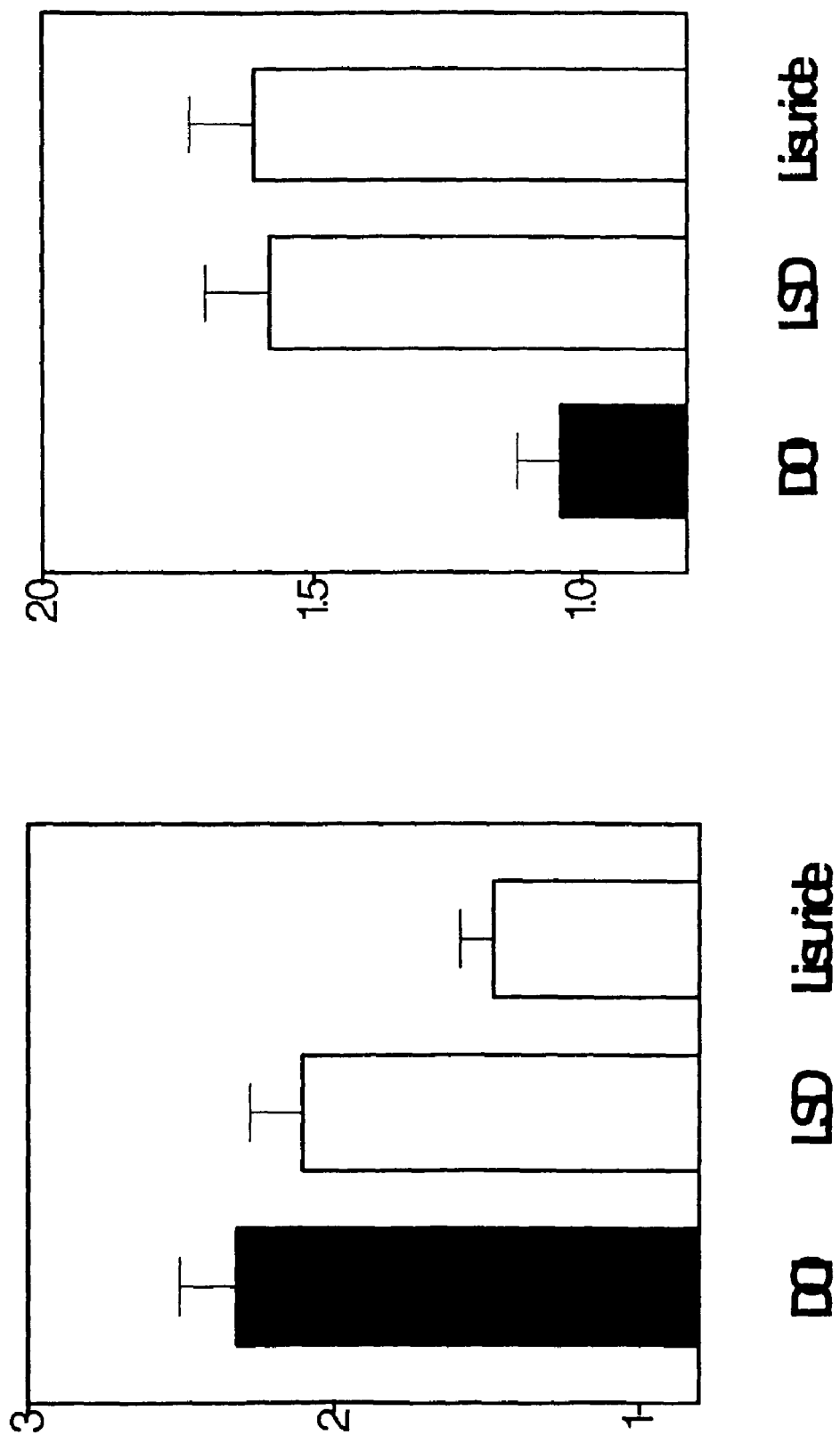
FIG. 16 shows that intrinsic reporters of cell signaling can distinguish drugs acting through the serotonin 5-HT2A receptor in vivo. Results shown are from mouse somatosensory cortex removed 1 h after i.p. exposure to the agents listed.

Intrinsic Reporters of Cell Signaling Distinguish Drugs Acting Through Serotonin 5-HT2A Receptors in the Mouse Somatosensory Cortex Wild-type mice were treated with either drug or saline and after 1 h they were sacrificed and the somatosensory cortex dissected for RNA isolation and assay. RNA expression levels was determined using real-time PCR (FIG. 16). The results for two representative early genes are shown. The data is presented as fold-change relative to the expression average in saline-injected control mice. *** indicates p<0.001 by students t-test., with each data point obtained from a different animal. Note that when assaying just these two selected genes, the effects of DOI, LSD and lisuride on the mouse somatosensory cortex can be distinguished. A total of 8 genes showed increased expression relative to saline injection with at least one of the three drugs tested. The induction of all 8 genes required activation of the serotonin 5-HT2A receptor, because no induction was observed for any of these genes by these drugs in a serotonin 5HT2A receptor gene-knockout mouse model.

TABLE 1

| NAME | HUMAN | MOUSE | RAT | DESCRIPTION |
|---|---|---|---|---|
| 3CH134 | NM_004417 | NM_013642 | AF357203 | 3CH134; CL100; MAP kinase phosphatase-1 (Mkp1); protein tyrosine phosphatase, non-receptor type 16 (Ptpn16); dual specificity phosphate 1 (DUSP1) |
| ania-1 | | | AF030086 | activity and neurotransmitter-induced early gene 1 (ania-1) |
| ania-2 | | | AF030087 | activity and neurotransmitter-induced early gene 2 (ania-2) |
| ania-3 | | | AF030088 | activity and neurotransmitter-induced early gene 3, probable isoform of homer/vesl |
| ania-4 | | AK013421 | NM_021584 | activity and neurotransmitter-induced early gene protein 4 (ania-4); calcium/calmodulin-dependent protein kinase-related peptide; protein serine/threonine kinase CPG16 (cpg16) |
| ania-5 | | | AF030090 | activity and neurotransmitter-induced early gene 5 (ania-5) |
| ania-7 | | | AF050659 | activity and neurotransmitter-induced early gene 7 (ania-7) |
| ania-8 | | | AF050660 | activity and neurotransmitter-induced early gene 8 (ania-8) |
| ania-9 | | | AF050661 | activity and neurotransmitter-induced early gene 9 (ania-9) |
| ania-10 | | | AF050662 | activity and neurotransmitter-induced early gene 10 (ania-10) |
| ania-11 | | | AF050663 | activity and neurotransmitter-induced early gene 11 (ania-11) |
| ania-12 | | | AF050664 | activity and neurotransmitter-induced early gene 12 (ania-12) |
| arc | AF248637 | NM_018790 | NM_019361 | activity regulated cytoskeletal-associated protein (arc); arg3.1 |
| AS3 | NM_015928 | BF451878 | | androgen-induced prostate proliferative shutoff associated protein (AS3); KIAA0979; early onset breast cancer protein BRCA2 region |
| ATF3 | NM_001674 | NM_007498 | NM_012912 | activating transcription factor 3 (Atf3); LRG21; TI-241 |
| Bcl6 | NM_001706 | NM_009744 | | B-cell leukemia/lymphoma 6 (Bcl6); zinc finger protein 51 |

TABLE 1-continued

| NAME | HUMAN | MOUSE | RAT | DESCRIPTION |
|---|---|---|---|---|
| BRF1 | NM_004926 | NM_007564 | NM_017172 | butyrate response factor 1 (Brf1); EGF-response factor 1 (ERF1); cMG1 |
| BRF2 | NM_006887 | NM_007565 | | butyrate response factor 2 (Brf2); EGF-response factor 2 (ERF2) |
| BTG2 | NM_006763 | NM_007570 | NM_017259 | B-cell translocation gene family, member 2 (BTG2); TIS21; PC3 mRNA for NGF-inducible PC3 anti-proliferative protein |
| c-fos | V01512 | V00727 | | |
| c-jun | NM_002228 | NM_010591 | NM_021835 | Jun oncogene (Jun) |
| Cctz | NM_001762 | NM_009838 | | chaperonin subunit 6a (zeta) (Cct6a); CCT (chaperonin containing TCP-1) zeta (Cctz) |
| CD26 | M74777 | | | |
| cox-2 | NM_000963 | NM_011198 | NM_017232 | TIS10; prostaglandin synthase/cyclooxygenase (PGHS-B); glucocortoid-regulated inflammatory prostaglandin G/H synthase (griPGHS); prostaglandin-endoperoxide synthase 2 (Ptgs2); cyclooxygenase-2 (Cox-2) |
| CREB | | | | |
| CREm | NM_001881 | NM_013498 | NM_013086 | cAMP responsive element modulator (Crem) |
| Csnk2a2 | NM_001896 | NM_009974 | L15618 | casein kinase II, alpha 2, polypeptide (Csnk2a2) |
| CTGF | NM_001901 | NM_010217 | NM_022266 | connective tissue growth factor (CTGF); fibroblast inducible secreted protein (Fisp12) |
| CYR61 | NM_001554 | NM_010516 | | cysteine-rich, angiogenic inducer, 61 (CYR61) |
| DUSP1 | NM_004417 | | | |
| DUSP13 | NM_016364 | NM_013849 | | dual specificity phosphatase 13 (Dusp13); TS-DSP6 |
| DUSP2 | NM_004418 | NM_010090 | | dual-specific phosphoprotein phosphatase (PAC1) |
| DUSP3 | NM_004090 | AF280809 | | dual specificity phosphatase 3 (vaccinia virus phosphatase VH1-related) (DUSP3) |
| DUSP4 | NM_001394 | | | |
| DUSP5 | NM_004419 | | | |
| DUSP6 | NM_001946 | | | |
| DUSP8 | NM_004420 | X95518 | | Neuronal tyrosine/threonine phosphatase 1; Dual specificity phosphatase 8 (DUSP8) |
| DUSP9 | NM_001395 | | | |
| egr-1 | NM_001964 | NM_007913 | NM_012551 | krox-24; zif-268; nerve growth factor induced gene-A (NGFI-A); ETR103; ZENK |
| egr-2 | NM_000399 | X06746 | AB032420 | krox-20 |
| egr-3 | NM_004430 | NM_018781 | NM_017086 | early growth response 3 (Egr3); Pilot |
| egr-4 | NM_001965 | NM_020596 | NM_019137 | early growth response 4 (Egr4); Zinc-finger transcription factor NGFI-C |
| elF2beta | | AA600468 | | eukaryotic translation initiation factor 2, subunit 2 (beta, 38 kD) |
| ERp99 | NM_003299 | NM_011631 | S69315 | tumor rejection antigen gp96 (Tra1); endoplasmic reticulum transmembrane protein (ERp99); glucose regulated protein (grp 94) |
| EST | | AW049031 | | |
| EST | XM_027639 | AW120868 | | |
| EST | | AK011748 | | |
| EST | | AA822174 | | |
| EST | NM_022152 | AV084836 | | PP1201 protein |
| ETR101 | NM_004907 | NM_010499 | | ETR101; immediate early response 2 (Ier2); growth factor inducible immediate early protein (pip92) |
| Fnk | NM_004073 | U21392 | AF136584 | serine/threonine kinase (Fnk); cytokine-inducible kinase; PRK |
| fosB | NM_006732 | X14897 | | |
| fra-1 | X16707 | NM_010235 | NM_012953 | Fos-like antigen 1 (Fosl1) |
| fra-2 | NM_005253 | NM_008037 | NM_012954 | Fos like antigen 2 (Fosl2) |
| gamma-actin | | NM_009609 | | |
| gem | NM_005261 | NM_010276 | | GTP binding protein (gene overexpressed in skeletal muscle); Ras-like protein (kir) |
| GFNHR | NM_002135 | | | |
| GKLF | NM_004235 | NM_010637 | AF390546 | Gut-enriched Kruppel-like factor GKLF; epithelial zinc-finger protein EZF (Zie) |
| Glut1 | NM_006516 | M23384 | M13979 | glucose transporter 1; facilitated glucose transport protein; solute carrier family 2 |
| grg | | NM_010347 | | related to Drosophila groucho gene (Grg) |
| HB-GAM | NM_002825 | NM_008973 | NM_017066 | Pleiotrophin; Heparine binding factor; heparin-binding growth associated molecule; heparin binding growth factor 8; neurite growth-promoting factor 1; osteoblast stimulating factor-1 (osf1) |
| Herpud1 | NM_014685 | NM_022331 | AB033771 | homocysteine-inducible, endoplasmic reticulum stress-inducible, ubiquitin-like domain member 1 (Herpud1) |
| HMGCR | NM_000859 | X07888 | NM_013134 | 3-hydroxy-3-methylglutaryl coenzyme A reductase |
| Homer-1a | | NM_011982 | AJ276327 | homer, neuronal immediate early gene, 1; Vesl-1S; homer-1a |

TABLE 1-continued

| NAME | HUMAN | MOUSE | RAT | DESCRIPTION |
|---|---|---|---|---|
| Homer-1b | NM_004272 | AF093258 | AF093267 | Homer, neuronal immediate early gene, 1B (SYN47) |
| Homer-1c | | | AF093268 | |
| Homer-2 | NM_004839 | | | Homer, neuronal immediate early gene, 2 (HOMER-2B) |
| Homer-3 | NM_004838 | BC005773 | | Homer, neuronal immediate early gene, 3 (HOMER-3) |
| Hsd17b7 | | NM_010476 | | hydroxysteroid 17-beta dehydrogenase 7 (Hsd17b7) |
| HSP70 | L12723 | | | |
| Ier5 | NM_016545 | NM_010500 | AB032086 | immediate early response 5 (Ier5) |
| IEX-1 | NM_003897 | X67644 | X96437 | radiation-inducible immediate-early gene IEX-1, p22(PRG1/IEX-1); apoptosis inhibitor (IEX-1L); immediate early response 3 (IER3); Dif-2; gly96 |
| Ifrd1 | NM_001550 | NM_013562 | NM_019242 | interferon-related developmental regulator 1 (Ifrd1); interferon related, developmental regulator, nerve growth factor-inducible; TPA induced sequence 7, TIS7 |
| Il1rl1 | NM_003856 | NM_010743 | NM_013037 | interleukin 1 receptor-like 1 (Il1rl1); ST2L; T1; Fos-responsive gene 1; Fit-1 |
| Irf1 | | | NM_012591 | Interferon regulatory factor 1 (Irf1) |
| junB | X51345 | NM_008416 | NM_021836 | Jun-B oncogene(Junb) |
| junD | NM_005354 | NM_010592 | | Jun proto-oncogene related gene d1 (Jund1); Nrf1 splice variant D (Nrf1) |
| Jundp2 | | NM_030887 | U53449 | Jun dimerization protein 2 (Jundp2) (AP-1 repressor, transcriptional inhibitory factor) |
| KLF12 | NM_007249 | NM_010636 | | Kruppel-like factor 12 (Klf12) |
| KLF9 | | NM_010638 | | Kruppel-like factor 9 (Klf9); BTEB-1 transcription factor |
| LKLF | NM_016270 | NM_008452 | AF181251 | Kruppel-like factor 2 (lung) (Klf2) |
| LZF | | AY036117 | | leucine-zipper-containing transcription factor LZF (Lzf) |
| MAD-3 | NM_020529 | | | IkBa; MAD-3 mRNA encoding IkB-like activity; nuclear factor of kappa light polypeptide gene enhancer in B-cells inhibitor, alpha (NFKBIA) |
| MAIL | NM_031419 | NM_030612 | | molecule possessing ankyrin-repeats induced by lipopolysaccharide (Mail); IL-1 inducible nuclear ankyrin-repeat protein (INAP); IkappaB-zeta |
| mcl-1 | | NM_008562 | NM_021846 | myeloid cell leukemia sequence 1 |
| midnolin | | NM_021565 | | midnolin |
| Mpc2 | NM_003655 | NM_007625 | | chromobox homolog 4 (Drosophila Pc class) (Cbx4); transcriptional repressor Polycomb 2 (Mpc2) |
| Neurod1 | NM_002500 | U28068 | NM_019218 | neurogenic differentiation 1 (NEUROD1) |
| NFATC3 | NM_004555 | D85612 | | nuclear factor of activated T-cells, cytoplasmic, calcineurin-dependent 3 (NFATC3) |
| NFIL3 | NM_005384 | NM_017373 | AY004663 | nuclear factor, interleukin 3, regulated (Nfil3); NFIL3/E4BP4 transcription factor |
| NGFI-B | NM_002135 | X16995 | NM_024388 | NGFI-B; Nr4a1; TR3; NP10; GFRP1; N10; NAK-1; HMR |
| NOT | NM_006186 | NM_013613 | NM_019328 | NOT; nuclear receptor subfamily 4, group A, member 2 (NR4A2); Nurr1;TINUR; HZF-3; RNR-1 |
| Nr4a3 | NM_006981 | NM_015743 | NM_031628 | nuclear receptor subfamily 4, group A, member 3; mitogen-inducible nuclear orphan receptor (MINOR); neuron-derived orphan receptor (NOR-1); CSMF; CHN |
| Oazi | NM_015878 | NM_018745 | NM_022585 | ornithine decarboxylase antizyme inhibitor (Oazi) |
| OSM | NM_020530 | D31942 | | oncostatin M |
| PAI1 | NM_000602 | NM_008871 | NM_012620 | plasminogen activator inhibitor, type I (Planh1); PAI-1; serine (or cysteine) proteinase inhibitor, clade E (nexin, plasminogen activator inhibitor type 1), member 1 (SERPINE1) |
| Pem | | NM_008818 | NM_022175 | placentae and embryos oncofetal gene (Pem) |
| Period1 | NM_002616 | NM_011065 | | Period1; Rigui |
| Pyst1 | X93921 | | | |
| Rad | NM_004165 | NM_019662 | U12187 | Ras-related associated with diabetes, (Rrad); Ras-like GTP-binding protein (Rad) |
| Rad9 | | NM_011237 | | radio-resistance/chemo-resistance/cell cycle checkpoint control protein (Rad9) |
| RAG1 | NM_000448 | NM_009019 | | recombination activating gene 1 (Rag1) |
| Rasd1 | NM_016084 | NM_009026 | AF239157 | RAS, dexamethasone-induced 1 (Rasd1); ras-related protein (DEXRAS1); activator of G protein signaling (AGS1) |
| Rem | NM_014012 | NM_009047 | | rad and gem related GTP-binding protein (Rem) |
| RGS2 | NM_002923 | NM_009061 | AF279918 | regulator of G-protein signaling 2 (Rgs2); helix-loop-helix basic phosphoprotein (G0S8) |

TABLE 1-continued

| NAME | HUMAN | MOUSE | RAT | DESCRIPTION |
|---|---|---|---|---|
| rhoB | | NM_007483 | NM_022542 | ras-related gene rhoB |
| Ruvbl1 | | NM_031707 | | PSD-Zip45, a novel Homer/vesl family protein |
| RZR-beta | | | L14610 | transcription factor RZR-beta |
| Scyb10 | NM_001565 | NM_021274 | U22520 | small inducible cytokine B subfamily (Cys-X-Cys), member 10 (Scyb10); macrophage interferon inducible protein 10 (IP-10); crg-2; mob-1 |
| Sil | | NM_009185 | | Tal1 interrupting locus (Sil); SCL gene locus |
| Synaptobrevin-3 | U64520 | | | |
| Syt4 | AF299075 | NM_009308 | NM_031693 | synaptotagmin 4 (Syt4); somatostatin transactivating factor-1 |
| TGFbeta1 | | | | transforming growth factor-beta |
| TGFbeta2 | | | | |
| TGFbeta3 | | | | |
| TIEG | NM_005655 | NM_013692 | NM_031135 | TGFB inducible early growth response (TIEG); glial cell-derived neurotrophic factor inducible transcription factor (GIF) |
| TIS11 | NM_003407 | NM_011756 | X63369 | TIS11; zinc finger protein 36 (Zfp36); tristetraproline (TTP); Berg36; G0S24; NUP475 |
| Tob1 | NM_005749.11 | NM_009427 | | transducer of ErbB-2.1 (Tob1) |
| TSC22 | NM_006022 | NM_009366 | NM_013043 | transforming growth factor beta 1 induced transcript 4 (Tgfb1i4); transcriptional regulator TSC-22 |
| tubulin-a2 | | M13446 | | alpha-tubulin isotype M-alpha-2 |
| USF2 | NM_003367 | NM_011680 | | upstream transcription factor 2, c-fos interacting (USF2) |
| WSB1 | | NM_019653 | | |
| YY1 | NM_003403 | NM_009537 | | YY1 transcription factor (YY1, delta), GLI-Kruppel-related protein; DNA-binding protein (NF-E1); UCR-motif DNA-binding protein (UCRBP); delta transcription factor |
| Vesl-1L | | AB019479 | | Vesl-1L |

TABLE 2

Confirmed Microarray-identified genes regulated by GnRH in LβT2 cells

| Gene Name | Accession | SYBR PCR (n = 9) | Microarray (n = 3) |
|---|---|---|---|
| Egr1 | NM_007913 | 390.6 ± 83.9 | 12.9 ± 3.8 |
| Egr2 | AA727313 | 294.7 ± 35.6 | 1.5 ± 0.2 |
| LRG21 | U19118 | 96.8 ± 15.7 | 31.2 ± 16.6 |
| c-fos | J00370 M36605 | 52.0 ± 5.8 | 12.5 ± 4.0 |
| Nr4a1/nur77 | AI322974 | 49.4 ± 10.1 | 5.9 ± 1.5 |
| Ier2/Pip92 | W14782 | 17.1 ± 2.4 | 5.2 ± 1.2 |
| Rgs2 | NM_009061 | 8.7 ± 0.4 | 4.0 ± 1.3 |
| c-jun | NM_010591 | 6.6 ± 0.9 | 3.8 ± 0.6 |
| Period1 | AB030818 | 4.9 ± 1.1 | 2.1 ± 0.1 |
| Gem | AA177829 | 4.3 ± 0.3 | 1.7 ± 0.2 |
| γ-actin | L21996 | 3.9 ± 0.4 | 2.7 ± 0.3 |
| gly96 | X67644 | 3.8 ± 0.5 | 1.7 ± 0.6 |
| MKP1/3CH134 | W34966 | 3.4 ± 0.4 | 1.4 ± 0.1 |
| TSC22 | NM_009366 | 3.3 ± 0.2 | 3.4 ± 0.4 |
| Klf4 | NM_010637 | 2.9 ± 0.3 | 1.7 ± 0.3 |
| 1κB | NM_010907 | 2.6 ± 0.2 | 1.7 ± 0.2 |
| Klf-like EST | BE368139 | 2.5 ± 0.2 | 2.3 ± 0.3 |
| PRL1 | NM_011200 | 2.1 ± 0.1 | 2.0 ± 0.4 |
| HSP30 | NM_019979 | 1.9 ± 0.2 | 1.3 ± 0.2 |
| transgelin | AF149291 | 1.8 ± 0.2 | 1.4 ± 0.1 |
| NMDMC | NM_008638 | 1.6 ± 0.3 | 1.4 ± 0.3 |
| β-actin | NM_007393 | 1.6 ± 0.1 | 2.0 ± 0.5 |
| Nrf2 | U20532 | 1.5 ± 0.1 | 1.3 ± 0.2 |

TABLE 3

List of primers used in real time PCR

| Gene | GenBank | Forward | Position | Reverse | Position | Ampican size | Description |
|---|---|---|---|---|---|---|---|
| 3CH134 | X61940 | TGACATCCGCGTATGAGAG | 1506-1624 | CTGGCTTTGTCTGTCAGTGC | 1770-1789 | 184 | growth factor inducible immediate early gene 3CH134 |
| JX1-YPO | AA968093 | ACCTTTCTGCCTGCATCTC | 25-44 | CAAGAACGTGAGGCTCAAGG | 193-212 | 185 | IMAGE 1617562 |
| A1R | AW537421 | CAGGCTCTTCCTTCAGTTGG | 274-293 | GACTTTCCATCTGCCTCCAC | 89-108 | 205 | adenosine A1 receptor |
| MOUSE | NM_007438 | GTGGGAAGAAGGAGAACCTG | 1321-1040 | CTGCAGTGTTGATGAGCAG | 1190-1209 | 189 | aldolase 1, A solom |
| ATP103 | AF140023 | ATGTGTGAGTCGTGCCTGTC | 1463-1488 | TGCTGTTTCATCCCTGTGTC | 1637-1656 | 188 | Na, K-ATPase beta 3 subunit |
| ATPase | X61423 | ATGTCTGTCTCGCCATCTCT | 1513-1522 | CATTCATAAGGACGCAGCAC | 1671-1690 | 173 | sodiumpotassium ATPase beta subunit |
| beta-actin | X03672 | AGGTGCACAGCATTGCTTCTG | 1544-1663 | GCTGCCTCAACACCTCACC | 1813-1831 | 188 | beta-actin |
| c-fos | V00727 | TTCCTGGCAATAGCGTGTTG | 3556-3575 | TTCAGAACCACCTCGACAATG | 3705-3724 | 169 | c-fos oncogene |
| c-jun | J04115 | TGAAAGCTGTGTCCCCTGTG | 2735-2754 | ATCACAGCACATGCCACTTC | 2936-2955 | 221 | c-jun oncogene |
| Clcn3 | NM_007711 | GAAGGGATTGTTGGCAGTTC | 2371-2300 | AGGCGTCCGTTGTCACTTAC | 2554-2573 | 203 | chloride channel 3 |
| Cox8a | NM_007750 | TTCCTGCTTCGTGTGTTGTC | 160-179 | GATTGCAGAAGAGGTGACTGG | 343-363 | 204 | cytochrome c oxidase subunit VIIIa |
| ef2 | M76131 | CAGCCAAGTGGTAGCTGAGAC | 723-743 | TGAGTGCTGAGTGATGTCAGG | 901-921 | 199 | elongation factor 2 |
| agr1 | M20157 | TCCCTCCATCACATGCCTG | 2145-2164 | CACTCTGACACATGCTCCAG | 2403-2489 | 345 | early growth response 1 |
| agr2 | K06746 | TGTTAACAGGGGTCTCCATGTG | 2514-2534 | AGCGGCAGTGACATTGAAG | 2703-2721 | 208 | early growth response 2 (Krox 20) |
| lasyn | AF127033 | GAGCCTTTCTACCGTGTGG | 7821-7840 | GAGCAGGAGGACAGGACAAGAC | 8015-8034 | 214 | fatty acid synthase |
| gamma actin | M21435 | TGGATCTCTGTGAGCACCAC | 1488-1507 | AGGCAACTAACAACCGATGG | 1671-1690 | 203 | gamma actin |
| GAPDH | NM_008084 | TGCCACTTCAACAGGAACTC | 890-909 | CTTGCTCAGTGTCCTTGCTG | 1070-1083 | 200 | glyceraldehyde 3 phosphate dehydrogenase |
| Gata2 | NM_008090 | CAGGCTTCTGTTGTGCTGTG | 2725-2744 | TACTTCCGGTTAGGGTGCTC | 2912-2931 | 207 | GATA binding protein 2 |
| gem | U10551 | TTAAGACACGCTTCGGGTTC | 1234-1253 | TATGCAGTGAGCCCTTCTCC | 1372-1391 | 158 | Gem GTPase |
| GKLF | U20344 | TGATGTGCTTGGTGAGTTG | 2313-2332 | TTGCACATCTGAAACCACAG | 2498-2515 | 203 | gut-enriched Kruppel-like factor |
| glutran | M22398 | CCTGTGTCTTCTTCCTACCCACC | 2120-2140 | GCAAGAGTGTCCGTGTCTTC | 2299-2318 | 199 | facilitated glucose transport protein |
| gly96 | X67644 | ACTCCCAGCTTGGGGATTAG | 1553-1572 | TACTAGGCGACCCCAGACAG | 1844-1863 | 211 | growth factor-inducible immediate early gene gly96 |

TABLE 3-continued

List of primers used in real time PCR

| Gene | GenBank | Forward | Position | Reverse | Position | Ampican size | Description |
|---|---|---|---|---|---|---|---|
| Gno2rs1 | NM_008143 | GGATCTCAATGAAGGCAAGC | 781-790 | TTGCTGCTGGTGCTGATAAC | 924-943 | 183 | guanine nucleotide binding protein beta 2 related sequence |
| Hdac1 | NM_008228 | GTGCCTGCTTAGGAGCTCTG | 1716-1735 | CCTCCACCCTACAGAATTGG | 1878-1897 | 182 | histone deacetylase 1 |
| Hsp40 | AB029272 | GCCAGAGCATCACAAGCAATAC | 1542-1651 | TCTGAGAAGTGCCAGGTGTG | 1804-1823 | 182 | heat shock protein 40 |
| Hsp70-4 | NM_015765 | CTTCCGTTTGCCTTGAACTC | 1400-1419 | TCAGGATGCAACCTCAACAG | 1601-1620 | 221 | heat shock protein, 70 kDa 4 |
| Hsp86-1 | NM_010480 | TTCGTGTTTGCTTGCTCTGTG | 621-640 | GGTTGTTCTCGGACTTTGG | 2852-2871 | 202 | heat shock protein, 86 kDa 1 |
| HSPC030 | NM_019970 | GCCTGACTGATACGCAGTTC | 765-784 | ATGGCTTGGAAAAGCCAGAC | 853-872 | 252 | heat shock protein, 30 kDa |
| ikBa | NM_010907 | TCGCTCTTGTTGAAATGTGC | 1322-1341 | TCATAGGGCAGCTCATCCTC | 954-973 | 209 | I kappa B alpha |
| junD | J05205 | TGGAAGAGAACGGGAGTG | 1322-1341 | AAAAGAGAGGGATGGTGTC | 1487-1505 | 185 | junD proto-oncogene |
| Kv9 3 | BG066045 | CGAGCGTTGAAGACAATGAG | 304-319 | ATGTCAGGAAGGACACGAG | 251-232 | 107 | Shab-related delayed rectifier K+ channel |
| LRG21 | U19113 | CTTTGTGCCAACAGAGGATG | 1404-1423 | AGGCTGTGGCTGTGGTTATC | 1584-1603 | 200 | transcription factor LRG21 |
| tyr8 | M57597 | CGGGTTATTCTTGTGATTCG | 2452-2471 | GCATAAGTGAAAGGGGCAGAC | 2608-2629 | 177 | protein tyrosine kinase tyr8 |
| MIF | L02913 | TGACTTTTAGCGGCACGAAC | 198-207 | GACTCAAGCGAAGGTGAAC | 367-405 | 209 | growth factor-induced delayed early response protein |
| Mlp | NM_010807 | GGGGCTTATACTCCCAAACC | 1150-1169 | CCTCCCTCCTGAAGCCTAAC | 1336-1355 | 205 | MARCKS-like protein |
| Mcr2 | NM_008618 | CCAGAGGGAGAGTTCGTGTC | 865-884 | AAAGCGGTCTCCTTTTCCTC | 1045-1064 | 200 | malate dehydrogenase, soluble |
| minic2 | NM_008638 | TCGTCAGGAAGGGTTAGAG | 1625-1645 | GCGCCAAAGAAAACAGACAC | 1811-1820 | 135 | methylenetetrahydrololate dehydrogenase (NAD+ dependent) |
| Nrf2 | U20632 | CAGCATGTTAGGTTATGAGG | 1920-1939 | GCTCAGAAAAGGCTCCATCC | 2052-2071 | 152 | p45 NF E2 related factor 2 |
| nur77 | Jo4113 | GGGTGACCCCACTATTTGTC | 2104-2123 | CGGAAGAGATCTCGAGTTGG | 2292-2311 | 203 | thyroid hormone reactor nur77 |
| pad1 | BC003742 | AAGCAGGATCCCAAACGTC | 1045-1054 | CACCAGATCACCTTCAGTTCC | 1222-1242 | 197 | 26S proteasome-associated pad1 homolog |
| pip92 | M59821 | CCTAGGGACTGGGAAGTGAC | 1184-1203 | TGTCTACGGCAGCAACTACG | 1354-1373 | 190 | growth factor inducible protein pip92 |
| PPL1 | U84411 | CGTCACTGAGGACACTTTTGC | 2498-2518 | CGGTGCCCAACATTCAAC | 2651-2658 | 171 | protein tyrosine phosphatase PRL1 |
| PPL2 | AK017872 | TTCTTGGGAGCACACACTTC | 1233-1302 | CCCTAAAAGTGCCCAGGTG | 1466-1484 | 202 | protein tyrosine phosphatase PRL2 |
| PTPT9 | D28530 | ACTTCGACGCTTCTGTGTG | 6289-6308 | GTGGCCATGCTCCCTGTAGTC | 6454-6473 | 185 | protein tyrosine phosphatase PTPT9 |

TABLE 3-continued

List of primers used in real time PCR

| Gene | GenBank | Forward | Position | Reverse | Position | Ampican size | Description |
|---|---|---|---|---|---|---|---|
| RAB1 | BC002077 | GCTACATGAGACCAGGAGTC | 1067-1086 | GCGTGAAACTGACAGACAC | 1203-1222 | 158 | RAB1 member RAS oncogene family |
| RGS2 | NM_009061 | GCTACATGAGACCAGGAGTC | 648-667 | CCTAGGTTGCTGACTTCCTG | 814-833 | 186 | regulator of G protein signaling 2 |
| Rigui | AF022992 | GGGTCTTCGGTTAAGGTTGC | 4345-4364 | TTCACGGACCTGGATCCTAC | 4509-4523 | 134 | Rigui (Period 1) |
| rPL37a | NM_009034 | TCTGTGGCAAGACCAAGATG | 149-153 | GACAGCAGGGCTTCTACTGG | 291-310 | 171 | ribosomal protein L37a |
| rPL7 | M85235 | ATCTACAAGCGAGGCTACGG | 535-555 | TGGGGAAGACAGTTTGAAGG | 705-724 | 139 | ribosomal protein L7 |
| rPS11 | U93654 | CGTGACGAAGATGAAGATGC | 235-255 | GCACATTGAATCGCACAGTC | 418-435 | 200 | ribosomal protein S11 |
| rPS3 | NM_012052 | AGGTTGTGGTGTTTGGGAAC | 409-428 | GAGGCTTCTTGGGACCAATG | 596-615 | 207 | ribosomal protein S3 |
| Sil | NM_009135 | AATTCTGCCTTCTTCGTCTG | 4555-4535 | AACCCCAGTACTGCCTCATC | 4726-4745 | 180 | Tall interrupting locus (Sil) |
| Stat3B | BC003805 | ACCTCTGAGTCTGGGGATGG | 2700-2719 | AAGTGCAGAGCCAGGAGTTC | 2870-2889 | 190 | Signal transducer and activator of transcription 3 |
| STY | M38381 | CGACTCATGATAGCAGGGAAC | 1221-1241 | AGAAGCTCATGTTCGGCATC | 1412-1431 | 211 | serine threonine tyrosine urase |
| T1S21 | NM_007570 | TCAGCTCCTCCAGTTTCTGCTC | 2092-2112 | GTGTGCCGACAAAAACAAG | 2275-2294 | 203 | B cell translocation gene 2, antiproliferative |
| Tamm40 | NM_016871 | AGGTGGGTGTGGACTTTGAG | 701-720 | TATTCTTGCCGTGGGTTCAGG | 885-904 | 204 | translocase of outer miochondrial membrane 40 homolog |
| transgelin | AF149291 | GATGCTGCACCGACACTTC | 1082-1100 | CCCCTTAGCCACAGTGAGAG | 1260-1279 | 198 | transgelin |
| TSC22 | X52940 | GGCAAAAACCACACTGAAG | 1422-1441 | ACAGGTGAGGTGCAGAAACC | 1596-1615 | 194 | TSC-22 |
| tubulin | BC002219 | TGCCTTTGTGTCACTGGTATG | 1295-1314 | CTGGAGCAGTTTGACGACAC | 1456-1485 | 191 | tubulin alpha 1 |
| vtg-1 | U70622 | GAAACCAAGCATGTGGTGTG | 1843-1867 | CACTCTTTGGGTGACAAGCTC | 2038-2058 | 211 | lysophosphatoic acid reactor |

What is claimed is:

1. A method of evaluating and/or predicting whether a candidate compound has a beneficial therapeutic receptor active drug activity or a hallucinogenic or toxic side-effect as compared to a group of reference compounds that have known beneficial therapeutic receptor active drug activities or known hallucinogenic or toxic side-effects comprising:

a) contacting a candidate compound and a group of reference compounds with a cell in vitro or in vivo for a time period to allow transcription of one or more Intrinsic Reporters of Cell Signaling (IRCS) comprising one or more first/early response genes in the cell, wherein the time period is determined to represent the early accumulation of one or more RNA transcripts, and wherein the time period extends from the time of contact of the candidate compound with the cell to the time of transcription of the first/early genes in a signal transduction pathway and up to 2 hours after said contact; and wherein the candidate compound and reference compounds are tested during the same time period;

b) determining the response profile for the one or more IRCS; and c) comparing the response profile for the one or more IRCS determined in step b) with a corresponding response profile for a group of reference compounds having known beneficial therapeutic receptor active drug activities or known hallucinogenic or toxic side effects; wherein the IRCS demonstrate a reproducible and statistically significant increase of 1.3 fold or greater of the RNA level transcribed from an early response gene by one hour after exposure to a candidate compound at 37° C.;

wherein said comparing of the response profile for the one or more IRCS to the response profile to each of the known reference compounds within the group determines if the response profile is similar to that of a reference compound having known beneficial therapeutic receptor active drug activity, wherein the candidate compound is selected for beneficial therapeutic receptor active drug activity; or determines if the response profile is similar to that of a reference compound having known hallucinogenic or toxic side effects, wherein the candidate compound is rejected for having hallucinogenic or toxic side effects and said comparing is performed using statistical analyses.

2. The method of claim 1, further comprising:

d) determining the EC50 and maximal response for one or more IRCS in the presence of the candidate compound; and e) comparing the EC50 and maximal response for one or more IRCS in the presence of the candidate compound with the EC50 and maximal response for one or more IRCS in the presence of one or more known reference compounds by calculating the Euclidean distances between the EC50 and maximal responses of the candidate compound and one or more reference compounds that have been plotted in multidimensional space or by using a similarity matrix.

3. The method of claim 1, wherein an optimum time point for determining the response profile of one or more Intrinsic Reporters of Cell Signaling comprising one or more first/early response genes is obtained empirically from characterizing the responses observed between the time of contact of a candidate compound with a cell and up to 2 hours after said contact.

4. The method of claim 1, wherein multiple concentrations of the candidate compound and the known reference compounds are tested at multiple time points, wherein the multiple time points fall within the time of contact of the candidate compound with the cell until 2 hours later in order to determine the time period during which the IRCS continues to show an increase in the level of expression.

5. The method of claim 1, wherein the determining includes the use of a data analysis algorithm based on thresholding by fold-change and t-test value determination.

6. The method of claim 1, wherein the candidate compound being evaluated is determined to have a beneficial therapeutic receptor active drug activity or a hallucinogenic or toxic side-effect as compared to a group of reference compounds that have known beneficial therapeutic receptor active drug activities or known hallucinogenic or toxic side-effects by determining the location of the candidate compound within a similarity matrix and comparing this location to that of a group of known reference compounds and one or more Intrinsic Reporters of Cell Signaling.

7. The method of claim 1, wherein the Intrinsic Reporters of Cell Signaling comprise one or more genes that show a reproducible increase or decrease in the RNA level transcribed from the genes in response to exposure of a cell to a compound or external stimulus.

8. The method of claim 1, wherein the Intrinsic Reporters of Cell Signaling may or may not show an increase in all cells or experimental systems tested.

9. The method of claim 1, wherein the candidate compound identified as having a beneficial therapeutic receptor active drug activity or a hallucinogenic or toxic side-effect as compared to a group of reference compounds having a known beneficial therapeutic receptor active drug activity or a known hallucinogenic or toxic side-effect is used to generate a database wherein each candidate compound is assigned a position in multidimensional space or in a similarity matrix, and wherein said multidimensional space or similarity matrix is used for evaluation of any new candidate compound for predicting its beneficial therapeutic receptor active drug activity or hallucinogenic or toxic side-effects based on its location relative to all previous candidate compounds or reference compounds tested.

10. A method of evaluating a candidate compound to determine whether it has a beneficial therapeutic receptor active drug activity or a hallucinogenic or toxic side-effect as compared to a group of reference compounds having known beneficial therapeutic receptor active drug activities or known hallucinogenic or toxic side-effects comprising:
   a. contacting a candidate compound and a group of reference compounds with a cell in vitro or in vivo for a period of time to allow transcription of one or more Intrinsic Reporters of Cell Signaling (IRCS) comprising one or more first/early response genes, wherein the time period is determined to represent the period of accumulation of one or more RNA transcripts, and wherein the time period extends from the time of contact of the candidate compound with the cell to the time of transcription of the first/early genes in a signal transduction pathway and up to 2 hours after said contact; and wherein the candidate compound and reference compounds are tested during the same time period;
   b. determining the pattern and/or level of expression of one or more Intrinsic Reporters of Cell Signaling comprising one or more first/early response genes in the cell after contacting the cell with the candidate compound; and
   c. comparing the pattern of expression of one or more Intrinsic Reporters of Cell Signaling generated in the cell of step b) to a group of reference compounds generated in accordance with the method of claim 9;
   wherein the candidate compound being evaluated may be selected or rejected based on whether the pattern of expression of one or more Intrinsic Reporters of Cell Signaling is similar to that of the group of reference compounds having known beneficial therapeutic receptor active drug activities, wherein the candidate compound is selected for having a beneficial therapeutic receptor active drug activity and fewer side effects compared to each of the known reference compounds in the database or the pattern of expression of one or more Intrinsic Reporters of Cell Signaling is similar to that of the group of reference compounds having known hallucinogenic or toxic side-effects, wherein the candidate compound is rejected, wherein said comparing or similarity is determined using statistical analyses.

11. The method of claim 10, wherein the pattern and/or level of expression of one or more Intrinsic Reporters of Cell Signaling comprising one or more genes in a cell reflects the relative activation of different signaling pathways in that cell in response to exposure to a compound or external stimulus.

12. The method of claim 10, wherein the pattern and/or level of expression of one or more Intrinsic Reporters of Cell Signaling is assembled into a signaling landscape representative of the response in a given cell to a particular compound or external stimulus.

13. The method of claim 12, wherein the signaling landscape generated for one or more Intrinsic Reporters of Cell Signaling in a given cell provides a basis for predicting the cellular response of that cell to an unknown compound or external stimulus.

14. The method of claim 13, wherein the cellular response of a particular cell type to a compound or external stimulus establishes a global profile of physiological changes or signaling responses in that cell type.

15. The method of claim 2, wherein the EC50 and maximal response for each Intrinsic Reporter of Cell Signaling is determined by a method selected from the group consisting of a microarray, a dot blot hybridization, a slot blot hybridization, a Real-time PCR using fluorescent dyes, a Real-time PCR using TaqMan assay, a Real-time PCR using hybridization probes, a Real-time PCR using molecular beacons, a quantitative competitive PCR, a northern blot analysis, a RNase nuclease protection assay and a S1 nuclease protection assay.

16. The method of claim 1, wherein the cell is selected from the group consisting of an isolated cell, an isolated cell line, a cell within a tissue, a cell within a portion of a tissue and a cell within an animal subject.

17. The method of claim 16, wherein the animal subject is selected from the group consisting of a rabbit, a mouse, a rat, a cat, a dog, a monkey and a human.

18. The method of claim 10, wherein the cell is selected from the group consisting of an isolated cell, an isolated cell line, a cell within a tissue, a cell within a portion of a tissue and a cell within an animal subject.

19. The method of claim 18, wherein the animal subject is selected from the group consisting of a rabbit, a mouse, a rat, a cat, a dog, a monkey and a human.

20. A method for predicting whether a new compound will have a beneficial therapeutic receptor active drug activity or a hallucinogenic or toxic side-effect that is shared by a group of other compounds by identifying the Intrinsic Reporters of Cell Signaling comprising one or more first/early response genes that show similar changes with this group of compounds in vitro or in vivo within the time period determined to represent the accumulation of the first/early IRCS RNA transcripts, wherein the time period determined to represent the accumulation of the first/early IRCS RNA transcripts is from the time of contact of the new compound with a cell up to 2 hours after contact, wherein the IRCS demonstrate a reproducible and statistically significant increase of 1.3 fold or greater of the RNA level transcribed from an early response gene by one hour after exposure to a candidate compound at 37° C.; and testing the new compound to determine whether it causes similar changes as determined by Euclidean distances or similarity matrices for these Intrinsic Reporters of Cell Signaling.

21. The method of claim 4, wherein an optimal single time point to assay each IRCS is determined as the latest time point at which the IRCS is continuing to increase after exposure to at least one candidate compound, and wherein the optimal single time point to assay each IRCS ranges from about 45 minutes to one hour after contacting the cell with the candidate compound.

22. The method of claim 21, wherein the single time point to be used for a set of IRCS in a given experimental system is determined as being the average optimal time point for all of the individual IRCS.

* * * * *